US010448929B2

(12) United States Patent
Bangera et al.

(10) Patent No.: US 10,448,929 B2
(45) Date of Patent: *Oct. 22, 2019

(54) SYSTEMS, METHODS, AND DEVICES FOR ASSESSING MICROBIOTA OF SKIN

(71) Applicant: Elwha LLC, Bellevue, WA (US)

(72) Inventors: Mahalaxmi Gita Bangera, Renton, WA (US); Michael H. Baym, Cambridge, MA (US); Roderick A. Hyde, Redmond, WA (US); Jordin T. Kare, San Jose, CA (US); Eric C. Leuthardt, St. Louis, MO (US); Gary L. McKnight, Bothell, WA (US); Tony S. Pan, Kirkland, WA (US); Katherine E. Sharadin, Redmond, WA (US); Elizabeth A. Sweeney, Seattle, WA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/272,921

(22) Filed: Feb. 11, 2019

(65) Prior Publication Data
US 2019/0254642 A1 Aug. 22, 2019

Related U.S. Application Data

(63) Continuation of application No. 15/366,811, filed on Dec. 1, 2016, now Pat. No. 10,219,789, which is a
(Continued)

(51) Int. Cl.
*A61B 10/02* (2006.01)
*G01N 33/569* (2006.01)
(Continued)

(52) U.S. Cl.
CPC .............. *A61B 10/02* (2013.01); *A61F 13/15* (2013.01); *G01N 33/56911* (2013.01); *G01N 33/56938* (2013.01); *H04N 5/23229* (2013.01)

(58) Field of Classification Search
CPC ............. A61B 10/02; G01N 33/56911; G01N 33/56938; A61F 13/15; H04N 5/23229
See application file for complete search history.

(56) References Cited

U.S. PATENT DOCUMENTS 4,384,288 A 5/1983 Walton
5,077,210 A 12/1991 Eigler et al.
(Continued)

FOREIGN PATENT DOCUMENTS

JP 2002-284618 A 10/2002
WO WO 2008/059274 A1 5/2008
(Continued)

OTHER PUBLICATIONS

Adak et al.; "Bishydrazide Glycoconjugates for Lectin Recognition and Capture of Bacterial Pathogens"; Bioconjug Chem; Nov. 17, 2010; pp. 1-27; vol. 21; No. 11.
(Continued)

*Primary Examiner* — Trevor Love

(57) ABSTRACT

Devices, systems, and methods for assessing microbiota of skin are described, including: a skin-covering material including an inner surface and an outer surface, the inner surface substantially conforming to a topography of a skin surface of an individual and including a plurality of signal-generating complexes, one or more of the plurality of signal-generating complexes configured to emit one or more signals in response to at least one type of microbe; an image capture device to capture an image of the inner surface of the skin-covering material, the image including one or more signals emitted from the plurality of signal-generating complexes, and to transform the image into a digital output; and
(Continued)

a computing device including circuitry configured to receive the digital output, compare the properties of the imaged one or more signals with a database of reference signal-generating complexes, and generate a digital spatial profile of microbes on the skin-covering material.

20 Claims, 21 Drawing Sheets

Related U.S. Application Data continuation of application No. 13/975,079, filed on Aug. 23, 2013, now Pat. No. 9,557,331.

(51) Int. Cl.
*A61F 13/15* (2006.01)
*H04N 5/232* (2006.01)

(56) References Cited

U.S. PATENT DOCUMENTS

| | | |
|---|---|---|
| 5,728,028 A | 3/1998 | Dusch |
| 5,747,022 A | 5/1998 | Slavtcheff |
| 6,106,457 A | 8/2000 | Perkins et al. |
| 6,199,557 B1 | 3/2001 | Laughlin |
| 6,255,461 B1 | 7/2001 | Mosbach et al. |
| 6,291,234 B1 | 9/2001 | Raz et al. |
| 6,371,370 B2 | 4/2002 | Sadler et al. |
| 6,379,920 B1 | 4/2002 | El-Sayed et al. |
| 6,433,244 B1 | 8/2002 | Roe et al. |
| 6,797,522 B1 | 9/2004 | Still et al. |
| 6,802,811 B1 | 10/2004 | Slepian |
| 6,905,692 B2 | 6/2005 | Farmer |
| 7,070,590 B1 | 7/2006 | Santini, Jr. et al. |
| 7,215,976 B2 | 5/2007 | Brideglall |
| 7,303,875 B1 | 12/2007 | Bock et al. |
| 7,314,453 B2 | 1/2008 | Kuo |
| 7,319,038 B2 | 1/2008 | Southard |
| 7,386,333 B1 | 6/2008 | Birecki et al. |
| 7,413,567 B2 | 8/2008 | Weckwerth et al. |
| 7,494,465 B2 | 2/2009 | Brister et al. |
| 7,507,402 B1 | 3/2009 | Farmer et al. |
| 7,931,592 B2 | 4/2011 | Currie et al. |
| 8,028,708 B2 | 10/2011 | Molema et al. |
| 8,041,147 B2 | 10/2011 | Molnar et al. |
| 8,109,875 B2 | 2/2012 | Gizewski |
| 8,260,010 B2 | 9/2012 | Chhibber et al. |
| 8,358,348 B2 | 1/2013 | Mohammadi et al. |
| 8,385,619 B2 | 2/2013 | Soenksen |
| 8,557,560 B2 | 10/2013 | Martin Jiménez et al. |
| 9,028,846 B2 | 5/2015 | Eddy |
| 9,186,278 B2 | 11/2015 | Baym et al. |
| 9,199,044 B2 * | 12/2015 | Bangera ............ G06F 17/5086 |
| 2003/0007942 A1 | 1/2003 | Koenig |
| 2003/0108896 A1 | 6/2003 | Vogt |
| 2003/0173525 A1 | 9/2003 | Seville |
| 2003/0225362 A1 | 12/2003 | Currie et al. |
| 2004/0078219 A1 | 4/2004 | Kaylor et al. |
| 2004/0111035 A1 | 6/2004 | Kondoh et al. |
| 2004/0125996 A1 | 7/2004 | Eddowes et al. |
| 2004/0202685 A1 | 10/2004 | Manzo |
| 2004/0223985 A1 | 11/2004 | Dunfield et al. |
| 2005/0019291 A1 | 1/2005 | Zolotarsky et al. |
| 2005/0171434 A1 | 8/2005 | Madden et al. |
| 2006/0037197 A1 | 2/2006 | Hawes et al. |
| 2006/0048278 A1 | 3/2006 | Pitsolis |
| 2006/0052739 A1 | 3/2006 | Henley et al. |
| 2006/0172318 A1 | 8/2006 | Medinz et al. |
| 2006/0257993 A1 | 11/2006 | McDevitt et al. |
| 2007/0134337 A1 | 6/2007 | Villanueva et al. |
| 2007/0134649 A1 | 6/2007 | Kolari et al. |
| 2008/0060148 A1 | 3/2008 | Pinyayev et al. |
| 2008/0139974 A1 | 6/2008 | Da Silva |
| 2008/0262321 A1 | 10/2008 | Erad et al. |
| 2008/0262576 A1 | 10/2008 | Creamer et al. |
| 2009/0001012 A1 | 1/2009 | Kepner et al. |
| 2009/0041727 A1 | 2/2009 | Suzuki et al. |
| 2009/0186342 A1 | 7/2009 | Bruno et al. |
| 2009/0286263 A1 | 11/2009 | Graham et al. |
| 2010/0055161 A1 | 3/2010 | Ahn |
| 2010/0074872 A1 | 3/2010 | Blaser et al. |
| 2010/0185064 A1 | 7/2010 | Bandic et al. |
| 2010/0204802 A1 | 8/2010 | Wilson et al. |
| 2010/0239625 A1 | 9/2010 | Puckett et al. |
| 2010/0331641 A1 | 12/2010 | Bangera et al. |
| 2011/0035898 A1 | 2/2011 | Marek et al. |
| 2011/0117025 A1 | 5/2011 | Dacosta et al. |
| 2011/0212485 A1 | 9/2011 | Mitragotri et al. |
| 2011/0245094 A1 | 10/2011 | Washburn et al. |
| 2011/0274676 A1 | 11/2011 | Farmer et al. |
| 2012/0058464 A1 | 3/2012 | Ermantraut et al. |
| 2012/0065086 A1 | 3/2012 | Benson |
| 2012/0092461 A1 | 4/2012 | Fisker et al. |
| 2012/0171193 A1 | 7/2012 | Blaser et al. |
| 2012/0241391 A1 | 9/2012 | Carlson et al. |
| 2013/0078298 A1 | 3/2013 | Av-Gay et al. |
| 2013/0079605 A1 | 3/2013 | Bandaru et al. |
| 2013/0084259 A1 | 4/2013 | Lee |
| 2013/0115317 A1 | 5/2013 | Charbonneau et al. |
| 2013/0218024 A1 | 8/2013 | Boctor et al. |
| 2013/0317741 A1 | 11/2013 | Brashear et al. |
| 2013/0338039 A1 | 12/2013 | Mazed et al. |
| 2014/0037688 A1 | 2/2014 | Berkes et al. |
| 2014/0309662 A1 | 10/2014 | Brewer et al. |
| 2015/0054944 A1 | 2/2015 | Bangera et al. |
| 2015/0054945 A1 | 2/2015 | Bangera et al. |
| 2015/0148684 A1 | 5/2015 | Baym et al. |
| 2015/0148685 A1 | 5/2015 | Baym et al. |
| 2015/0339513 A1 | 11/2015 | Bolea |

FOREIGN PATENT DOCUMENTS

| | | |
|---|---|---|
| WO | WO 2008/086596 A1 | 7/2008 |
| WO | WO 2010/093503 A2 | 8/2010 |
| WO | WO 2010/094976 A1 | 8/2010 |
| WO | WO 2011/103144 A1 | 8/2011 |
| WO | WO 2012/044794 A2 | 4/2012 |
| WO | WO 2013/070893 A1 | 5/2013 |

OTHER PUBLICATIONS

Ammor, Mohammed Salim; "Recent Advances in the Use of Intrinsic Fluorescence for Bacterial Identification and Characterization"; J Fluoresc; Mar. 12, 2007; pp. 1-5; Springer Science + Business Media, LLC.

"Antibody Mimetic"; Wikipedia; Feb. 6, 2011; pp. 1-2; located at: http://en.wikipedia.org/wiki/Antibody_mimetic.

Baddour et al.; "High Frequency Ultrasound Imaging of Changes in Cell Structure Including Apoptosis"; PDF created on Aug. 12, 2013; pp. 1-6; IEEE.

Barlen et al.; "Detection of *Salmonella* by Surface Plasmon Resonance"; Sensors; Aug. 7, 2007; pp. 1427-1446; vol. 7; MDPI.

Bernardini et al.; "The 3D Model Acquisition Pipeline"; Computer Graphics Forum; 2002; pp. 149-172; vol. 21; No. 2; The Eurographics Association and Blackwell Publishers Ltd.

Bhatta et al.; "Use of Fluorescence Spectroscopy to Differentiate Yeast and Bacterial Cells"; Applied Microbiology and Biotechnology; 2006; pp. 121-126; vol. 71; No. 1.

Blank et al.; "A force-based protein biochip"; PNAS; Sep. 30, 2003; pp. 11356-11360; vol. 100; No. 20; The National Academy of Sciences of the USA.

Bouchard et al.; "Optical characterization of Pseudomonas fluorescens on meat surfaces using time-resolved fluorescence"; Journal of Biomedical Optics; Jan./Feb. 2006; pp. 014011-1-014011-7; vol. 11; No. 1.

Brennan, John D.; "Preparation and Entrapment of Fluorescently Labeled Proteins for the Development of Reagentless Optical Biosensors"; Journal of Fluorescence; Apr. 28, 1999; pp. 295-312; vol. 9; No. 4; Plenum Publishing Corporation.

(56) References Cited

OTHER PUBLICATIONS

Bright et al.; "Regenerable Fiber-Optic-Based Immunosensor"; Analytical Chemistry; May 15, 1990; pp. 1065-1069; vol. 62, No. 10; American Chemical Society.

Cady et al.; "Optimized linkage and quenching strategies for quantum dot molecular beacons"; Molecular and Cellular Probes; 2007; pp. 116-124; vol. 21; Elsevier Ltd.

Cao et al.; "Molecular Beacon Aptamers for Protein Monitoring in Real-Time and in Homogeneous Solutions"; Current Proteomics; 2005; pp. 31-40; vol. 2; Bentham Science Publishers Ltd.

Chawla et al.; "An overview of passive RFID"; IEEE Applications & Practice; Sep. 2007; pp. 11-17; IEEE.

Chen et al.; "Aptamer from whole-bacterium SELEX as new therapeutic reagent against virulent *Mycobacterium tuberculosis*"; Biochemical and Biophysical Research Communications; Apr. 11, 2007; pp. 743-748; vol. 357; Elsevier Inc.

Cho et al.; "The Human Microbiome: at the interface of health and disease"; Nat Rev Genet; Oct. 1, 2012; pp. 260-270; vol. 13; No. 4.

Chung et al.; "Size Comparisons among Integral Membrane Transport Protein Homologues in Bacteria, Archaea, and Eucarya"; Journal of Bacteriology; Feb. 2001; pp. 1012-1021; vol. 183; No. 3; American Society for Microbiology.

Cockburn et al.; "High throughput DNA sequencing to detect differences in the subgingival plaque microbiome in elderly subjects with and without dementia"; Investigative Genetics; 2012; pp. 1-12; vol. 3; No. 19; Cockburn et al, Biomed Central Ltd.

Cole et al.; "The Ribosomal Database Project: improved alignments and new tools for rRNA analysis"; Nucleic Acids Research; published online Nov. 12, 2008; pp. D141-D145; vol. 37; The Author(s).

Cowan et al.; "Development of engineered biofilms on poly-L-lysine patterened surfaces"; Biotechnology Letters; Accepted May 23, 2001; pp. 1235-1241; vol. 23; Kluwer Academic Publishers; Netherlands.

Crawford et al.; "Peptide aptamers: Tools for biology and drug discovery"; Briefings in Functional Genomics and Proteomics; Apr. 2003; pp. 72-79; vol. 2; No. 1; Henry Stewart Publications.

Crowe et al.; "Candida albicans binds human plasminogen: identification of eight plasminogen-binding proteins"; Molecular Microbiology; 2003; pp. 1637-1651; vol. 47; No. 6; Blackwell Publishing Ltd.

De Château et al.; "Protein PAB, an Albumin binding Bacterial Surface Protein Promoting Growth and Virulence"; The Journal of Biological Chemistry; revised Jul. 22, 1996; pp. 26609-26615; vol. 271; No. 43; Issue of Oct. 25, 1996; The American Society for Biochemistry and Molecular Biology, Inc.; USA.

Dewhirst et al.; "The Human Oral Microbiome"; Journal of Bacteriology; Accepted Jul. 10, 2010; pp. 5002-5017; vol. 192; No. 19; American Society for Microbiology.

Didenko et al.; "Horseradish peroxidase-driven fluorescent labeling of nanotubes with quantum dots"; Biotechniques; NIH Public Access Author Manuscript; Mar. 2006; pp. 295-302; vol. 40; No. 3.

Doornbos et al.; "White Blood Cell Differentiation Using a Solid State Flow Cytometer"; Cytometry; accepted Mar. 16, 1993; pp. 589-594; vol. 14; Wiley-Liss, Inc.

Dwarakanath et al.; "Quantum dot-antibody and aptamer conjugates shift fluorescence upon binding bacteria"; Biochemical and Biophysical Research Communications; Received Oct. 11, 2004; pp. 739-743; vol. 325; Elsevier Inc.

Elston, Dirk M.; "Fluorescence of fungi in superficial and deep fungal infections"; BMC Microbiology; Sep. 24, 2001; pp. 1-4; vol. 1; No. 21; Elston.

Fan et al.; "Sensitive optical biosensors for unlabeled targets: A review"; Analytica Chimica Acta; 2008; pp. 8-26; vol. 620; Elsevier B.V.

Fan et al.; "Structures in Bacillus subtilis Are Recognized by CD14 in a Lipopolysaccharide Binding Protein-Dependent Reaction"; Infection and Immunity; Jun. 1999; pp. 2964-2968; vol. 67; No. 6; American Society for Microbiology.

Fei-Fei et al.; "One-Shot Learning of Object Categories"; IEEE Transactions on Pattern Analysis and Machine Intelligence; Apr. 2006; pp. 594-611; vol. 28; No. 4; IEEE Computer Society.

Feng et al.; "Computer-assisted technique for the design and manufacture of realistic facial prostheses"; British Journal of Oral and Maxillofacial Surgery; 2010; pp. 105-109; vol. 48; The British Association of Oral and Maxillofacial Surgeons.

Finkenzeller, Klaus; "RFID Handbook: Fundamentals and Applications in Contactless Smart Cards and Identification"; printed on Apr. 16, 2014; pp. 29-59; John Wiley & Sons, Ltd.

Freeman et al.; "Chemiluminescent and Chemiluminescence Resonance Energy Transfer (CRET) Detection of DNA, Metal Ions, and Aptamer—Substrate Complexes Using Hemin/G-Quadruplexes and CdSe/ZnS Quantum Dots"; Journal of The American Chemical Society; 2011; pp. 11597-11604; vol. 133; American Chemical Society.

Gaitanis et al.; "The Malassezia Genus in Skin and Systemic Diseases"; Clinical Microbiology Reviews; Jan. 2012; pp. 106-141; vol. 25; No. 1; American Society for Microbiology.

Gao et al.; "A Micro Sensing Probe for Detecting Individual Biological Cells"; Proceedings of the $25^{th}$ Annual International Conference of the IEEE EMBS, Cancun, Mexico; Sep. 17-21, 2003; pp. 3348-3351; IEEE.

Gauglitz et al.; "Host Defence Against Candida albicans and the Role of Pattern-recognition Receptors"; Acta Derm Venereol; 2012; pp. 291-298; vol. 92; The Authors; Journal Compilation: Acta Dermato-Venereologica.

Giana et al.; "Rapid Identification of Bacterial Species by Fluorescence Spectroscopy and Classification Through Principal Components Analysis"; Journal of Fluorescence; Nov. 2003; pp. 489-493; vol. 13, No. 6; Plenum Publishing Corporation.

Gopinath et al.; "Aptamer That Binds to the gD Protein of Herpes Simplex Virus 1 and Efficiently Inhibits Viral Entry"; Journal of Virology; Jun. 2012; pp. 6732-6744; vol. 86; No. 12; American Society for Microbiology.

Graham, Anna R.; "Fungal Autofluorescence with Ultraviolet Illumination"; American Journal of Clinical Pathology; Feb. 1983; pp. 231-234; vol. 79; No. 2; American Society of Clinical Pathologists.

Grice et al.; "A diversity profile of the human skin microbiota"; Genome Research; 2008; pp. 1043-1050; vol. 18; Cold Spring Harbor Laboratory Press.

Grice et al.; "The skin microbiome"; Nature Reviews—Microbiology; Apr. 2011; pp. 244-253; vol. 9; Macmillan Publishers Limited.

Griffen et al.; "CORE: A Phylogenetically-Curated 16S rDNA Database of the Core Oral Microbiome"; PLoS One; Apr. 2011; pp. 1-10; vol. 6; Issue 4; Griffen et al.

Hagleitner et al.; "Smart single-chip gas sensor microsystem"; Nature; Nov. 15, 2001; pp. 293-296; vol. 414; Macmillan Magazines Ltd.

Harz et al.; "Vibrational Spectroscopy—A Powerful Tool for the Rapid Identification of Microbial Cells at the Single-Cell Level"; Cytometry Part A Journal of the International Society for Advancement of Cytometry; 2009; pp. 104-113; vol. 75A; International Society for Advancement of Cytometry.

Helm et al.; "Classification and identification of bacteria by Fourier-transform infrared spectroscopy"; Journal of General Microbiology; 1991; pp. 69-79; vol. 137; SGM; Printed in Great Britain.

Hildebrand et al.; "Acoustic microscopy of living cells"; Proc. Natl. Acad. Sci.; Mar. 1981; pp. 1656-1660; vol. 78; No. 3.

Hilton, Peter J.; "Laser induced fluorescence imaging of bacteria"; SPIE; PDF created on Aug. 12, 2013; pp. 1174-1178; vol. 3491.

Hornyak, Tim; "RFID Powder"; Scientific American; Feb. 2008; pp. 68-71; Scientific American, Inc.

Huff et al.; "Light-scattering sensor for real-time identification of Vibrio parahaemolyticus, Vibrio vulnificus and Vibrio cholera colonies on solid agar plate"; Microbial Biotechnology; 2012; pp. 607-620; vol. 5, No. 5; The Authors; Microbial Biotechnology—Society for Applied Microbiology and Blackwell Publishing Ltd.

Ikanovic et al.; "Fluorescence Assay Based on Aptamer-Quantum Dot Binding to Bacillus Thuringiensis Spores"; J Fluoresc; 2007; pp. 193-199; vol. 17; Springer Science + Business Media, LLC.

(56) References Cited

OTHER PUBLICATIONS

Jaiswal et al.; "Long-term multiple color imaging of live cells using quantum dot bioconjugates"; Nature Biotechnology; Jan. 2003; pp. 47-51; vol. 21; Nature Publishing Group; www.nature.com/naturebiotechnology.

Jhaveri et al.; "In vitro selection of signaling aptamers"; Nature Biotechnology; Dec. 2000; pp. 1293-1297; vol. 18; Nature America Inc.

Kashyap et al.; "Surface Plasmon Resonance-Based Fiber and Planar Waveguide Sensors"; Journal of Sensors; Accepted Jun. 26, 2009; pp. 1-9; vol. 2009; Hindawi Publishing Corporation.

Kim et al.; "Lens-Free Imaging for Biological Applications"; Journal of Laboratory Automation; Jan. 27, 2012; pp. 43-49; vol. 17; No. 1; Society for Laboratory Automation and Screening.

Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.

Koenig et al.; "Laser-Induced Autofluorescence for Medical Diagnosis"; Journal of Fluorescence; 1994; pp. 17-40; vol. 4; No. 1; Plenum Publishing Corporation.

Koo et al.; "Development of a Streptavidin-Conjugated Single-Chain Antibody That Binds Bacillus cereus Spores"; Applied and Environmental Microbiology; Jul. 1998; pp. 2497-2502; vol. 64; No. 7; American Society for Microbiology.

Kumar et al.; "AnimalLectinDB: An integrated animal lectin database"; Bioinformation; published Apr. 22, 2011; pp. 134-136; vol. 6; No. 3; Biomedical Informatics.

Kupper et al.; "Generation of human antibody fragments against *Streptococcus mutans* using a phage display chain shuffling approach"; BMC Biotechnology; Jan. 25, 2005; pp. 1-12; vol. 5; No. 4; Kupper et al.

Lee et al.; "A micro-machined LC-resonator for high-frequency magnetic sensor applications"; Intermag 2006; Downloaded on Nov. 17, 2009; pp. 1.

Lee et al.; "Graphene-Based Chemiluminescence Resonance Energy Transfer for Homogeneous Immunoassay"; ACS NANO; 2012; pp. 2978-2983; vol. 6; No. 4; American Chemical Society.

Liu et al.; "Deep Sequencing of the Oral Microbiome Reveals Signatures of Periodontal Disease"; PLos One; Jun. 2012; pp. 1-16; vol. 7; Issue 6; Liu et al.

Low et al.; "A DNA Aptamer Recognizes the Asp f 1 Allergen of Aspergillus fumigatus"; Biochem Biophys Res Commun.; Aug. 28, 2009; pp. 544-548; vol. 386; No. 3; Elsevier Inc.

Majid et al.; "Integration of stereophotogrammetry and triangulation-based laser scanning system for precise mapping of craniofacial morphology"; The International Archives of the Photogrammetry, Remote Sensing and Spatial Information Sciences; 2008; pp. 805-812; vol. XXXVII; Part B5; Beijing.

Markiewicz et al.; "The Use of 3D Imaging Tools in Facial Plastic Surgery"; Facial Plast Surg Clin N Am; 2011; pp. 655-682; vol. 19; Elsevier Inc.

Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26; No. 5; IEEE Computer Society.

Mateus et al.; "Adherence of Candida albicans to Silicone Induces Immediate Enhanced Tolerance to Fluconazole"; Antimicrobial Agents and Chemotherapy; Sep. 2004; pp. 3358-3366; vol. 48; No. 9; American Society for Microbiology.

Meerwaldt et al.; "Skin Autofluorescence, a Measure of Cumulative Metabolic Stress and Advanced Glycation End Products, Predicts Mortality in Hemodialysis Patients"; Journal of the American Society of Nephrology; 2005; pp. 3687-3693; vol. 16; American Society of Nephrology.

Modlin, Robert L.; "Innate Immunity: Ignored for decades, but not forgotten"; J Invest Dermatol.; Mar. 2012; pp. 882-886; vol. 132; No. 3.

Mohan et al.; "Bokode: Imperceptible Visual tags for Camera Based Interaction from a Distance"; PDF created on Aug. 12, 2013; pp. 1-8; http://cameraculture.media.mit.edu/bokode.

Mohanty et al.; "Micro Electrical Impedance Spectroscopy of Bovine Chromaffin Cells"; printed on Nov. 14, 2013; pp. 1-5.

Murakami et al.; "A miniature confocal optical microscope with mems gimbal scanner"; Transducers '03; The $12^{th}$ International Conference on Solid State Sensors, Actuators and Microsystems, Boston, Jun. 8-12, 2003; pp. 587-590; IEEE.

Nakatsuji et al.; "Antibodies Elicited by Inactivated Propionibacterium acnes-Based Vaccines Exert Protective Immunity and Attenuate the IL-8 Production in Human Sebocytes: Relevance to Therapy for Acne Vulgaris"; Journal of Investigative Dermatology; published online May 8, 2008; pp. 2451-2457; vol. 128; The Society for Investigative Dermatology.

Nitsche et al.; "One-step selection of Vaccinia virus-binding DNA aptamers by MonoLEX"; BMC Biotechnology; published Aug. 15, 2007; pp. 1-12; vol. 7; No. 48; Nitsche et al.

Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.

Ozalp et al.; "Antimicrobial aptamers for detection and inhibition of microbial pathogen growth"; Future Microbiology; Mar. 2013; pp. 387-401; vol. 8, No. 3; 1 page provided by Examiner.

PCT International Search Report; International App. No. PCT/US2014/052081; dated Nov. 20, 2014; pp. 1-8.

PCT International Search Report; International App. No. PCT/US2014/052077; dated Nov. 28, 2014; pp. 1-4.

PCT International Search Report; International App. No. PCT/US2014/052086; dated Nov. 28, 2014; pp. 1-3.

PCT International Search Report; International App. No. PCT/US2014/051928; dated Dec. 1, 2014; pp. 1-3.

PCT International Search Report; International App. No. PCT/US2014/051934; dated Dec. 1, 2014; pp. 1-3.

Peppas et al.; "Polymers and Gels as Molecular Recognition Agents"; Pharmaceutical Research; May 2002; pp. 578-587; vol. 19; No. 5; Plenum Publishing Corporation.

Proske et al.; "Aptamers—basic research, drug development, and clinical applications"; Appl Microbiol Biotechnol; Published online Nov. 11, 2005; pp. 367-374; vol. 69; Springer-Verlag.

Quast et al.; "The SILVA ribosomal RNA gene database project: improved data processing and web-based tools"; Nucleic Acids Research; Published Nov. 28, 2012; pp. D590-D596; vol. 41; The Author(s) 2012; Oxford University Press.

Raghavan et al.; "BIAcore: a microchip-based system for analyzing the formation of macromolecular complexes"; Structure; Apr. 15, 1995; pp. 351-333; vol. 3; No. 4; Current Biology Ltd.

Rucker et al.; "Functional Antibody Immobilization on 3-Dimensional Polymeric Surfaces Generated by Reactive Ion Etching"; Langmuir; In Final Form Jun. 2, 2005; pp. 7621-7625; vol. 21; American Chemical Society.

Seidl et al.; "Opto-mechanical combination of a line scanning camera and a micro laser scanner system"; PDF created on Aug. 12, 2013; pp. 1-6.

Selinummi et al.; "Software for quantification of labeled bacteria from digital microscope images by automated image analysis"; BioTechniques; Dec. 2005; pp. 859-863; vol. 39; No. 6.

Shimobaba et al.; "Gigapixel inline digital holographic microscopy using a consumer scanner"; Physics Optics; May 27, 2013; pp. 1-6; Optical Society of America.

Snow et al.; "Chemical Detection with a Single-Walled Carbon Nanotube Capacitor"; Science; Mar. 25, 2005; pp. 1942-1945; vol. 307; American Association for the Advancement of Science.

Son et al.; "An implantable wireless microdosimeter for radiation oncology"; MEMS 2008, Tucson, AZ, USA; Jan. 13-17, 2008; pp. 256-259; IEEE.

Spear et al.; "Isolation, characterization, and recovery of small peptide phage display epitopes selected against viable malignant glioma cells"; Cancer Gene Therapy; Received Mar. 5, 2001; pp. 506-511; vol. 8, No. 7; Nature Publishing Group.

(56) References Cited

OTHER PUBLICATIONS

Sun et al.; "An Enhanced Active Shape Model for Facial Features Extraction"; 2008 11th IEEE International Conference on Communication Technology Proceedings; 2008; pp. 661-664; IEEE.

Sun et al.; "Broadband single cell impedance spectroscopy using maximum length sequences: theoretical analysis and practical considerations"; Measurement Science and Technology; 2007; pp. 2589-2868; vol. 18; IOP Publishing Ltd, UK.

Szeliski, Richard; "Image Alignment and Stitching: A Tutorial"; Computer Graphics and Vision; 2006; pp. 1-104; vol. 2; No. 1; R. Szeliski.

Tachon et al.; "Experimental conditions affect the site of tetrazolium violet reduction in the electron transport chain of Lactococcus lactis"; Microbiology; Accepted Jun. 7, 2009; pp. 2941-2948; vol. 155; SGM.

Terada et al.; "Bacterial adhesion to and viability on positively charged polymer surfaces"; Microbiology; Accepted on Aug. 22, 2006; pp. 3575-3583; vol. 152; SGM.

Ulicny, J.; "Lorenz-Mie Light Scattering in Cellular Biology"; Gen. Physiol. Biophys.; 1992; pp. 133-151; vol. 11.

Valm et al.; "Systems-level analysis of microbial community organization through combinatorial labeling and spectral imaging"; PNAS; Mar. 8, 2011; pp. 4152-4157; vol. 108; No. 10.

Van Heerbeek et al.; "Three dimensional measurement of rhinoplasty results"; Rhinology; 2009; pp. 121-125; vol. 47.

Vashist, Sandeep Kumar; "A Review of Microcantilevers for Sensing Applications"; AZojono Journal of Nanotechnology Online; Jun. 2007; pp. 1-15; vol. 3; AZoM.com Pty Ltd.

Yasuda et al.; "Lectin Microarray Reveals Binding Profiles of Lactobacillus casei Strains in a Comprehensive Analysis of Bacterial Cell Wall Polysaccharides"; Applied and Environmental Microbiology; Jul. 2011; pp. 4539-4546; vol. 77, No. 13; American Society for Microbiology.

Ye et al.; "Molecularly imprinted polymers as antibody and receptor mimics for assays, sensors and drug discovery"; Anal Bioanal Chem; Published online Jan. 22, 2004; pp. 1887-1897; vol. 378; Springer-Verlag.

Yusa et al.; "Controlled multiple quantum coherences of nuclear spins in a nanometre-scale device"; Nature; Apr. 21, 2005; pp. 1001-1005; vol. 434; Nature Publishing Group.

Zelada-Guillen et al.; "Immediate Detection of Living Bacteria at Ultralow Concentrations Using a Carbon Nanotube Based Potentiometric Aptasensor"; Angew. Chem. Int. Ed; 2009; pp. 1-4; vol. 48; Wiley-VCH Verlag GmbH & Co. KGaA; Weinheim.

Zharov et al.; "In vivo high-speed imaging of individual cells in fast blood flow"; Journal of Biomedical Optics; Sep./Oct. 2006; pp. 054034-1-054034-4; vol. 11; No. 5; SPIE.

Zharov et al.; "In vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zheng et al.; "Enhanced active shape model for facial feature localization"; Proceedings of the Seventh International Conference on Machine Learning and Cybernetics, Kunming; Jul. 12-15, 2008; pp. 2841-2845; IEEE.

Zitova et al.; "Image registration methods: a survey"; Image and Vision Computing; accepted Jun. 2003; pp. 977-1000; vol. 21; Elsevier B.V.

* cited by examiner

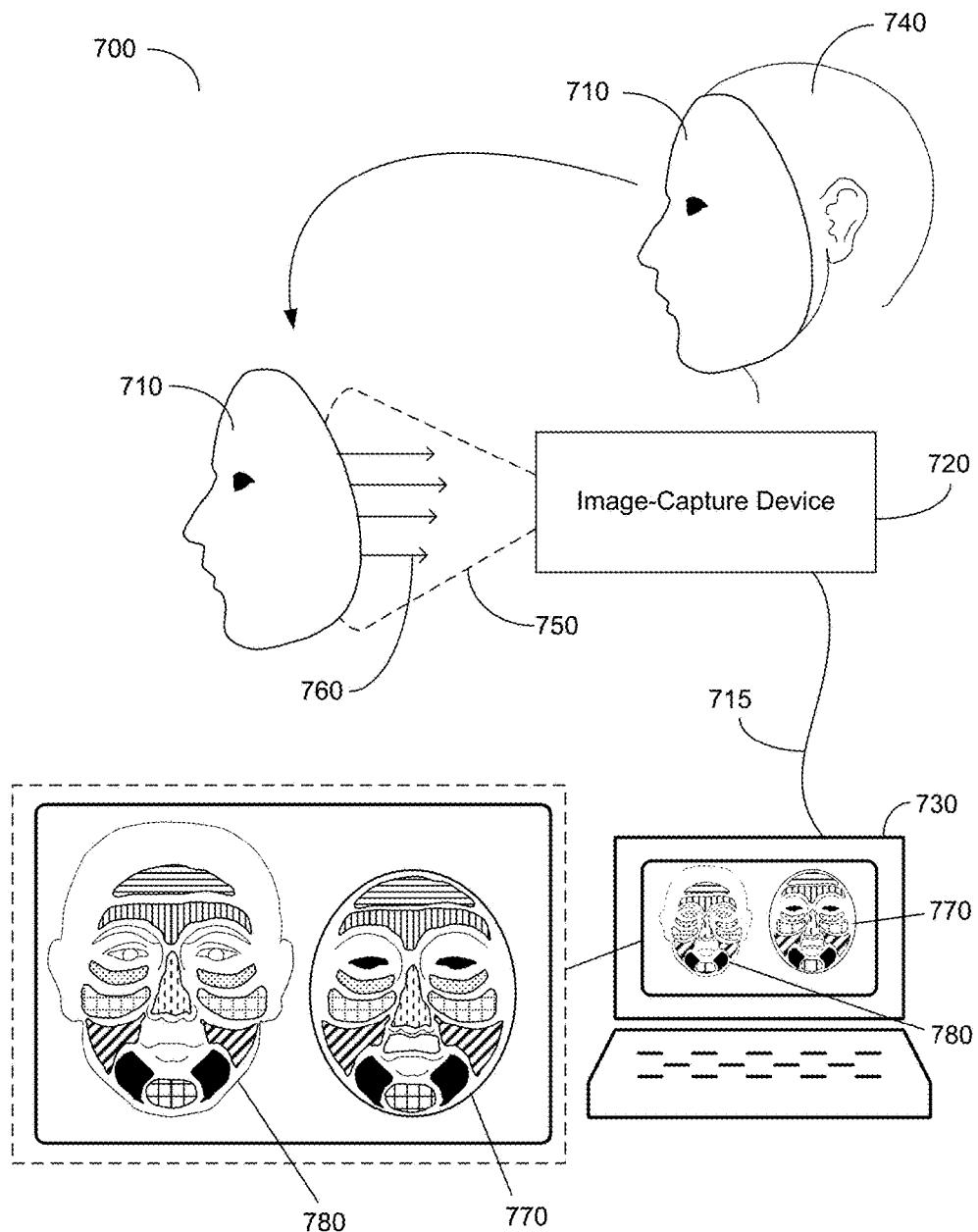

1300
Receiving a digital output from an image-capture device, the digital output including information associated with at least one property and a spatial distribution of one or more signals emitted from one or more of a plurality of signal-generating complexes associated with an inner surface of a skin-covering material, the one or more signals emitted or reflected from the one or more of the plurality of signal-generating complexes in response to at least one type of microbe

---

1310
Identifying the at least one type of microbe by comparing the information associated with the at least one property of the one or more signals emitted from the one or more of the plurality of signal-generating complexes with a database of signal properties of reference signal-generating complexes

---

1320
Generating a digital spatial profile of the at least one type of microbe based on the spatial distribution of the one or more signals emitted from the one or more of the plurality of signal-generating complexes in response to the at least one type of microbe

---

1330
Reporting at a user an identification and the digital spatial profile of the identified at least one type of microbe

1300
Receiving a digital output from an image-capture device, the digital output including information associated with at least one property and a spatial distribution of one or more signals emitted from one or more of a plurality of signal-generating complexes associated with an inner surface of a skin-covering material, the one or more signals emitted from the one or more of the plurality of signal-generating complexes in response to at least one type of microbe > 1400 From at least one digital camera > 1410 From at least one scanning device

---

1310
Identifying the at least one type of microbe by comparing the information associated with the at least one property of the one or more signals emitted from the one or more of the plurality of signal-generating complexes with a database of signal properties of reference signal-generating complexes

| 1420 Comparing at least one of an optical property | 1425 Comparing at least one of a fluorescence property | 1430 Comparing at least one of an infrared spectral property |
| 1435 Comparing at least one of an acoustic property | 1440 Comparing at least one of a magnetic property | 1445 Comparing at least one of an electromagnetic property |
| 1450 Comparing at least one of an electrical property | 1455 Comparing at least one of a wavelength | 1460 Comparing at least one of a frequency |

> 1465 Comparing at least one of an amplitude

---

1320
Generating a digital spatial profile of the at least one type of microbe based on the spatial distribution of the one or more signals emitted from the one or more of the plurality of signal-generating complexes in response to the at least one type of microbe

---

1330
Reporting at a user an identification and the digital spatial profile of the identified at least one type of microbe

---

> 1470
> Generating a recommended treatment regimen based on the identification and the digital spatial profile of the identified at least one type of microbe; and reporting to the user the recommended treatment regimen

1300
Receiving a digital output from an image-capture device, the digital output including information associated with at least one property and a spatial distribution of one or more signals emitted from one or more of a plurality of signal-generating complexes associated with an inner surface of a skin-covering material, the one or more signals emitted from the one or more of the plurality of signal-generating complexes in response to at least one type of microbe

1310
Identifying the at least one type of microbe by comparing the information associated with the at least one property of the one or more signals emitted from the one or more of the plurality of signal-generating complexes with a database of signal properties of reference signal-generating complexes

1320
Generating a digital spatial profile of the at least one type of microbe based on the spatial distribution of the one or more signals emitted from the one or more of the plurality of signal-generating complexes in response to the at least one type of microbe

1330
Reporting at a user an identification and the digital spatial profile of the identified at least one type of microbe

1500 Generating a digital alignment of the digital spatial profile of the identified at least one type of microbe with a digital image of a skin surface of an individual covered by the inner surface of the skin-covering material; generating a personalized microbe profile for the individual from the generated digital alignment, the personalized microbe profile including the identification and a spatial profile of the identified at least one type of microbe on the skin surface of the individual; and reporting to the user the personalized microbe profile

| 1510 Providing a visual representation of the personalized microbe profile on a display | 1520 Providing a printout of the personalized microbe profile | 1530 Exporting the personalized microbe profile to a computing device |

1540 Generating a recommended treatment regimen based on the personalized microbe profile, and reporting the recommended treatment regimen to the user

1550 Comparing the personalized microbe profile with a reference microbe profile, generating a recommended treatment regimen for the individual based on the comparison, and reporting the recommended treatment regimen to the user

| 1560 Comparing with a reference microbe profile generated for the individual at a previous point in time | 1570 Comparing with a reference microbe profile generated for one or more other individuals |

Fig. 16

1600 Receiving a first digital output from an image-capture device, the first digital output including information associated with at least one property and a spatial distribution of a first set of one or more signals emitted at a first time point from at least one of a plurality of signal-generating complexes associated with an inner surface of a first skin-covering material 1610 Receiving a second digital output from an image-capture device, the second digital output including information associated with at least one property and a spatial distribution of a second set of one or more signals emitted at a second time point from at least one of a plurality of signal-generating complexes associated with an inner surface of a second skin-covering material 1620 Comparing the first digital output with the second digital output 1630 Generating a recommended treatment regimen based on the comparison of the first digital output with the second digital output 1640 Reporting the recommended treatment regimen to a user

Fig. 17

> 1700 Applying a skin-covering material to a skin surface of an individual, the skin-covering material including an inner surface and an outer surface, the inner surface substantially conforming in shape to a topography of the skin surface of the individual and including attached thereto a plurality of signal-generating complexes, one or more of the plurality of signal-generating complexes configured to emit one or more signals in response to at least one type of microbe > 1710 Removing the skin-covering material from the skin surface of the individual > 1720 Capturing at least one image of the inner surface of the skin-covering material with an image-capture device, the at least one image including one or more signals emitted from the one or more of the plurality of signal-generating complexes in response to the at least one type of microbe and transforming the captured at least one image into a digital output including information associated with at least one property and a spatial distribution of the imaged one or more signals > 1730 Receiving the digital output from the image-capture device, the digital output including information associated with the at least one property and the spatial distribution of the imaged one or more signals emitted from the one or more of the plurality of signal-generating complexes in response to the at least one type of microbe > 1740 Identifying the at least one type of microbe by comparing the information associated with the at least one property of the imaged one or more signals emitted from the one or more of the plurality of signal-generating complexes with a database of signal properties of reference signal-generating complexes > 1750 Generating a digital spatial profile of the at least one type of microbe based on the spatial distribution of the imaged one or more signals emitted from the one or more of the plurality of signal-generating complexes > 1760 Reporting to a user an identification and spatial profile of the identified at least one type of microbe

Fig. 18

1800 Applying the plurality of signal-generating complexes to the inner surface of the skin-covering material prior to applying the skin-covering material to the skin surface of the individual 1700 Applying a skin-covering material to a skin surface of an individual, the skin-covering material including an inner surface and an outer surface, the inner surface substantially conforming in shape to a topography of the skin surface of the individual and including attached thereto a plurality of signal-generating complexes, one or more of the plurality of signal-generating complexes configured to emit one or more signals in response to at least one type of microbe 1710 Removing the skin-covering material from the skin surface of the individual 1720 Capturing at least one image of the inner surface of the skin-covering material with an image-capture device, the at least one image including one or more signals emitted from the one or more of the plurality of signal-generating complexes in response to the at least one type of microbe and transforming the captured at least one image into a digital output including information associated with at least one property and a spatial distribution of the imaged one or more signals 1810 Separating the skin-covering material into one or more pieces along one or more tearable lines of perforation; and capturing at least one image of the inner surface of at least one of the one or more pieces of the skin-covering material 1730 Receiving the digital output from the image-capture device, the digital output including information associated with the at least one property and the spatial distribution of the imaged one or more signals emitted from the one or more of the plurality of signal-generating complexes in response to the at least on type of microbe 1740 Identifying the at least one type of microbe by comparing the information associated with the at least one property of the imaged one or more signals emitted from the one or more of the plurality of signal-generating complexes with a database of signal properties of reference signal-generating complexes 1750 Generating a digital spatial profile of the at least one type of microbe based on the spatial distribution of the imaged one or more signals emitted from the one or more of the plurality of signal-generating complexes 1760 Reporting to a user an identification and spatial profile of the identified at least one type of microbe

Fig. 20

| |
|---|
| 1700 Applying a skin-covering material to a skin surface of an individual, the skin-covering material including an inner surface and an outer surface, the inner surface substantially conforming in shape to a topography of the skin surface of the individual and including attached thereto a plurality of signal-generating complexes, one or more of the plurality of signal-generating complexes configured to emit one or more signals in response to at least one type of microbe |
| 1710 Removing the skin-covering material from the skin surface of the individual |
| 1720 Capturing at least one image of the inner surface of the skin-covering material with an image-capture device, the at least one image including one or more signals emitted from the one or more of the plurality of signal-generating complexes in response to the at least one type of microbe and transforming the captured at least one image into a digital output including information associated with at least one property and a spatial distribution of the imaged one or more signals |
| 1730 Receiving the digital output from the image-capture device, the digital output including information associated with the at least one property and the spatial distribution of the imaged one or more signals emitted from the one or more of the plurality of signal-generating complexes in response to the at least on type of microbe |
| 1740 Identifying the at least one type of microbe by comparing the information associated with the at least one property of the imaged one or more signals emitted from the one or more of the plurality of signal-generating complexes with a database of signal properties of reference signal-generating complexes |
| 1750 Generating a digital spatial profile of the at least one type of microbe based on the spatial distribution of the imaged one or more signals emitted from the one or more of the plurality of signal-generating complexes |
| 2000 Generating a recommended treatment regimen based on the identification and the digital spatial profile of the at least one type of microbe; and reporting the recommended treatment regimen to the user |
| 2010 Generating a digital alignment of the digital spatial profile of the at least one type of microbe with a digital image of the skin surface of the individual covered by the inner surface of the skin-covering material; creating a personalized microbe profile from the digital alignment, the personalized microbe profile including the identification and the spatial profile of the identified at least one type of microbe on the skin surface of the individual; generating a recommended treatment regimen based on a comparison of the personalized microbe profile with at least one reference microbe profile; and reporting to the user at least one of the personalized microbe profile or the recommended treatment regimen |
| 1760 Reporting to a user an identification and spatial profile of the identified at least one type of microbe |

Fig. 23

2300 An article of manufacture

2310 Non-transitory machine readable media bearing one or more instructions for assessing mcirobiota of skin, the one or more instructions including:

2320 One or more instructions for receiving a digital output from an image-capture device, the digital output including information associated with at least one property and a spatial distribution of one or more signals emitted from one or more of a plurality of signal-generating complexes associated with an inner surface of a skin-covering material, the one or more signals emitted from the one or more of the plurality of signal-generating complexes in response to at least one type of microbe 2330 One or more instructions for comparing the information associated with at least one property of the one or more signals emitted from the one or more of the plurality of signal-generating complexes with a database of signal properties of reference signal-generating complexes 2340 One or more instructions for generating a microbe profile including the at least one property and the spatial distribution of the one or more signals emitted from the one or more of the plurality of signal-generating complexes 2350 One or more instructions for generating a recommended treatment regimen for an individual based on a comparison of the microbe profile with a reference microbe profile 2360 One or more instructions for reporting to a user at least one of the microbe profile or the recommended treatment regimen

SYSTEMS, METHODS, AND DEVICES FOR ASSESSING MICROBIOTA OF SKIN

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

Priority Applications:

The present application constitutes a continuation of U.S. patent application Ser. No. 15/366,811, entitled SYSTEMS, METHODS, AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 1 Dec. 2016, which is currently co-pending or is an application of which a currently co-pending application is entitled to the benefit of the filing date, and which is a continuation of U.S. patent application Ser. No. 13/975,079, entitled SYSTEMS, METHODS AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 23 Aug. 2013.

Related Applications:

U.S. patent application Ser. No. 13/975,055, now U.S. Pat. No. 9,390,312, entitled SYSTEMS, METHODS, AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 23 Aug. 2013, is related to the present application.

U.S. patent application Ser. No. 13/975,067, now U.S. Pat. No. 9,456,777, entitled SYSTEMS, METHODS, AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 23 Aug. 2013, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, a device for assessing microbiota of skin includes, but is not limited to, a skin-covering material including an inner surface and an outer surface, the inner surface substantially conforming in shape to a topography of a skin surface of an individual and including attached thereto a plurality of signal-generating complexes, each of the plurality of signal-generating complexes including at least one signal-generating element and at least one specific microbe-binding element. In addition to the foregoing, other device aspects are described in the claims, drawings, and text forming a part of the present disclosure.

In an aspect, a system for assessing microbiota of skin includes, but is not limited to, a skin-covering material including an inner surface and an outer surface, the inner surface of the skin-covering material substantially conforming in shape to a topography of a skin surface of an individual and including attached thereto a plurality of signal-generating complexes, one or more of the plurality of signal-generating complexes configured to emit one or more signals in response to at least one type of microbe; an image-capture device including circuitry to capture at least one image of the inner surface of the skin-covering material, the at least one image including one or more signals emitted from one or more of the plurality of signal-generating complexes in response to the at least one type of microbe and to transform the captured at least one image into a digital output including information associated with at least one property and a spatial distribution of the imaged one or more signals; and a computing device including a processor, the computing device operably coupled to the image-capture device and including circuitry configured to receive the digital output from the image-capture device including the information associated with the at least one property and the spatial distribution of imaged one or more signals emitted from the one or more of the plurality of signal-generating complexes in response to the at least one type of microbe; compare the properties of the imaged one or more signals emitted from the one or more of the plurality of signal-generating complexes in response to the at least one type of microbe with a database of emitted signals of reference signal-generating complexes; and generate a digital spatial profile of the at least one type of microbe based on the spatial distribution of the imaged one or more signals emitted from the one or more of the plurality of signal-generating complexes in response to the at least one type of microbe. In addition to the foregoing, other system aspects are described in the claims, drawings, and text forming a part of the present disclosure.

In an aspect, a method for assessing microbiota of skin includes, but is not limited to, receiving a digital output from an image-capture device, the digital output including information associated with at least one property and a spatial distribution of one or more signals emitted from one or more of a plurality of signal-generating complexes associated with the inner surface of a skin-covering material, the one or more signals emitted from the one or more of the plurality of signal-generating complexes in response to at least one type of microbe; identifying the at least one type of microbe by comparing the information associated with the at least one property of the one or more signals emitted from the one or more of the plurality of signal-generating complexes with a database of single properties of reference signal-generating complexes; generating a digital spatial profile of the at least one type of microbe based on the spatial distribution of the one or more signals emitted from the one or more of the plurality of signal-generating complexes; and reporting to a user an identification and the digital spatial profile of the identified at least one type of microbe. In addition to the foregoing, other method aspects are described in the claims, drawings, and text forming a part of the present disclosure.

In an aspect, a method for assessing microbiota of skin includes, but is not limited to, receiving a first digital output from an image-capture device, the first digital output including information associated with at least one property and a spatial distribution of a first set of one or more signals emitted at a first time point from at least one of a plurality of signal-generating complexes associated with an inner surface of a first skin-covering material; receiving a second digital output from the image-capture device, the second digital output including information associated with at least one property and a spatial distribution of a second set of one or more signals emitted at a second time point from at least one of a plurality of signal-generating complexes associated with an inner surface of a second skin-covering material; comparing the first digital output with the second digital output; generating a recommended treatment regimen based on the comparison of the first digital output and the second digital output; and reporting the recommended treatment regimen to a user. In addition to the foregoing, other method aspects are described in the claims, drawings, and text forming a part of the present disclosure.

In an aspect, a method for assessing microbiota of skin includes, but is not limited to, applying a skin-covering material to a skin surface of an individual, the skin-covering material including an inner surface and an outer surface, the inner surface substantially conforming in shape to a topography of the skin surface of the individual and including attached thereto a plurality of signal-generating complexes, one or more of the plurality of signal-generating complexes configured to emit one or more signals in response to at least one type of microbe; removing the skin-covering material from the skin surface of the individual; capturing at least one image of the inner surface of the skin-covering material with an image-capture device, the at least one image including one or more signals emitted from the one or more of the plurality of signal-generating complexes in response to the at least one type of microbe and transforming the captured at least one image into a digital output including information associated with at least one property and a spatial distribution of the imaged one or more signals; receiving the digital output from the image-capture device, the digital output including the information associated with the at least one property and the spatial distribution of the imaged one or more signals emitted from the one or more of the plurality of signal-generating complexes in response to the at least on type of microbe; identifying the at least one type of microbe by comparing the information associated with the at least one property of the imaged one or more signals emitted from the one or more of the plurality of signal-generating complexes with a database of signal properties of reference signal-generating complexes; generating a digital spatial profile of the at least one type of microbe based on the spatial distribution of the imaged one or more signals emitted from the one or more of the plurality of signal-generating complexes; and reporting to a user an identification and the digital spatial profile of the identified at least one type of microbe. In addition to the foregoing, addition method aspects are described in the claims, drawings, and text forming a part of the present disclosure.

In an aspect, an article of manufacture includes, but is not limited to: non-transitory machine readable media bearing one or more instructions for assessing microbiota of skin, the one or more instructions including one or more instructions for receiving a digital output from an image-capture device, the digital output including information associated with at least one property and a spatial distribution of one or more signals emitted from one or more of a plurality of signal-generating complexes associated with an inner surface of a skin-covering material, the one or more signals emitted from the one or more of the plurality of signal-generating complexes in response to at least one type of microbe; one or more instructions for comparing the information associated with at least one property of the one or more signals emitted from the one or more of a plurality of signal-generating complexes with a database of signal properties of reference signal-generating complexes; one or more instructions for generating a microbe profile including the at least one property and the spatial distribution of the one or more signals emitted from the one or more of the plurality of signal-generating complexes; instructions for generating a recommended treatment regimen for an individual based on a comparison of the microbe profile with a reference microbe profile; and one or more instructions for reporting to a user at least one of the microbe profile or the recommended treatment regimen. In addition to the foregoing, other aspects of the article of manufacture are described in the claims, drawings, and text forming a part of the present disclosure.

In an aspect, a system for assessing microbiota of skin includes, but is not limited to, an image-capture device including circuitry to capture at least one image of an inner surface of a skin-covering material, the at least one image including one or more signals emitted from one or more of a plurality of signal-generating complexes associated with the inner-surface of the skin-covering material in response to at least one type of microbe and to transform the captured at least one image into a digital output including information associated with at least one property and a spatial distribution of the imaged one or more signals; a computing device including a processor, the computing device operably coupled to the image-capture device; and non-transitory machine readable media readable by the computing device and bearing one or more instructions for assessing microbiota of skin, the one or more instructions including one or more instructions for receiving the digital output from the image-capture device, the digital output including the information associated with the at least one property and the spatial distribution of the imaged one or more signals emitted from the one or more of a plurality of signal-generating complexes in response to the at least one type of microbe; one or more instructions for comparing the information associated with the at least one property of the imaged one or more signals emitted from the one or more of a plurality of signal-generating complexes with a database of signal properties of reference signal-generating complexes; one or more instructions for generating a microbe profile including the at least one property and the spatial distribution of the imaged one or more signals emitted from the one or more of the plurality of signal-generating complexes; instructions for generating a recommended treatment regimen for an individual based on a comparison of the microbe profile with a reference microbe profile; and one or more instructions for reporting to a user at least one of the microbe profile or the recommended treatment regimen. In addition to the foregoing, other aspects of the article of manufacture are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 includes FIGS. 1A and 1B illustrating an embodiment of a skin-covering material.

FIG. 2 includes FIGS. 2A-2C illustrating an embodiment of a skin-covering material.

FIG. 5 includes FIGS. 5A-5C illustrating an embodiment of a skin-covering material.

FIG. 6 includes FIGS. 6A-6C showing an embodiment of a skin-covering material.

FIG. 7 is a schematic of a system including a skin-covering material for assessing microbiota of skin.

FIG. 12 includes FIGS. 12A-12C illustrating an embodiment of a system including a skin-covering material.

FIG. 13 is a flowchart of a method for assessing microbiota of skin.

FIG. 14 is a flowchart illustrating further aspects of a method such as shown in FIG. 13.

FIG. 15 is a flowchart showing further aspects of a method such as depicted in FIG. 13.

FIG. 16 is a flowchart of a method for assessing microbiota of skin.

FIG. 17 is a flowchart of a method for assessing microbiota of skin.

FIG. 18 is a flowchart illustrating further aspects of a method such as shown in FIG. 17.

FIG. 19 includes FIGS. 19A-19D showing an embodiment of a method such as shown in FIG. 17.

FIG. 20 is a flowchart illustrating further aspects of a method such as shown in FIG. 17.

FIG. 21 includes FIGS. 21A-21C showing an embodiment of a skin-covering material.

FIG. 23 illustrates aspects of an article of manufacture for assessing microbiota of skin.

DETAILED DESCRIPTION

Figure 1A:
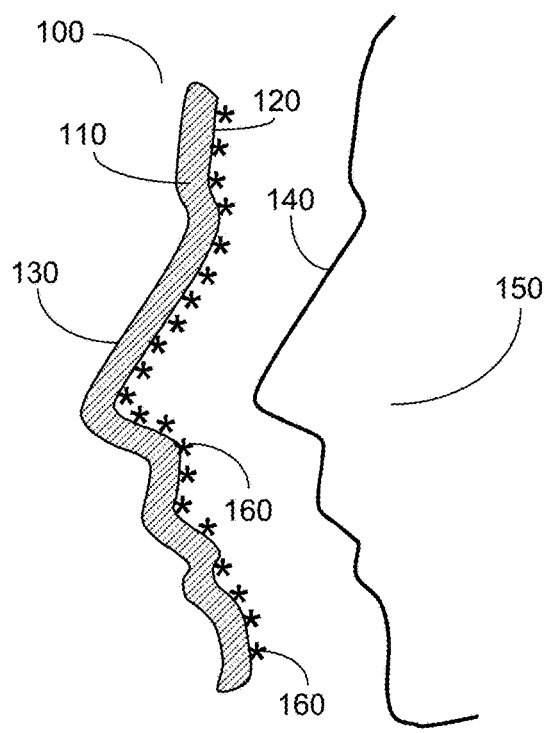
FIG. 1A is a cross-section through a skin-covering material including a plurality of signal-generating complexes.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The skin, the largest organ of the mammalian body, is inhabited by a diverse array of microbes, including bacteria, fungi, viruses, parasites, archaea, or small arthropods (e.g., mites). Variations in regional properties of the skin, e.g., variations in pH, moisture, pores, texture, and the like, from one body location to another contribute to the spatial diversity of skin-associated microbes. Similarly, the type of microbes and/or spatial distribution of one or more microbes on the skin surface may change in response to cleaning of the skin surface, application of anti-microbial agents, application of irritating agents, e.g., make-up, lotion, sun screen, or exposure to irritating conditions, e.g., diet, disease, wind, or sun exposure. In some instances, skin-resident microbes on the skin surface, e.g., commensal bacteria, provide a benefit to the individual. For example, *Staphylococcus epidermidis* has been demonstrated to modulate the host innate immune response, inhibiting other bacterial pathogens such as *Staphylococcus aureus* and Group A *Streptococcus*. See, e.g., Grice & Segre (2011) Nat. Rev. Microbiol. 9:244-53, which is incorporated herein by reference. In some instances, skin-resident microbes have been linked to pathological conditions including acne, psoriasis, and atopic dermatitis. See, e.g., Cho & Blaser (2012) *Nat. Rev. Genet.* 13:260-270, which is incorporated herein by reference. In general, understanding the identity and spatial distribution of skin-resident microbes on the skin under normal and/or pathological conditions can contribute to decisions regarding therapeutic, preventative, and/or cosmetic treatments. Described here are embodiments of systems, methods, and devices for assessing the microbiota of skin.

Figure 1B:
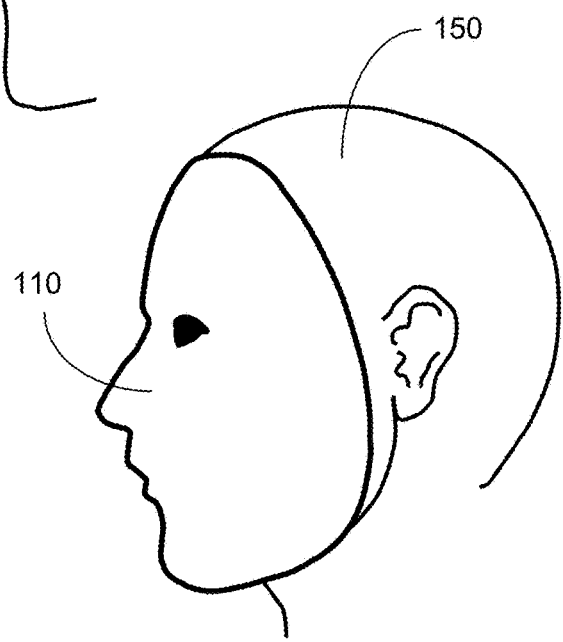
FIG. 1B illustrates a skin-covering material on an individual.

FIGS. 1A and 1B illustrate a device 100 for assessing microbiota of skin. FIG. 1A is a schematic cross-section through device 100. Device 100 includes skin-covering material 110 with inner surface 120 and outer surface 130. Inner surface 120 substantially conforms in shape to a topography of skin surface 140 of individual 150. Inner surface 120 further includes attached thereto a plurality of signal-generating complexes 160. Each of the plurality of signal-generating complexes 160 includes at least one signal-generating element and at least one specific microbe-binding element.

In an aspect, at least one of the plurality of signal-generating complexes 160 is configured to emit one or more signals in response to at least one type of microbe. In an aspect, the plurality of signal-generating complexes associated with the inner surface of the skin-covering material come into contact with at least one type of microbe when the skin-covering material is placed on the skin surface of an individual. In an aspect, the at least one type of microbe can include at least one type of mutualistic microbe, commensal microbe, or pathogenic microbe. In an aspect, the at least one type of microbe includes at least one type of skin-associated or skin-resident bacteria. The at least one type of microbe includes at least one type of bacteria, fungus, virus, parasite, archaea, or small arthropod (e.g., mites). In an aspect, the at least one type of microbe includes at least one type of mutualistic microbe, commensal microbe, or pathogenic microbe. In an aspect, the at least one type of microbe captured by the skin-covering material can include at least one type of skin-resident microbe. Non-limiting examples of skin-associated or skin-resident bacteria include proteobacteria, e.g., *Pseudomonas* sp., *Janthinobacterium* sp, *Alphaproteobacteria*, other gammaproteobacteria, and betaproteobacteria; *Actinobacteria*, e.g., *Kocuria* sp., *Propionibacteria* sp.; *Firmicutes*, e.g., *Staphylococcus epidermidis*; *Bacteroidetes*; and *Spirochaetes*. See, e.g., Grice et al. (2008) *Genome Res.* 18:1043-1050; Grice & Segre (2011) *Nat. Rev. Microbiol.* 9:244-253, which are incorporated herein by reference. Non-limiting examples of fungi, including skin-resident or associated types of fungi, include dermatophtyes, e.g., trichophyton, microsporum, epidermophyton, tinea capitis. Other skin associated fungi include but are not limited to yeast, *Candida*, e.g., *Candida albicans*; and *Malassezia* spp (e.g., *M. dermatis, M. furfur, M. globosa*, and *M. restricta*). See, e.g., Gaitanis et al. (2012) *Clin. Microbiol. Rev.* 25:106-141, which is incorporated herein by reference. Non-limiting examples of skin-associated or skin-resident viruses include herpes simplex virus type I (HSV-1), herpes zoster, Molluscum contagiosum, human papillomavirus (HPV), Coxsackie virus A16, and herpes gladiatorum. Non-limiting examples of other parasites resident or associated with a skin surface include skin-associated parasitic arthropods including parasitic mites, e.g., *Demodex* spp including *D. folliculorum* and *D. brevis*, and *Sarcoptes scabiei*, a skin parasite associated with scabies.

In an aspect, at least one of the plurality of signal-generating complexes is configured to emit one or more signals upon interaction with at least one type of microbe. In an aspect, the interaction with the at least one type of microbe is a binding interaction, in which the at least one type of microbe binds to a portion of the signal-generating complex and induces emission of a signal. In an aspect, the microbe may be physically attached to the signal-generating complex. In an aspect, a brief interaction between the microbe and the signal-generating complex may be sufficient to induce a signal. In an aspect, the interaction of the signal-generating complex with the at least one type of microbe is a chemical interaction, in which some component of the microbe, e.g., an excreted component, interacts with the signal-generating complex to induce emission of a signal.

FIG. 1B illustrates device 100 on the skin surface of individual 150. In this instance, the inner surface of device 100 substantially conforms to the topography of the face of individual 150, but may be configured for use on any of a number of skin surfaces of an individual. In an aspect, inner surface 120 of skin-covering material 110 substantially conforms in shape to a topography of a skin surface of an individual. The topography of the skin surface can include both the micro-topography, e.g., the texture and/or pattern of the skin surface, and the macro-topography, e.g., anatomical features such as nose, lips, cheeks, large wrinkles, joints, and the like. The skin surface can include any of a number of regions of the body including, but not limited to the facial region, torso region, abdominal region, head region, neck region, upper extremity, lower extremity, buttocks, or any other body region for which analysis of the spatial distribution of microbiota of the individual is desired. In an aspect, skin-covering material substantially conforms in shape to a topography of one or more surfaces of a mouth region of an individual. The one or more surfaces of the mouth region of the individual can include one or more of an oral mucosa, a tooth, gingiva, tongue, and/or palate. In an aspect, inner surface 120 of skin-covering material 110 may be configured to substantially conform in shape to the topography of the skin surface of all or part of the individual's face to form, for example, a mask-like covering. In an aspect, the skin-covering material is personalized to substantially conform to the topography of the skin surface of a specific individual. In an aspect, the skin-covering material is non-planar, e.g., substantially conforming in shape to a topography of a skin surface that includes non-planar contours, e.g., the features of a face.

In an aspect, skin-covering material 110 includes a pre-formed skin-covering. In an aspect, the pre-formed skin-covering material includes a semi-rigid pre-formed skin-covering material. For example, the skin-covering material can include a thin flexible substrate that conforms to the topography of the skin surface of the individual. For example, the skin-covering material can include a flexible strip, a wrap, a band, or the like that conforms to the curvature of a skin surface, e.g., the curvature of the face or arm pit or around an extremity, making uniform contact with the skin so as to uniformly capture representative microbes from all portions of the covered skin. For example, the semi-rigid pre-formed skin-covering material may include a specially coated strip of bendable material, e.g., a coated sheet of Mylar or a treated piece of fabric, that when applied to a skin surface substantially conforms in shape to the topography of the skin surface, e.g., wraps around the contours of a body part. In an aspect, the skin-covering material includes a flexible strip similar to a wound covering but with a region configured to capture one or more skin-resident microbes.

In an aspect, the pre-formed skin-covering material includes a rigid pre-formed skin-covering material. For example, the rigid pre-formed skin-covering material can include a rigid thin plastic substrate that has been designed and manufactured, e.g., by three-dimensional printing, to substantially conform in shape to the topography of an individual's skin surface. For example, the rigid pre-formed skin-covering material can include a mask-like structure that substantially conforms in shape to the topography of the skin surface of an individual's face. In general, the pre-formed skin-covering material is configured to substantially conform to the topography of the skin surface of the individual to achieve uniform contact of the microbe-capture region on the inner surface of the skin-covering material with the underlying skin surface.

In an aspect, the pre-formed skin-covering material includes a thin substrate that is non-planar and is either flexible or rigid. For example, the pre-formed skin-covering material may include a structure that mirrors the contours and/or topography of a specific region of the skin. For example, the pre-formed skin-covering material may have a non-planar structure that mirrors the contours and/or topography of an individual's face and as such when placed on the surface of the skin makes uniform contact with substantially all of the overlapping portions. For example, the pre-formed skin-covering material can include a non-planar, flexible latex-like thin substrate that substantially conforms to the topography of the skin surface of the individual. For example, the pre-formed skin-covering material can include a non-planar, hard plastic-like, thin substrate that substantially conforms to the topography of the skin surface of the individual. In an aspect, the rigid or semi-rigid pre-formed skin-covering material is formed using three-dimensional printing to substantially conform to a digital rendering of a skin surface topography of an individual. In an aspect, the rigid or semi-rigid pre-formed skin-covering material is generic, substantially conforming to the topography of the skin surface of any of a number of individuals.

In an aspect, the pre-formed skin-covering material may cause the topography of the skin to conform to the topography of the skin-covering material, e.g., when a pre-formed skin-covering material is pressed upon a conformable body part, e.g., a body part including ample soft tissue. For example, a pre-formed rigid skin-covering material, e.g., a mask, may be pressed against an individual's cheek, buttocks, or upper thigh to achieve uniform contact of the pre-formed skin-covering material with the underlying skin surface.

The pre-formed skin-covering material can include any of a number of materials capable of being shaped, molded or printed to form the pre-formed skin-covering material. Non-limiting examples of shapeable, moldable or printable materials include acrylic, nylon, plastic, ceramic, resin, rubber, epoxy, thermoplastic, polymer, photopolymer, polyurethane, gel, hydrogel, latex, or silicone. Additional non-limiting examples of shapeable, moldable or printable materials for use in forming the skin covering include: metals such as titanium/titanium alloys, TiNi (shape memory/super elastic), aluminum oxide, platinum/platinum alloys, stainless steels, pyrolytic carbon, silver or glassy carbon; polymers such as polyurethanes, polycarbonates, silicone elastomers, polyolefins including polyethylenes or polypropylenes, polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, ethylene tetrafluoroethylene copolymer (ETFE), acrylonitrile butadiene ethylene, polyamide, polyimide, styrene acrylonitrile, and the like; minerals or ceramics such as hydroxapatite; organic materials such as wood, cellulose, or compressed carbon; and other materials such as glass, or the like.

The pre-formed skin-covering material may be formed from shapeable, moldable, or printable materials by a variety of manufacturing methods. In some embodiments, the pre-formed skin-covering material is generated from a mold made of a skin surface of the individual. For example, a mold of a skin surface of an individual can be generated by covering the skin surface, e.g., an individual's face, with a material that hardens to conform in shape to a topography of the skin surface. For example, alginate may be used in combination with plaster bandages to create a mold of a skin surface of an individual, e.g., the individual's face. In some embodiments, the mold itself can be used as the pre-formed skin-covering material. Non-limiting examples of materials that can be used for generating a mold of a skin surface of an individual include modeling clay, plaster, alginate, or combinations thereof. In some embodiments, the mold can be a reusable template for forming one or more pre-formed skin-covering material with a material, e.g., latex, that is poured or spread into the mold, hardened, and removed from the mold.

In an aspect, the pre-formed skin-covering material is personalized to substantially conform to the topography of the skin surface of the individual. For example, a digital three-dimensional representation of the skin surface of the individual may be used to digitally render a pre-formed skin-covering, the latter of which is used as a template for manufacturing the pre-formed skin-covering using a three-dimensional printer. One or more digital images of the skin surface of the individual for use in generating a digital three-dimensional representation of the skin surface can be acquired from one or more of a digital camera or scanning device. For example, two video cameras, slightly apart, can be used to image the same portion of skin surface of the individual in a process termed stereophotogrammetry. For example, a single camera can be used to take multiple images under different lighting conditions or from different positions. In an aspect, the topography of the skin surface of an individual can be acquired in a point-cloud format using a three-dimensional sensing system consisting of two or more digital cameras and one or more projectors connected to a personal computer. The camera position and shutter can be adjusted to the body region, which is exposed to structured light, allowing for optical representation of the surface by a cloud of up to 300,000 points in three-dimensional coordinates (see, e.g., Feng et al., *Br. J. Oral Maxillofac. Surg.* (2010) 48:105-109, which is incorporated herein by reference). In some embodiments, the combination of stereophotogrammetry and 3D laser scanner techniques can be combined to generate a three-dimensional model of the skin surface of an individual (see, e.g., Majid, et al. *International*

*Archives of the Photogrammetry, Remote Sensing and Spatial Information Science.* Vol. XXXVII. Part B5. (2008) 805-811; Markiewicz & Bell, *Facial Plast. Surg. Clin. N. Am.* (2011) 19:655-682; van Heerbeek et al., *Rhinology* (2009) 47:121-125, which are incorporated herein by reference). Scanners for scanning head, face and/or whole body are commercially available (from, e.g., Cyberware, Monterey Calif.; Accurex Measurement Inc., Swathmore, Pa.; 3dMD Atlanta, Ga.; Konica/Minolta, Ramsey, N.J.)

In an aspect, surface scanning software can be used to import individual points of the skin surface, e.g., of the face, and then combine them in the X, Y, and Z axes to render a three-dimensional representation of the topography of the skin surface. In some embodiments, the one or more images of the skin surface may include point clouds of data that are reconstructed using one or more three-dimensional modeling algorithms to form a digitally rendered model of the skin-covering material. One or more modeling programs can be used for this purpose. Non-limiting examples of types of modeling programs include polygonal mesh three-dimensional modeling programs, non-uniform rational basis spline (NURBS) surface modeling programs, or editable feature-based computer aided design (CAD) modeling programs. In some embodiments, the data may be modeled using a first modeling approach, for example, a NURBS based modeling program and further refined using a second modeling approach, for example, a CAD-based modeling program. Numerous software programs are available for generating three-dimensional models from scanned images. For example, non-limiting examples of CAD/CAM software programs applicable to medical imaging include Amira (Visage Imaging GmbH, Berlin Germany); Analyze (AnalyzeDirect, Inc, Overland Park, Kans.); iNtellect Cranial Navigation System (Stryker, Freiburg, Germany); iPlan (BrainLab, Westchester, Ill.); Maxilim (Medicim, Bruges Belgium), Mimics, SurgiCase CMF, and SimPlant OMS (Materialise, Leuven, Belgium); Voxim (IVS Solutions, Chemnitz, Germany), 3dMD (Atlanta, Ga.); Alma3D (Alma IT Systems, Barcelona, Spain); and ImageJ (National Institutes of Health, Boston, Mass.) (see, e.g., Markiewicz & Bell, *Facial Plast. Surg. Clin. N. Am.* (2011) 19:655-682, which is incorporated herein by reference). Facial feature extraction can be acquired using one or more of an active shape model algorithm (see, e.g., Sun & Xie, 11$^{th}$ *IEEE International Conference on Communication Technology Proceedings*, (2008) pp. 661-664; Zheng & Yang *IEEE Proceedings of the Seventh International conference on Machine Learning and Cybernetics*, (2008) pp. 2841-2845, which are incorporated herein by reference). Other software packages capable of generating a digitally rendered model of the skin-covering material from one or more digital images of a skin surface of an individual can be used for this purpose. Additional approaches for generating three-dimensional models are described in Bernardini & Rushmeier *Computer Graphics Forum* (2002) 21:149-172, which is incorporated herein by reference.

In an aspect, information regarding the digitally rendered model of the pre-formed skin-covering material is sent to a manufacturing device which produces the pre-formed skin-covering material based on the received information. Non-limiting examples of methods for generating a three-dimensional structure from digitized information include stereolithography, laser sintering, fused deposition modeling, polyjet, three-dimensional printing, vacuum casting, reaction injection molding, or injection molding. Non-limiting examples of materials for generating a three-dimensional structure from digitized information include one or more of acrylic, nylon, plastic, ceramic, resin, rubber, epoxy, thermoplastic, photopolymer, polyurethane, latex or silicone. The type of material used for forming the pre-formed skin-covering material is dependent upon the method used to form the pre-formed skin-covering material and the desired properties, e.g., rigidity, transparency, and/or porosity, of the final product. Exemplary materials and methods for forming a pre-formed skin-covering material using stereolithography, laser scintering or three-dimensional printing as well as other methods for forming a pre-formed skin-covering material from the digitally rendered model of the pre-formed skin-covering material are described herein.

In an aspect, the pre-formed skin-covering material is formed using an additive manufacturing process. Additive manufacturing refers to a class of manufacturing process in which a three-dimensional object is built by adding layers of material upon one another. Other terms include layered manufacturing, direct digital manufacturing, or solid freeform fabrication. Non-limiting examples of additive manufacturing processes include liquid-based processes, e.g., stereolithography, jetted photopolymer, and ink jet printing; powder-based processes, e.g., selective laser sintering, direct metal laser sintering, and three-dimensional printing; and solid-based processes, e.g., laminated object manufacturing, fused deposition modeling.

In an aspect, the pre-formed skin-covering material is formed using a subtractive manufacturing process. Subtractive manufacturing refers to a class of manufacturing process in which a three-dimensional object is built by cutting away material. Non-limiting examples of subtractive manufacturing processes include machining, milling, turning, and drilling. Other non-limiting examples of manufacturing processes include molding, e.g., blow molding, injection molding, or thermoforming; and casting, e.g., centrifugal casting, die casting, sand casting, shell mold casting.

In an aspect, the pre-formed skin-covering material is generated using stereolithography using one or more optically curable photopolymers. Non-limiting examples of materials useful for stereolithography include poly(ethylene glycol) 1500, Accura 60, Accura 25, Accura Xtreme, Somos 9420, Somos 11122, Somos 18420, Somos DMX, Rigi2200, TuskXC2700T/Tusk2700 W, Nano5000, Flex45, Flex65, Flex70B, Flex 80, Protogen White. Other non-limiting examples of stereolithography include three-dimensional printing (3D printing), optical fabrication, photo-solidification, solid free-form fabrication, and solid imaging.

In an aspect, the pre-formed skin-covering material can be generated by 3D printing using an inkjet technology, e.g., PolyJet™ (from Objet Ltd) in which photopolymer materials are jetted in ultra-thin layers onto a build tray and cured layer by layer with UV light. Non-limiting examples of materials for use in generating a pre-formed skin-covering material using inkjet technology include Fullcure 720, VeroWhite, VeroBlack, VeroBlue, and VeroGray for rigid structures; Durus for semi-flexible structures; and Tango Elastomers for rubber-like structures. Other examples of 3D printers include ProJet and ZPrinters available from 3D Systems Corporation, Rock Hill S.C. and Freeform Pico, Asiga, Anaheim Hills, Calif.

In an aspect, the pre-formed skin-covering material is generated using selective laser sintering in which a high power laser, e.g., a carbon dioxide laser, is used to fuse small particles of plastic, metal, ceramic, glass powders, or combinations thereof into a mass that has a desired three-dimensional shape. Non-limiting examples of material for use in generating a pre-formed skin-covering material guide using laser sintering include polyamide, nylon, carbon, hydroxyapatite, glass filled polyamide, and alumide.

In an aspect, the pre-formed skin-covering material is generated using fused deposition modeling. Fused deposition modeling is an extrusion based three-dimensional modeling process using thermoplastic materials. Non-limiting examples of materials for use in fused deposition modeling include the thermoplastics ABS, ABS/F1, polycarbonate, and Ultem 9085. The uPrint SE from Stratasys (Eden Prairie, Minn.) or the Dimension Elite 3D printer from Dimension, Inc. (Eden Prairie, Minn.) are non-limiting examples of systems for fused deposition modeling with thermoplastics that might be appropriate for use in a medical clinic.

In an aspect, the pre-formed skin-covering material can be formed from a three-dimensional mold surface formed from the digitally rendered model of the pre-formed skin-covering material and using the three-dimensional mold surface with a moldable material to generate the pre-formed skin-covering material. For example, a three-dimensional mold surface of the individual's face can be fabricated from a thermoplastic material based on the digitally rendered model of the wearable injection guide. A moldable material, e.g., latex, can then be poured into or over the three-dimensional mold surface to generate the formed pre-formed skin-covering material. The three-dimensional mold surface can be used repeatedly to generate one or more pre-formed skin-covering material.

Figure 2A:
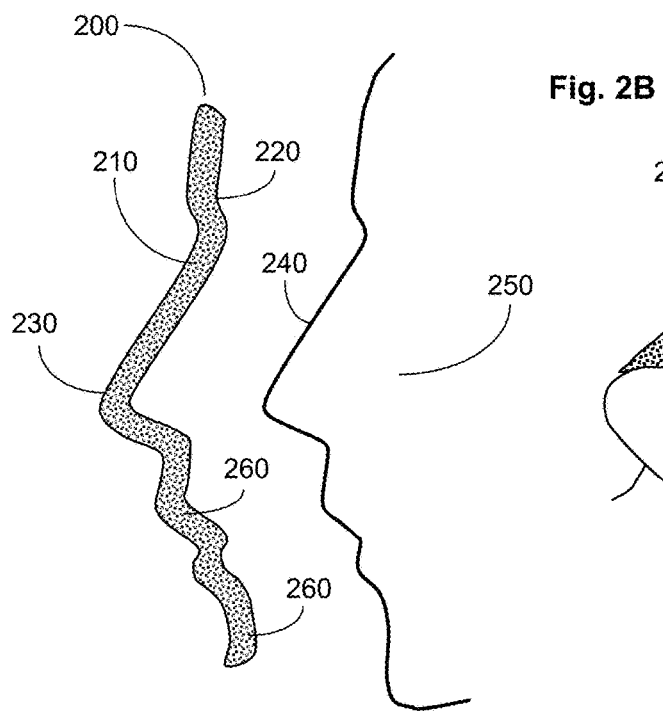
FIG. 2A is a cross-section through a peelable skin-covering material including a plurality of signal-generating elements.

In an aspect, the skin-covering material can include a peelable skin-covering material. FIG. 2 illustrates aspects of a device 200 including a peelable skin-covering material. FIG. 2A is a schematic cross-section through device 200. Device 200 includes peelable skin-covering material 210 which includes inner surface 220 and outer surface 230. Inner surface 220 substantially conforms in shape to the topography of skin surface 240 of individual 250. Inner surface 220 further includes attached there to a plurality of signal-generating complexes 260. In this non-limiting example, signal-generating complexes 260 are integrated throughout peelable skin-covering material 210.

In an aspect, peelable skin-covering material 210 includes a flexible solid, the flexible solid including the plurality of signal-generating complexes. The peelable skin-covering material can include any of a number of materials applied to the skin surface of the individual and subsequently peeled as a single piece from the surface of the skin. For example, the peelable skin-covering material can include one or more shapeable or moldable materials applied to the skin surface of an individual and peeled therefrom. In some embodiments, the shapeable or moldable material may harden over an elapsed period of time or by exposure to ambient air. In some embodiments, the shapeable or moldable material may be hardened in response to electromagnetic energy, e.g., light of a specific wavelength, or in response to elevated temperature.

Figure 2B:
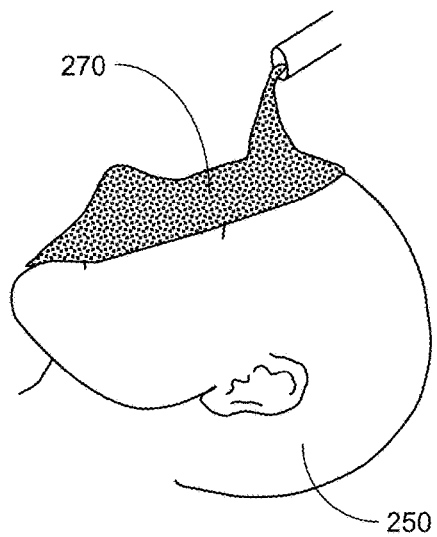
FIG. 2B illustrates a settable material of a skin surface.

In an aspect, peelable skin-covering material 210 includes a settable material, the settable material including a plurality of signal-generating complexes. FIG. 2B illustrates settable material 270 including plurality of signal-generating complexes applied to skin surface 240 of individual 250. Settable material 270 can include at least one material configured to undergo a phase change from a liquid or gelled phase to a flexible solid phase in response to an applied stimulus. For example, the settable material can include a material that is poured onto the skin surface of an individual. For example, the settable material can include a material that is spread onto the skin surface of an individual. Non-limiting examples of settable material include latex, gel, polymer, plastic, or resin. For example, the settable material can include one or more polymers, e.g., polyvinyl alcohol, polyacrylate, polymethacrylate and/or polyacrylamide. See, e.g., U.S. Pat. No. 5,747,022; U.S. Patent Application 2005/0019291, which are incorporated herein by reference. The applied stimulus can include one or more of exposure to air, a thermal stimulus, e.g., heat, or an electromagnetic stimulus, e.g., exposure to a specific wavelength or spectrum of light.

In an aspect, the peelable skin-covering material includes a shrink-wrap material that is applied to the skin surface as a thin sheet and conformed in shape to the topography of the skin surface using an applied stimulus, e.g., heat.

Figure 2C:
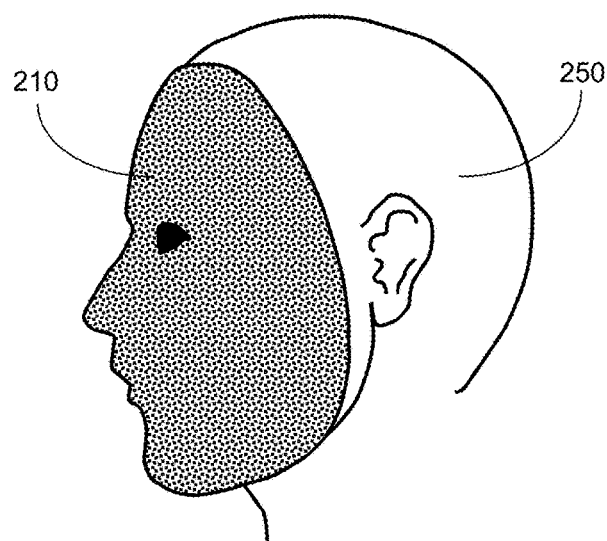
FIG. 2C illustrates a peelable skin-covering material on individual.

FIG. 2C shows peelable skin-covering material 210 on the skin surface of individual 250. In this non-limiting example, the inner surface of peelable skin-covering material 210 substantially conforms to the topography of the face of individual 250, but may be configured for use on any of a number of skin surfaces of an individual as described above herein.

In an aspect, the plurality of signal-generating complexes are incorporated into the skin-covering material. In an aspect, the plurality of signal-generating complexes are substantially uniformly distributed throughout the skin-covering material. For example, the plurality of signal-generating complexes may be uniformly dispersed in a liquid or gelled form during manufacture of the skin-covering material as shown, for example, in FIG. 2.

In an aspect, at least a portion of the plurality of signal-generating complexes are distributed along at least a portion of the inner surface of the skin-covering material. In an aspect, the plurality of signal-generating complexes are substantially uniformly distributed over at least a portion of the inner surface of the skin-covering material as shown, for example, in FIG. 1. In an aspect, at least a portion of the plurality of signal-generating complexes are functionally attached to the inner surface of the skin-covering material. In an aspect, at least one of the plurality of signal-generating complexes are covalently attached to the inner surface of the skin-covering material. In an aspect, at least one of the plurality of signal-generating complexes is non-covalently attached to the inner surface of the skin-covering material.

In an aspect, one or more of the plurality of signal-generating complexes are covalently attached to at least the inner surface of the skin-covering material using a cross-linking reagent. In an aspect, the crosslinking reagent includes at least one of a homobifunctional, heterobifunctional, and/or photoreactive crosslinking reagent. For example, the inner surface of the skin-covering material may include a layer of silane to which is bound one arm of a heterobifunctional crosslinking reagent. See, e.g., U.S. Pat. No. 5,077,210, which is incorporated herein by reference. In an embodiment, the other arm of the heterobifunctional crosslinking reagent is covalently bound to a signal-generating complex. The one or more of the plurality of signal-generating complexes can be cross-linked to the inner surface of the skin-covering material through amine groups, carbohydrate groups, sulfhydryl groups, or combinations thereof. Non-limiting examples of homobifunctional crosslinking reagents include primary amine/primary amine linkers such as BSOCES ((bis(2-[succinimidooxy-carbonyloxy] ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Non-limiting examples of heterobifunctional cross-linking reagents include primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-gamma-maleimidobutyryloxysulfosuccinimide ester), EMCS (N-(epsilon-maleimidocaproyloxy) succinimide ester), Sulfo EMCS (N-(epsilon-maleimidocaproyloxy) sulfo succinimide), SIAB (N-succinimidyl(4-iodoacetyl)aminobenzoate), SMCC (succinimidyl 4-(N-maleimidomethyl) cyclohexane-1-carboxylate), SMPB (succinimidyl 4-(rho-maleimidophenyl) butyrate), Sulfo SIAB (N-sulfosuccinimidyl(4-iodoacetyl) aminobenzoate), Sulfo SMCC (sulfosuccinimidyl 4-(N-maleimidomethyl) cyclohexane-1-carboxylate), Sulfo SMPB (sulfosuccinimidyl 4-(rho-maleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH (N-(epsilon-maleimidocaproic acid) hydrazide); and amine/carboxyl linkers such as EDC (1-ethyl-3-(3-dimethylaminopropyl) carbodiimide hydrochloride).

In an aspect, one or more of the plurality of signal-generating complexes are non-covalently attached to at least the inner surface of the skin-covering material. Non-limiting examples of non-covalent interactions include hydrogen bonds, ionic bonds, van der Waals forces, and hydrophobic interactions. For example, a signal-generating complex that includes an oligonucleotide could be non-covalently attached to a complementary oligonucleotide incorporated into the inner surface of a skin-covering material. In an aspect, the one or more of the plurality of signal-generating complexes are non-covalently attached to the inner surface of the skin-covering material through protein-protein interactions. For example, a signal-generating complex that includes biotin could be non-covalently attached to an inner surface that includes streptavidin or avidin. For example, a single chain antibody may incorporate streptavidin as part of a fusion protein to facilitate attachment of the antibody to a solid substrate via a biotin-streptavidin linkage. See, e.g., Koo et al. (1999) *Appl. Environ. Microbiol.* 64:2497-2502, which is incorporated herein by reference. Other non-limiting examples non-covalent interactions include interactions between protein A or protein G and immunoglobulins, ligands with receptors, and secondary antibodies with primary antibodies.

In an aspect, the plurality of signal-generating complexes associated with the inner surface of the skin-covering material are configured to emit one or more signals in response to two or more types of microbes, each type of microbe associated with a unique signal emitted from one or more of the plurality of signal-generating complexes. In an aspect, the plurality of signal generating complexes includes a plurality of signal-generating complexes of at least one first type and a plurality of signal-generating complexes of at least one second type. In an aspect, the plurality of signal-generating elements of the at least one first type differ from the plurality of signal-generating elements of the at least one second type. In an aspect, the plurality of the signal-generating complexes of the at least one first type emit one or more signals of a first type in response to at least one first type of microbe and the plurality of signal-generating complexes of the at least one second type emit one or more signals of a second type in response to at least one second type of microbe. In an aspect, the at least one first type of microbe differs from the at least one second type of microbe. For example, the at least one first type of microbe can include a different phylum from the at least one second type of microbe, e.g., bacteria versus fungi. For example, the at least one first type of microbe can include a different genus from the at least one second type of microbe, e.g., *Staphylococcus* versus *Propionibacterium*. For example, the at least one first type of microbe can includes a different species from the at least one second type of microbe, e.g., *Staphylococcus aureus* versus *Staphylococcus epidermidis*. In an aspect, the one or more signals of the first type differ from the one or more signals of the second type. For example, the one or more signals of the first type can differ in wavelength, e.g., color, from the one or more signals for the second type. In an aspect, a specific color can be associated with a response to a specific microbe, e.g., a red signal associated with *Staphylococcus* and a green signal associated with *Propionibacterium*.

In an aspect, the skin-covering material includes at least one registration mark to register the skin-covering material to at least one landmark on the skin surface of the individual. One or more registration marks on the skin-covering material can be used to align with one or more landmarks on the skin surface. The one or more landmarks can include one or more of pigmentation, pigmented areas, tattoos, skin texture patterns, blemishes, scars, anatomical features, or subsurface blood vessels associated with the skin surface. In an aspect, the one or more registration marks are incorporated into the manufacture of the skin-covering material based on a digital image of the skin surface including the one or more landmarks over which the skin-covering material will be placed. In an aspect, the one or more registration marks can be added with a pen or other marking device while the skin-covering material is on the skin surface of the individual.

In an aspect, the skin-covering material includes one or more tearable lines of perforations. In an aspect, the one or more tearable lines of perforation are configured to allow separation of the skin-covering material into two or more segments. In an aspect, the skin-covering material can be manufactured with perforations. For example, the skin-covering material may be manufactured using a three-dimensional printing process as described herein in which the digital template for the skin-covering material includes perforations. In an aspect, the perforations are added to the skin-covering material after manufacture. For example, a skin-covering material manufactured from a thin sheet of material, e.g., latex or paper may be modified with a device configured to punch holes through the skin-covering material. In general, the tearable lines of perforations allow the skin-covering material to be separated into pieces that can be accommodated by the imaging window or scanning surface of the image-capture device, the one or more resulting images digitally recombined to form a composite image of the inner surface of the skin-covering material. In an aspect, the one or more tearable lines of perforations are configured to allow partial separation of the skin-covering material. For example, the one or more tearable lines of perforations can be configured to allow partial separation of portions of an otherwise non-planar skin-covering material to be flattened, i.e., made planar, to facilitate imaging with an image capture device.

Figure 3:
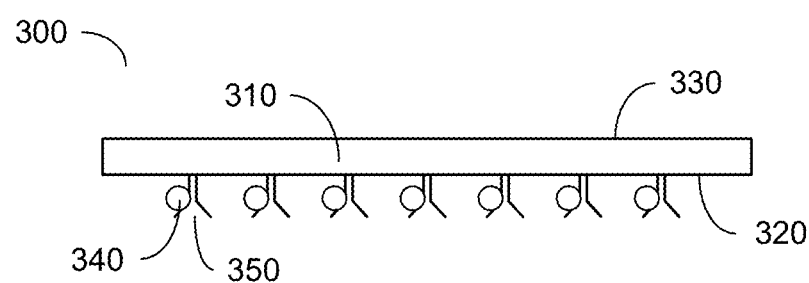
FIG. 3 is a cross-section through a skin-covering material including a plurality of signal-generating complexes.

In an aspect, each of the plurality of signal-generating complexes includes at least one signal-generating element and to at least one specific microbe-binding element. In an aspect, the at least one signal-generating element is operably coupled to the at least one specific microbe-binding element, wherein the at least one signal generating element is configured to emit one or more signals in response to at least one type of microbe bound to the operably coupled at least one specific microbe-binding element. FIG. 3 is a schematic cross-section through device 300 for assessing microbiota of skin. Device 300 includes skin-covering material 310 with inner surface 320 and outer surface 330. Inner surface 320 includes attached thereto a plurality of signal-generating complexes, each of the signal-generating complexes including signal-generating element 340 and specific microbe-binding element 350. In an aspect, signal-generating element 340 is operably coupled to specific microbe-binding element 350. Specific microbe-binding element 350 is configured to specifically recognize at least one type of microbe. Signal-generating element 340 is configured to emit one or more signals in response to at least one type of microbe bound to the operably coupled specific microbe-binding element 350.

In an aspect, the skin-covering material includes a plurality of signal-generating elements of at least one first type including at least one signal-generating element of a first type operably coupled to at least one specific microbe-binding element of a first type, the at least one signal-generating element of the first type to emit one or more signals of a first type in response to at least one first type of microbe bound to the operably coupled at least one specific microbe-binding element of the first type and a plurality of signal-generating complexes of at least one second type including at least one signal-generating element of a second type operably coupled to at least one specific microbe-binding element of a second type, the at least one signal-generating element of the second type to emit one or more signals for a second type in response to at least one second type of microbe bound to the operably coupled at least one specific microbe-binding element of the second type. In an aspect, the at least one first type of microbe differs from the at least one second type of microbe. In an aspect, the one or more signals of the first type differ from the one or more signals of the second type.

Figure 4:
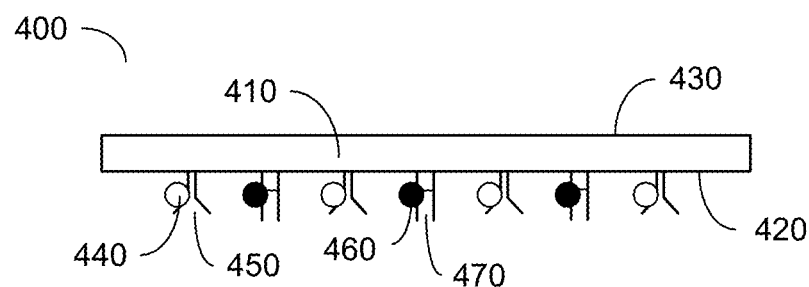
FIG. 4 is a cross-section through a skin-covering material including a plurality of signal-generating complexes.

FIG. 4 is a schematic cross-section through device 400 for assessing microbiota of skin and including a plurality of signal generating-complexes of a first type and a plurality of signal-generating complexes of a second type. Device 400 includes skin-covering material 410 with inner surface 420 and outer surface 430. Inner surface 420 includes attached thereto a plurality of signal-generating complexes of a first type including signal-generating element of a first type 440 and specific microbe-binding element of a first type 450 and a plurality of signal-generating complexes of a second type including signal-generating element of a second type 460 and specific microbe-binding element of a second type 470. In an aspect, signal-generating element of a first type 440 is operably coupled to a specific microbe-binding element of a first type 450 and signal-generating element of a second type 460 is operably coupled to a specific microbe-binding element of a second type 470. Specific microbe-binding element of a first type 450 recognizes at least one first type of microbe while specific microbe-binding element of a second type 470 recognizes at least one second type of microbe. Signal-generating element of a first type 440 is configured to emit one or more signals of a first type in response to the at least one first type of microbe bound to operably coupled specific microbe-binding element of a first type 450 and signal-generating element of a second type 460 is configured to emit one or more signals of a second type in response to the at least one second type of microbe bound to operably coupled specific microbe-binding element of a second type 470.

In an aspect, a given type of signal-generating element is operably coupled to a given type of specific microbe-binding element to provide a microbe-specific signal. For example, a first signal-generating element emitting light at a first wavelength band, e.g., red fluorescence, may be operably coupled to a first type of specific microbe-binding element that binds a first type of microbe while a second signal-generating element emitting light at a second wavelength band, e.g., green fluorescence, may be operably coupled to a second type of specific microbe-binding element that binds a second type of microbe, allowing for distinct detection of the first type of microbe versus the second type of microbe.

Figure 5A:
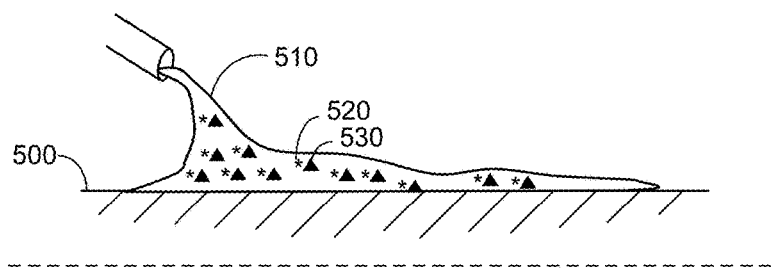
FIG. 5A illustrates application of a peelable skin-covering material including a plurality of signal-generating complexes to a skin surface.
Figure 5B:
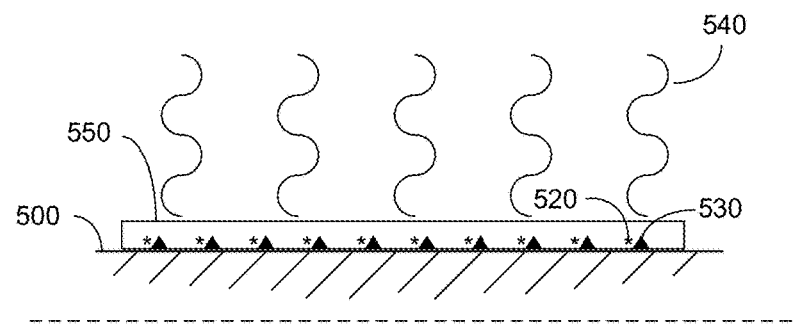
FIG. 5B shows a cross-section through a peelable skin-covering material including a plurality of signal-generating complexes on a skin surface.
Figure 5C:
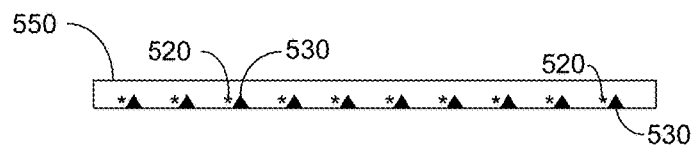
FIG. 5C illustrates a cross-section through a peelable skin-covering material including a plurality of signal-generating complexes.

FIG. 5 is a schematic cross-section through a peelable skin-covering material for assessing microbiota of skin. FIG. 5A shows settable material 510 applied to skin surface 500. Settable material includes a plurality of signal-generating complexes, each signal-generating complex including at least one signal-generating element 520 and at least one specific microbe-binding element 530. In an aspect, the at least one signal-generating element 520 is operably coupled to the at least one specific microbe-binding element 530. FIG. 5B shows peelable skin-covering material 550 formed on skin surface 500 from settable material 510 in response to applied stimulus 540. Peelable skin-covering material 550 includes the plurality of signal-generating complexes including signal-generating element 520 and specific microbe-binding element 530. FIG. 5C shows peelable skin-covering material 550 with the plurality of signal-generating complexes including signal-generating element 520 and specific microbe-binding element 530.

Figure 6A:
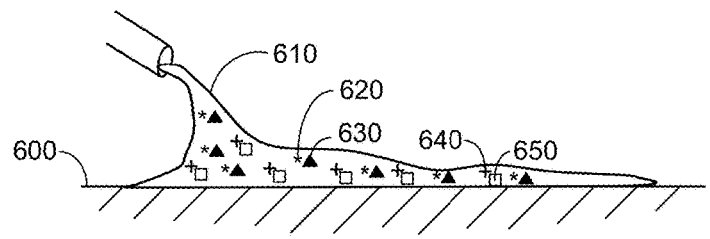
FIG. 6A illustrates application of a peelable skin-covering material including a plurality of signal-generating complexes to a skin surface.
Figure 6B:
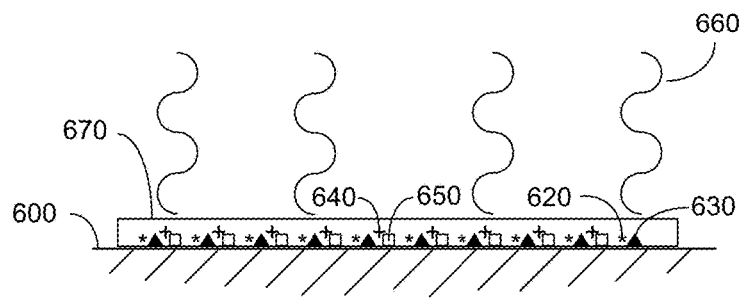
FIG. 6B shows a cross-section through a peelable skin-covering material including a plurality of signal-generating complexes on a skin surface.
Figure 6C:
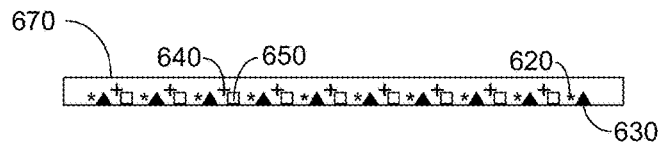
FIG. 6C illustrates a cross-section through a peelable skin-covering material including a plurality of signal-generating complexes.

FIG. 6 is a schematic cross-section through a peelable skin-covering material including a plurality of signal-generating complexes of a first type and a plurality of signal-generating complexes of a second type. FIG. 6A shows settable material 610 applied to skin surface 600. Settable material includes a plurality of signal-generating complexes of a first type including signal-generating element of a first type 620 and a specific microbe-binding element of a first type 630 and a plurality of signal-generating complexes of a second type including signal-generating element of a second type 640 and a specific microbe-binding element of a second type 650. In an aspect, signal-generating element of a first type 620 is operably coupled to a specific microbe-binding element of a first type 630 and signal-generating element of a second type 640 is operably coupled to a specific microbe-binding element of a second type 650. Specific microbe-binding element of a first type 630 recognizes at least one first type of microbe while specific microbe-binding element of a second type 650 recognizes at least one second type of microbe. Signal-generating element 620 is configured to emit one or more signals of a first type in response to the at least one first type of microbe bound to operably coupled specific microbe-binding element 630 and signal-generating element of a second type 640 is configured to emit one or more signals of a second type in response to the at least one second type of microbe bound to operably coupled specific microbe-binding element of a second type 650. FIG. 6B shows peelable skin-covering material 670 formed on skin surface 600 from settable material 610 in response to applied stimulus 660. Peelable skin-covering material 670 includes the plurality of signal-generating complexes of the first type including signal-generating element of a first type 620 operably coupled to specific microbe-binding element of a first type 630 and the plurality of signal-generating complexes of the second type including signal-generating element of a second type 640 operably coupled to specific microbe-binding element of a second type 650. FIG. 6C shows peelable skin-covering material 670 including the plurality of signal-generating complexes of the first type including signal-generating element of a first type 620 operably coupled to specific microbe-binding element of a first type 630 and the plurality of signal-generating complexes of the second type including signal-generating element of a second type 640 operably coupled to specific microbe-binding element of a second type 650. In an aspect, peelable skin-covering material 670 is configured to detect at least two or more types of microbes, each type of microbe binding to a specific microbe-binding element and eliciting a distinct and measureable signal, e.g., red versus green versus blue.

Specific Microbe-Binding Elements

In an aspect, each of the plurality of signal-generating complexes associated with the skin-covering material includes at least one specific microbe-binding element. The at least one specific microbe-binding element specifically recognizes at least one type of microbe. The at least one type of microbe can include at least one type of bacteria, fungus, virus, or parasite. In an aspect, the at least one specific microbe-binding element recognizes at least one type of mutualistic microbe, commensal microbe, or pathogenic microbe. In an aspect, the at least one specific microbe-binding element recognizes at least one type of microbe resident on the skin surface of the individual. Non-limiting examples of microbes have been described above herein.

In an aspect, the at least one specific microbe-binding element of the signal-generating complex is configured to specifically recognize and bind a particular microbe or class of microbes. In an aspect, the specific microbe-binding element may be specific for a particular type of microbe, e.g., bacteria versus fungus. In an aspect, the specific microbe-binding element may be specific for Gram-positive versus Gram-negative bacteria or a particular genus of microbes, e.g., *Propionibacterium* versus *Staphylococcus*. In an aspect, the specific microbe-binding element may be specific for a particular species of bacteria within a genus, e.g., *S. aureus* versus *S. epidermidis*.

Non-limiting examples of specific microbe-binding elements include antibodies, aptamers, oligonucelotides, or anti-16S rRNAs. Other non-limiting examples of specific microbe-binding elements include antibody fragments, peptides, peptide nucleic acids, proteins, viruses, phospholipids, carbohydrates, enzymes, receptors, lectins, peptide aptamers, bacteria, cells, cell fragments, inorganic molecules, organic molecules, artificial binding substrates (e.g., those formed by molecular imprinting), or combinations thereof.

In an aspect, the specific microbe-binding element recognizes one or more components of at least one type of microbe. In an aspect, the specific microbe-binding element recognizes one or more biomolecules associated with the surface of a microbe, e.g., bacteria, a virus, a fungus, or a parasite. In an aspect, the specific microbe-binding element recognizes components of microbe surface biomolecules including amino acid sequences, oligosaccharides, proteoglycans, proteins, peptides, and/or lipids. For example, the specific microbe-binding element can recognize and bind teichoic acids and/or peptidoglycans associated with Gram-positive bacteria. For example, the specific microbe-binding element can recognize and bind common lipopolysaccharide moieties, e.g., 2-keto-3-deoxyoctanate, associated with Gram-negative bacteria. For example, the specific microbe-binding element can recognize and bind chitin associated with fungi. In an aspect, the specific microbe-binding element recognizes nucleic acids. For example, the specific microbe-binding element may be configured to recognize and bind one or more DNA or RNA sequence associated with the at least one type of microbe.

In an aspect, the specific microbe-binding element recognizes one or more biomolecules associated with the bacterial outer membrane, cell wall, and/or cytoplasmic membrane. Non-limiting examples of biomolecules associated with the bacterial outer membrane of Gram-negative bacteria include, but are not limited to, lipopolysaccharide and OMP (outer membrane protein) porins, the latter of which are exemplified by OmpC, OmpF and PhoP of E call Non-limiting examples of biomolecules associated with the bacterial cell wall of both Gram-positive and Gram-negative bacterial include, but are not limited to, peptidoglycans, i.e., polymers composed of an alternating sequence of N-acetyl-glucoamine and N-acetyl-muraminic acid and crosslinked by amino acids and amino acid derivatives. Non-limiting examples of biomolecules associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of biomolecules associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential biomolecules associated with bacteria have been described in Chung, et al. (2001) *J Bacteriology* 183:1012-1021, which is incorporated herein by reference.

In an aspect, the specific microbe-binding element recognizes one or more biomolecules associated with at least one type of fungus. Non-limiting examples of biomolecules associated with fungi, e.g., the outer surface of fungi, include chitins and glucans, e.g., alpha glucans (dextran, glycogen, pullulan, starch) and beta glucans (cellulose, curdlan, laminarin, chrysolaninarin, lentinan, lichenin, pleuran, zymosan).

In an aspect, the specific microbe-binding element recognizes a biomolecule associated with at least one type of virus. For example, the specific microbe-binding element may be configured to recognize and bind one or more capsid proteins of the virus. For example, the specific microbe-binding element may be configured to recognize and bind to VP5, a major capsid protein of herpes viruses.

In an aspect, the specific microbe-binding element can include a specific microbe-binding antibody. For example, the specific microbe-binding antibody can include one or more antibodies configured to recognize and bind one or more bacterium, fungus, and/or virus. Antibodies or fragments thereof for use in generating the specific microbe-binding element can include, but are not limited to, monoclonal antibodies, polyclonal antibodies, Fab fragments of monoclonal antibodies, Fab fragments of polyclonal antibodies, F(ab')2 fragments of monoclonal antibodies, F(ab')2 fragments of polyclonal antibodies, chimeric antibodies, non-human antibodies, fully human antibodies, among others. Single chain or multiple chain antigen-recognition sites can be used. Multiple chain antigen recognition sites can be fused or unfused. Antibody fragments can be produced by modification of whole antibodies or synthesized de novo using recombinant DNA technologies. Antibodies or fragments thereof may be generated using standard methods.

Alternatively, an antibody or fragment thereof that recognizes at least one type of microbe may be generated, for example, using phage display technology. See, e.g., Kupper et al. (2005) *BMC Biotechnology* 5:4, which is incorporated herein by reference. An antibody a fragment thereof, or an artificial antibody, e.g., Affibody® artificial antibodies (Affibody AB, Bromma, Sweden) can be prepared using in silico design (Knappik et al. (2000) *J. Mol. Biol.* 296:57-86, which is incorporated herein by reference). In some embodiments, antibodies directed against specific microbes may be available from a commercial source (from e.g., Novus Biological, Littleton, Colo.; Sigma-Aldrich, St. Louis, Mo.; United States Biological, Swampscott, Mass.). Non-limiting sources of antibodies designed to bind specific microbes, e.g., specific bacteria, fungi, viruses, or parasites, can be found in Linscott's Directory of Immunological and Biological Reagents (accessible through the website address http://www.linscottdirectory.com/).

In an aspect, the specific microbe-binding element includes a specific microbe-binding aptamer. The aptamer can be an oligonucleotide RNA- or DNA-based aptamer configured to recognize and bind one or more of a bacteria, fungus, virus, or parasite. Aptamers are artificial oligonucleotides (DNA or RNA) that can bind to a wide variety of entities (e.g., metal ions, small organic molecules, proteins, and cells) with high selectivity, specificity, and affinity. Aptamers may be isolated from a large library of $10^{14}$ to $10^{15}$ random oligonucleotide sequences using an iterative in vitro selection procedure termed "systemic evolution of ligands by exponential enrichment" (SELEX). See, e.g., Cao, et al (2005) *Current Proteomics* 2:31-40; Proske et al. (2005) *Appl. Microbiol. Biotechnol.* 69:367-374, which are incorporated herein by reference. In general, SELEX may be used to generate aptamers against any of a number of microbial targets, including but not limited to bacteria, fungi, viruses, and parasites. For example, Cao, et al., describe using SELEX and whole bacteria to generate a panel of DNA aptamers configured to detect *Staphylococcus aureus* (in Nucleic Acids Res., 37:4621-4628, 2009). See, e.g., Chen et al. (2007) *Biochem. Biophys, Res. Commun.* 357:743-748, Nitsche et al. (2007) *BMC Biotechnol.* 7:48; Gopinath et al. (2012) *J. Virol.* 86:6732-6744; Low et al. (2009) *Biochem. Biophys, Res. Commun.* 386:544-548, which are incorporated herein by reference.

In an aspect, the specific microbe-binding element includes a peptide-based aptamer, an artificial protein in which inserted peptides are expressed as part of the primary sequence of a structurally stable protein and having binding affinities comparable to antibodies. See, e.g., Crawford, et al., *Brief Funct. Genomic Proteomic* 2:72-79, 2003, which is incorporated herein by reference. Peptide aptamers can be generated by screening a target, e.g., all or part of a microbe, against yeast two-hybrid libraries, yeast expression libraries, bacterial expression libraries and/or retroviral libraries.

In an aspect, the specific microbe-binding element includes a novel peptide configured to specifically recognize and bind one or more microbes. Novel peptides that bind specific targets, e.g., a surface component of a bacteria, virus, or fungi, can be generated, for example, using phage display methodologies. See, e.g., Spear, et al. (2001) *Cancer Gene Ther.* 8:506-511, which is incorporated herein by reference. In an aspect, the phage express novel peptides on the surface as fusion proteins in association with a phage major or minor coat protein and can be screened for binding interaction with one or more microbes.

In an aspect, the specific microbe-binding element can include a ligand that specifically recognizes one or more microbes. For example, the specific microbe-binding element can include CD14, which is associated with monocyte/macrophages and known to bind lipopolysaccharide associated with Gram-negative bacteria as well as lipoteichoic acid associated with the Gram-positive bacteria *Bacillus subtilis* (see, e.g., Fan, et al. (1999) *Infect. Immun.* 67: 2964-2968). In an aspect, specific microbe-binding element can include all or part of a pattern recognition receptor that recognizes microbe-specific molecules (e.g., bacterial carbohydrates, bacterial or viral DNA or RNA, bacterial peptides, peptidoglycans, lipoteichoic acids, N-formylmethionine, lipoproteins, and fungal glucans). Non-limiting examples of pattern recognition receptors with microbe-binding properties include toll-like receptors, C-type lectin receptors, NOD-like receptors, RIG-I-like receptors, RNA helicases, complement receptors, collectins, ficolins, pentraxins, C-reactive proteins, lipid transferases, and the like. See, e.g., Modlin (2012) *J. Invest. Dermatol.* 132:882-886; Gauglitz et al. (2012) *Acta Derm. Venereol.* 92:291-298, which are incorporated herein by reference.

In an aspect, the specific microbe-binding element includes plasminogen to bind a fungus, e.g., *Candida albicans*. See, e.g., Crowe et al. (2003) Mol. Microbiol. 47:1637-1651, which is incorporated herein by reference.

In an aspect, the specific microbe-binding element includes a lectin. Lectins include carbohydrate-binding proteins that bind cell surface glycoproteins and/or glycolipids. Because of the specificity that each lectin has toward a particular carbohydrate structure, even oligosaccharides with identical sugar compositions can be distinguished or separated. Examples of lectins include, but are not limited to, algal lectins, e.g., b-prism lectin; animal lectins, e.g., tachylectin-2, C-type lectins, C-type lectin-like, calnexin-calreticulin, capsid protein, chitin-binding protein, ficolins, fucolectin, H-typelectins, I-type lectins, sialoadhesin, siglec-5, siglec-7, microneal protein, P-type lectins, pentrxin, b-trefoil, galectins, congerins, selenocosmia huwena lectin-I, Hcgp-39, Ym1; bacterial lectins, e.g., *Pseudomonas* PA-IL, Burkholderia lectins, chromobacterium CV-IIL, *Pseudomonas* PA IIL, Ralsonia RS-ILL, ADP-ribosylating toxin, Ralstonia lectin, Clostridium hemagglutinin, botulinum toxin, tetanus toxin, cyanobacterial lectins, FimH, GafD, PapG, Staphylococcal enterotoxin B, toxin SSL11, toxin SSL5; fungal and yeast lectins, e.g., Aleuria aurantia lectin, integrin-like lectin, Agaricus lectin, Sclerotium lectin, Xerocomus lectin, Laetiporus lectin, Marasmius oreades agglutinin, agrocybe galectin, coprinus galectin-2, Ig-like lectins, L-type lectins; plant lectins, e.g., alpha-D-mannose-specific plant lectins, amaranthus antimicrobial peptide, hevein, pokeweed lectin, Urtica dioica UD, wheat germ WGA-1, WGA-2, WGA-3, artocarpin, artocarpus hirsute AHL, banana lectin, Calsepa, heltuba, jacalin, Maclura pomifera MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein. See, e.g., E. Bettler, R. Loris, A. Imberty "3D-Lectin database: A web site for images and structural information on lectins" 3rd Electronic Glycoscience Conference, The internet and World Wide Web, 6-17 Oct. 1997; http://www.cermav.com.cnrs.fr/lectines/, which is incorporated herein by reference.

In an aspect, the specific microbe-binding element includes an artificial binding substrate formed by the process of molecular imprinting. In the process of molecular imprinting, a template, e.g., a microbe or a surface component of a microbe, is combined with functional monomers which, upon cross-linking, form a polymer matrix that surrounds the template. See, e.g., Alexander, et al. (2006) *J. Mol. Recognit.* 19:106-180, which is incorporated herein by reference. Removal of the template leaves a stable cavity in the polymer matrix that is complementary in size and shape to the template. In an aspect, functional monomers of acrylamide and ethylene glycol dimethacrylate can be mixed with at least one type of microbe or parts thereof in the presence of a photoinitiator and ultraviolet irradiation used to cross-link the monomers. The resulting polymer can be crushed or ground into smaller pieces and washed to remove the at least one type of microbe or parts thereof, leaving a particulate matrix material capable of binding the at least one type of microbe. Examples of other functional monomers, cross-linkers and initiators that can be used to generate an artificial binding substrate are provided. See, e.g., U.S. Pat. No. 7,319,038; Alexander, et al. (2006) *J. Mol. Recognit.* 19:106-180, each of which is incorporated herein by reference. In an aspect, hydrogels can be used for molecular imprinting. Other examples of synthetic binders are provided. See, e.g., U.S. Pat. Nos. 6,255,461; and 6,797,522; and Ye and Haupt (2004) *Anal Bioanal Chem.* 378: 1887-1897; Peppas and Huang (2002) *Pharm Res.* 19: 578-587, each of which is incorporated herein by reference.

In an aspect, the specific microbe-binding element recognizes and binds DNA and/or RNA sequences associated with the at least one type of microbe. In this instance, the one or more microbes may first be subjected to a lysis agent, e.g., a detergent, to make the cytoplasmic components of the microbes more accessible. For example, the specific microbe-binding element may be a cDNA element engaged in DNA-DNA hybridization with microbe DNA sequence. In an aspect, the specific microbe-binding element may include oligonucleotides capable of binding to unique 16S small subunit ribosomal (rRNA) genes. In an aspect, various phylogenetic markers may be targeted including ribosomal RNA, elongation and initiation factors, RNA polymerase subunits, DNA gyrases, heat shock proteins, and recA proteins.

In an aspect, the inner surface of the skin-covering material can be modified with one or more materials that non-selectively interact with biomolecules on the outer surface of microbes, e.g., proteins, polysaccharides, carbohydrates, phospholipids, proteoglycans, and the like. In an aspect, the one or more materials take advantage of hydrogen bonding, electrostatic and/or hydrophobic interactions to capture microbes from the skin surface onto the inner surface of the skin-covering material. Non-limiting examples of materials include poly-ionic surfaces, e.g., poly-cationic surfaces such as polyamino acids (e.g., polylysine) and fibronectin for binding microbes that have an overall negative surface charge. Other non-limiting examples of materials include nitrocellulose, cellulose nitrate, hydrophobic polymers, PVDF coated surface, nylon coated surface, streptavidin coated substrate to bind biotin labeled DNA, protein, peptide, Concanavalin A, and/or NETS-ester coated surface.

Signal-Generating Element

In an aspect, each of the plurality of signal-generating complexes associated with the skin-covering material includes at least one signal-generating element. In an aspect, the at least one signal-generating element is operably coupled to at least one specific microbe-binding element, the at least one signal-generating element configured to emit one or more signals in response to at least one microbe bound to the at least one operably coupled specific microbe-binding element. In an aspect, the signal-generating element emits one or more signals in response to a structural change in the signal-generating complex in the presence of a microbe. In an aspect, the signal-generating element emits one or more signals only when a microbe is bound, e.g., an on/off detection system. Alternatively, the signal-generating element emits a first signal type in the absence of a bound microbe and a second signal type in the presence of a bound microbe, e.g., a change in the color or other property of emitted light.

In an aspect, the signal-generating complex can include at least one signal-generating element configured to emit one or more signals in response to a chemical reaction, e.g., an enzymatic cleavage resulting in release of all or part of the signal-generating element, e.g., a chromogenic or fluorogenic product. For example, the signal-generating complex may include an enzymatically cleavable linkage to the signal-generating element, the enzymatically cleavable linkage cleaved in response to an enzyme activity of a microbe.

Non-limiting examples of signal-generating elements include chromogenic signal-generating elements, fluorogenic signal-generating elements, electrical signal-generating elements, radio signal-generating elements, electromagnetic signal-generating elements, acoustic signal-generating elements, or magnetic signal-generating elements. In an aspect, the at least one signal-generating element can emit one or more of a chromogenic signal, a fluorescent signal, an electromagnetic signal, an acoustic signal, or a luminescent signal. Non-limiting examples of signal-generating elements include, but are not limited to, at least one of a chromogenic element, a fluorogenic element, a quantum dot, a dye, or chemiluminescent dye, or a combination thereof. Other non-limiting examples of signal-generating elements include a radioactive element; a radiopaque dye; a radiofrequency identification tag; a contrast agent, a visible dye, volatile label; mass label; luminescent label, e.g., bioluminescent or chemiluminescent; metallic label, e.g., gold particles, magnetic beads, or paramagnetic beads; dyes, e.g., direct, indirect, or releasable; or a combination thereof.

In an aspect, the signal-generating element is a chromogenic or fluorogenic signal-generating element. In an aspect, the chromogenic or fluorogenic signal-generating element can be a chemical entity operably coupled to the specific microbe-binding element that changes color in response to an interaction with a microbe, e.g., binding the microbe. In an aspect, the chromogenic or fluorogenic signal-generating element can change color in response to metabolism of a microbe bound to and/or in proximity to the inner surface of the skin-covering material. In an aspect, the chromogenic or fluorogenic signal-generating element can change color in response to one or more components excreted from a microbe in proximity to the signal-generating complex. For example, the chromogenic or fluorogenic signal-generating element can by linked to metabolic activity of certain classes of biochemicals including sugars, hexo-phoshates, amino acids, hexose sugars, carboxylic acids, esters, and fatty acids. In an aspect, the chromogenic or fluorogenic signal-generating element can change color in response to an interaction with a microbe independent of the specific microbe-binding element. For example, the chromogenic or fluorogenic signal-generating element can include tetrazolium salts which form violet-colored formazans in response to microbe metabolism. See, e.g., Tachon et al. (2009) *Microbiology* 155:2941-2948, which is incorporated herein by reference.

In an aspect, the signal-generating complex can include a signal-generating element that is a chromogenic substrate. Chromogenic substrates can include peptides that generate color in response to interaction with microbe-derived proteolytic enzymes. For example, the chromogenic substrate may include in part a chemical group, e.g., para-nitroaniline, which generates a color change when released by enzymatic cleavage. For example, a chromogenic substrate associated with the skin-covering material may interact with an enzyme located on the exterior of the microbe, e.g., located in a bacterial cell wall, to generate a color signal. As an example, L-alanine-4-nitroanilide can be used as a chromogenic substrate for L-alanine-aminopeptidase, commonly associated with Gram-negative bacteria. The substrate L-alanine-4-nitroanilide is split by L-alanine aminopeptidases into L-alanine and 4-nitroaniline, the latter producing a yellow color. The color change can be followed spectrophotometrically and may be proportional to the proteolytic activity.

In an aspect, the signal-generating complex can include a signal-generating element that is a fluorogenic signal-generating element. In an aspect, fluorogenic signal-generating elements can include chemical dyes or fluorophores that emit light, i.e., fluoresce, at various wavelengths in response to excitation energy. In an aspect, the fluorogenic signal-generating element can include a quantum dot or semiconductor nanocrystals that fluoresce at various wavelengths in response to excitation energy. See, e.g., Jaiswal et al. (2003) *Nature Biotech.* 21:47-51, which is incorporated herein by reference. Non-limiting examples of fluorophores for use as fluorogenic signal-generating elements include fluorescein (FITC), indocyanine green (ICG) and rhodamine B, red and near infrared emitting fluorophores (600-1200 nm) including cyanine dyes such as Cy5, Cy5.5, and Cy7 (Amersham Biosciences, Piscataway, N.J., USA) and/or a variety of Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA). Additional fluorophores include IRDye800, IRDye700, and IRDye680 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.), NIAD-4 (ICx Technologies, Arlington, Va.). Other fluorescing dyes include BODIPY-FL, europium, green, yellow and red fluorescent proteins, luciferase.

In an aspect, the signal-generating complex includes a signal-generating element that is a magnetic signal-generating element, e.g., magnetic beads or particles. In an aspect, the signal-generating complex can include magnetic beads or particles conjugated to the complex via an enzymatically cleavable linkage which in the presence of a microbe is cleaved, releasing the magnetic bead or particle. In an aspect, Magnetic beads and magnetic particles of various sub-millimeter size are available from commercial sources (e.g., from Seradyn-Thermo Scientific, Indianapolis, Ind.; Dynal-Invitrogen, Carlsbad, Calif.).

In an aspect, the signal-generating complex includes a signal-generating element that is a radiofrequency identification tag. In an aspect, the signal-generating complex can include a radiofrequency identification tag conjugated to the complex via an enzymatically cleavable linkage which in the presence of a microbe is cleaved, releasing the radiofrequency identification tag. In an aspect, the signal-generating element can include a sub-millimeter radiofrequency identification tag. See, e.g., Hornyak (2008) *Scientific American Magazine*, pp 68-71, February 2008, which is incorporated herein by reference. Alternatively, the signal-generating element can include one or more bokodes, millimeter sized visual tags that can be captured with a camera. See, e.g., Mohan et al. *ACM Transactions on Graphics* Proceedings of SIGGRAPH 2009, Aug. 3-7, 2009, New Orleans, which is incorporated herein by reference.

In an aspect, the signal-generating complex can be configured such that binding of one or more microbes to the specific microbe-binding element operably coupled to the signal-generating element results in a conformational change that can be measured using fluorescence resonance energy transfer (FRET). FRET is a distance-dependent interaction between the electronic excited states of two dye molecules in which excitation is transferred from a donor molecule to an acceptor molecule without emission of a photon. In an aspect, interaction of a donor molecule with an acceptor molecule can lead to a shift in the emission wavelength associated with excitation of the acceptor molecule. In an aspect, interaction of a donor molecule with an acceptor molecule can lead to quenching of the donor emission. In an aspect, the signal-generating complex can include at least one signal-generating element that includes at least one donor molecule and at least one acceptor molecule attached to a specific microbe-binding element, e.g., an antibody or aptamer. In this configuration, interaction of at least one type of microbe with the specific microbe-binding element, e.g., the antibody or aptamer, causes a conformational change in the specific microbe-binding element and results in a change in the distance between the donor and acceptor molecules components of the signal-generating element and a change in measurable signal, e.g., fluorescence.

A variety of donor and acceptor fluorophore pairs can be considered for FRET including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., USA) can be paired with other AF fluorophores for use in FRET. Some examples include, but are not limited, to AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

Other non-limiting examples of fluorophores for FRET-based signaling include cyanine dyes Cy3, Cy5, Cy5.5 and Cy7, which emit in the red and far red wavelength range (>550 nm). For example, Cy3, which emits maximally at 570 nm and Cy5, which emits at 670 nm, can be used as a donor-acceptor pair. When Cy3 and Cy5 are not proximal to one another, excitation at 540 nm results only in the emission from of light from Cy3 at 590 nm. In contrast, when Cy3 and Cy5 are brought into proximity by a conformation change, e.g., by binding of a microbe to a specific microbe-binding element, excitation at 540 nm results in an emission at 680 nm.

In an aspect, the signal-generating element includes a quenching dye to quench the fluorescence of visible light-excited fluorophores. Non-limiting examples of quenching dyes include DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). Non-limiting examples of donor fluorophore and quencher pairs include fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

In an aspect, the signal-generating complex for FRET-based signaling includes a specific microbe-binding element that is an RNA or DNA oligonucleotide-based aptamer and a signal-generating element that includes one or more donor fluorophore and one or more acceptor fluorophore or quencher. See, e.g., Cao et al. (2005) *Current Proteomics* 2:31-40 and U.S. Patent Application 2009/0186342, which are incorporated herein by reference. For example, the aptamer including a donor fluorophore and an acceptor fluorophore or quencher can be configured to undergo a conformational change upon binding a target, e.g., a microbe, causing the distance between the donor fluorophore and the acceptor fluorophore or quencher to shift and leading to a change in measurable fluorescence. See, e.g., Ikanovic et al. (2007) J Fluorescence 17:193-199, which is incorporated herein by reference. As described above herein, aptamers against a variety of targets, including whole microbes, can be isolated from a large library of $10^{14}$ to $10^{15}$ random oligonucleotide sequences using an iterative in vitro selection procedure often termed "systematic evolution of ligands by exponential enrichment" (SELEX).

In an aspect, an aptamer-based signal-generating complex includes at least one signal-generating element that is a semiconductor quantum dot (QDs). Various methods are available for attaching quantum dots to the DNA backbone of an aptamer such as, for example, covalent linkage of amine-modified DNA to carboxylated quantum dots and linkage of biotinylated DNA to streptavidin modified quantum dots. See, e.g., Cady, et al. (2007) *J. Mol. Cell. Probes* 21:116-124, which is incorporated herein by reference. For example, carboxy quantum dots (from, e.g., Quantum Dot Corporation, Hayward, Calif., USA) can be attached to an aptamer through a C6 amino modifier placed on either the 5-prime or 3-prime end of the aptamer sequence. For example, streptavidin quantum dots (from, e.g., Quantum Dot Corporation, Hayward, Calif., USA) can be attached to an aptamer through a biotin attached to the 5-prime end of the aptamer sequence.

In an aspect, the aptamer-based signal-generating complex includes a signal-generating element that is a fluorophore, non-limiting examples of which have been describe above herein. The fluorophores can be attached to various linkers that allow for attachment at various sites within the aptamer. For example, 3-prime-DABCYL CPG can be used to place the fluorophore DABCYL at the 3-prime terminus of the aptamer whereas 5-prime-DABCYL phosphoramidite can be used to place DABCYL at the 5-prime terminus of the aptamer (see, e.g., product information at Glen Research, Sterling, Va.). DABCYL deoxythymidine (dT) can be used to place DABCYL within the body of the aptamer sequence. Modifying aptamers with appropriate commercially available fluorophores can be achieved following instructions provided by the respective manufacturer. Alternatively, custom made aptamer-based signaling complexes are available from commercial sources (from, e.g., Biosearch Technologies, Inc., Novato, Calif., USA).

In an aspect, the aptamer-based signal-generating complex can have a signal-generating element in a region of the molecule known to undergo conformational change upon binding a target microbe that leads to an increase in fluorescence intensity. An aptamer of this sort can be selected using an in vitro selection process with fluorescently labeled aptamers. See, e.g., Jhaveri, et al. (2000) *Nature Biotech.* 18:1293-1297, which is incorporated herein by reference. For example, a pool of RNA molecules is generated in which the random sequence region (45-60 residues) is skewed such that one of the residues, uridine, for example, is disproportionately underrepresented. The three to four randomly placed uridine residues are substituted with fluorescein-12-UTP, Cascade Blue-7-UTP, Texas Red-5-UTP, and/or Rhodamine Green-5-UTP during in vitro transcription. The labeled pool of RNA molecules are screened against a target microbe by passing the labeled pool over a column matrix or other matrix to which the target microbe is attached. Those RNA molecules that bind with high affinity to the target component are screened for their fluorescence signaling properties in response to binding of the target microbe. For example, the baseline fluorescence intensity is measured for RNA aptamer molecules labeled with fluorescein-12-UTP (excitation maxima 494 nm, emission maxima 521 nm) or Rhodamine Green-5-UTP (excitation maxima 505 nm, emission maxima 533 nm), for example, then re-measured in response to increasing concentrations of the target component. As such, fluorescent aptamers can be selected that exhibit a 100-200% increase in fluorescence intensity in response to target binding.

In an aspect, the signal-generating complex for FRET-based signaling includes a specific microbe-binding element that is an antibody configured to bind at least one type of microbe and a signal-generating element that includes one or more donor fluorophore and one or more acceptor fluorophore or quencher. For example, the antibody including a donor fluorophore and an acceptor fluorophore or quencher can be configured to undergo a conformational change upon binding a target, e.g., a microbe, causing the distance between the donor fluorophore and the acceptor fluorophore or quencher to shift, the shift leading to a change in measurable fluorescence. See, e.g., Dwarakanath et al. (2004) *Biochem. Biophys. Res. Commun.* 323:739-743, which is incorporated herein by reference. In an aspect, the antibody can be designed to elicit a shift in emission wavelength, for example, in response to binding a microbe. For example, an antibody exhibiting a shift in fluorescent signal in response to binding of a target microbe can be generated by labeling the antibody with a solvent-sensitive fluorophore, e.g., dansyl chloride (5-dimethylaminonaphthalene-1-sulfonyl chloride). See, e.g., Brennan (1999) *J. Fluor.* 9:295-312, which is incorporated herein by reference. In an aspect, the antibody is modified with a fluorescence signal-generating element such that binding of the target microbe to the antibody shields a solvent sensitive fluorescence signal-generating element near the active binding site from a solvent, e.g., water, resulting in a 3-5 fold increase in fluorescence intensity. See, e.g., Bright, et al. (1990) *Anal. Chem.* 62:1065-1069, which is incorporated herein by reference.

In an aspect, the signal-generating complex for FRET-based signaling includes a specific microbe-binding element that is an antibody with a flexible arm. For example, the antibody can include a donor fluorophore near the binding site of a target, e.g., a microbe, as well as a flexible arm containing an analog of the target or part thereof that is labeled with a quencher and recognized by the antibody. See, e.g. U.S. Patent Application 2006/0172318, which is incorporated herein by reference. For example, as the labeled target analog moves into proximity to the labeled active site, a baseline FRET signal can be measured. A measurable change in the FRET signal is detected when the analog is competitively displaced by the actual target. The flexible arm can be composed of DNA, RNA, polymers, protein nucleic acid (PNA), peptides, protein or oligosaccharide. For example, an amino-functionalized DNA arm can be treated with a bifunctional NETS-ester activated Cy3.5 dye to add a fluorescent tag to the flexible arm. The analog of the target is modified with a monoamine and interacted with the bifunctional NETS-ester and attached to the DNA flexible arm. The flexible arm can be attached directly to the antibody through a thiol-maleimide linkage such that the DNA flexible arm is modified with a thiol group at one end and linked via maleimide to one or more cysteine groups on the antibody. Alternatively, the flexible arm can be attached to a protein, for example, that is adjacent to the antibody or to which the antibody is bound.

In an aspect, the signal-generating complex can be configured such that binding of one or more microbes to the specific microbe-binding element operably coupled to the signal-generating element results in a conformational change that can be measured using chemiluminescence resonance energy transfer (CRET). In an aspect, the image-capture device is able to detect luminescence. For example, the interaction of luminol with hydrogen peroxide in the presence of iron or copper and enhanced by horseradish peroxidase results in emitted light. See, e.g., Freeman et al. (2011) *J. Am. Chem. Soc.* 133:11597-11604; Lee et al. (2012) *ACS Nano* 6:2978-2983, which are incorporated herein by reference.

In an aspect, the at least one specific microbe-binding element of the signal-generating complex is chemically coupled to the at least one signal-generating element. In an aspect, the specific microbe-binding element and the signal-generating element are directly associated with one another through chemical cross-linking, non-covalent linking, or synthesis as a single molecule. For example, the signal-generating element may be operably coupled to the specific microbe-binding element through one or more of a chemical cross-link, a streptavidin/biotin interaction, a fusion protein construct, a common substrate, or a combination thereof.

In an aspect, the signal-generating element is conjugated to the specific microbe-binding element using one or more of a cross-linking agent, non-limiting examples of which have been describe above herein. In general, any of a number of cross-linking agents can be used to conjugate an appropriately derivatized signal-generating element to an appropriately derivatized or functionalized specific microbe-binding element. For example, a fluorescent dye, e.g., rhodamine, derivatized with succinimidyl ester (from, e.g., Invitrogen, Carlsbad, Calif.) will react efficiently with primary amines of proteins, e.g., antibodies, to generate a stable fluorescent dye-protein conjugate. As another example, an antibody for use as a specific microbe-binding element can be conjugated with one or more quantum dots via an amine-thiol linkage using amine-derivatized, poly-ethylene glycol coated quantum dots and the amine-thiol crosslinker SMCC using a commercially available kit (Qdot® Antibody Conjugation Kit, Invitrogen, Carlsbad, Calif.). Similarly, various methods are available for attaching quantum dots to a DNA backbone of an aptamer such as, for example, covalent linkage of amine-modified DNA to carboxylated quantum dots. For example, carboxy quantum dots (from, e.g., Quantum Dot Corporation, Hayward, Calif., USA) can be attached to an aptamer through a C6 amino modifier placed on either the 5-prime or 3-prime end of the aptamer sequence. Magnetic beads derivatized with carboxylic acid, amine groups or tosylactivated for cross-linking to proteins and appropriately derivatized oligonucleotides are also commercially available (from, e.g., Dynal Biotech, Brown Deer, Wis.). Quantum dots, fluorescent dyes, and magnetic particles derivatized for cross-linking to antibodies, aptamers or other biomolecules are available from a number of commercial sources (from, e.g., Invitrogen, Carlsbad, Calif.; Seradyn-Thermo Scientific, Indianapolis, Ind.; Sigma-Aldrich, St. Louis, Mo.). Non-limiting examples of homobifunctional, heterobifunctional, and/or photoreactive cross-linking agents have been described above herein.

In an aspect, the at least one specific microbe-binding element is non-covalently lined to the signal-generating element. For example, the signal-generating element can be non-covalently linked to the specific microbe-binding element using one or more interactions between biotin and avidin, streptavidin or derivatives thereof. In an aspect, a biotinylated signal-generating element can be reacted with a biotinylated specific microbe-binding element in the presence of streptavidin to form the signal-generating complex. For example, a biotinylated signal-generating element, e.g., biotin-4-fluorescein (from, e.g., Invitrogen, Carlsbad, Calif.), can be linked to a biotinylated specific microbe-binding element, e.g., a biotinylated antibody, through a streptavidin bridge. An antibody or other protein-based binding component can be biotinylated using an amine reactive biotinylation reagent such as, for example, EZ-Link Sulfo-NHS—SS-Biotin (sulfosuccinimidyl 2-(biotinamido)-ethyl-1,3-dithiopropionate; Pierce-Thermo Scientific, Rockford, Ill., USA; see, e.g., Jaiswal, et al. *Nature Biotech.* 21:47-51, 2003, which is incorporated herein by reference). Similarly, a biotinylated label can be linked to a biotinylated oligonucleotide aptamer through a streptavidin bridge. An aptamer or other nucleotide-based binding component can be biotinylated by introducing a biotinylated nucleotide, e.g., biotin-5-deoxycytidine-5-triphosphate (from, e.g., ChemCyte, Inc., San Diego, Calif.) into the aptamer sequence during in vitro transcription.

In an aspect, the signal-generating element or the specific microbe-binding element of can be modified with streptavidin, avidin, or derivative thereof and directly bound to a biotinylated signal-generating element or a specific microbe-binding element. In an aspect, the signal-generating element is modified with streptavidin and combined with a biotinylated specific microbe-binding element. For example, streptavidin modified quantum dots (available from, e.g., Quantum Dot Corporation, Hayward, Calif., USA) can be attached to an aptamer through a biotin modification to the 5-prime end of the aptamer sequence. See, e.g., Cady et al. (2007) *Mol. Cell. Probes* 21:116-124, which is incorporated herein by reference. Examples of other streptavidin modified fluorescent dyes are available (from, e.g., PerkinElmer, Waltham, Mass.; Alpha Diagnostic Intl. Inc., San Antonio, Tex.). Streptavidin modified magnetic beads are also commercially available (e.g., Dynabeads® MyOne™ Streptavidin, Dynal Biotech, Brown Deer, Wis.). In another aspect, the specific microbe-binding element can contain all or part of the streptavidin protein for use in binding to a biotin modified signal-generating element. For example, cDNA sequence encoding all or part of an antibody or other protein/peptide can be genetically modified to contain all or part of the streptavidin gene using standard cloning procedures, resulting in a streptavidin-antibody fusion protein. See, e.g., Koo, et al. (1998) *Appl. Environ. Microbiol.* 64:2497-2502, which is incorporated herein by reference. The streptavidin modified specific microbe-binding element can subsequently be combined with one or more of a biotinylated signal-generating element.

In an aspect, the signal-generating element can be incorporated into the specific microbe-binding element at the time of synthesis. In an aspect, the signal-generating complex can include a fusion protein with a specific microbe-binding element, e.g., antibody, peptide ligand, or receptor, and a signal-generating element including all or part of green fluorescent protein (GFP) derived from *Aequorea victoria* jellyfish or yellow, red and blue fluorescing derivatives thereof. A number of expression constructs for generating recombinant GFP fusion proteins are available from commercial sources (from, e.g., Invitrogen, Carlsbad, Calif.).

In an aspect, the plurality of signal-generating complexes associated with the inner surface of the skin-covering material are incorporated into a field effect transistor (FET) based biosensor, in which a change in electrical signal is used to detect interaction of one or more microbes with one or more of the plurality of signal-generating complexes. See, e.g., U.S. Pat. No. 7,303,875, which is incorporated herein by reference. In an aspect, the one or more electrical signals are processed to generate one or more optical signals using light-emitting diodes or semiconductor optical amplifier, the one or more optical signals detected by the image-capture device. In an aspect, the signal-generating complex can include carbon nanotubes functionalized with a specific microbe-binding element. See, e.g., Zelada-Guillen, et al., (2009) *Angew. Chem. Int. Ed.*, 48:7334-7337, which is incorporated herein by reference. Single walled carbon nanotubes can act as efficient ion-to-electron transducers in potentiometric analysis. The carbon nanotubes can be functionalized with a specific microbe-binding element, e.g., an oligonucleotide aptamer, configured recognize and bind at least one type of microbe. The specific microbe-binging element is modified with an amine group and covalently immobilized onto a layer of previously carboxylated single-walled carbon nanotubes. The aptamers are self-assembled on the carbon nanotubes through stacking interactions between the purine and pyrimidine bases of the oligonucleotide aptamers and the walls of the carbon nanotubes. Upon microbe binding to the aptamer, the aptamers change conformation, separating the phosphate groups of the aptamer from the side-walls of the carbon nanotubes and inducing a charge change to the carbon nanotube and recorded potential.

In an aspect, the signal-generating complex can include one or more microcantilevers configured to detect changes in cantilever bending or vibrational frequency in response to binding of one or more microbes to the surface of the microcantilever. In an aspect, the inner surface of the skin-covering material can include a plurality of biochips including microcantilever bi-material formed from gold and silicon, as sensing elements. See, e.g. Vashist (2007) *J. Nanotech Online* 3:DO: 10.2240/azojono0115, which is incorporated herein by reference. The gold component of the microcantilever can be functionalized with one or more specific microbe-binding elements, e.g., aptamer, antibodies, or other microbe binding element. A number of microcantilever deflection detection methods can be used to measure microbe binding including, among other things, optical deflection detection, interferometry deflection detection, optical diffraction grating deflection detection, and charge coupled device detection. In some aspects, the one or more microcantilever can be a nanocantilever with nanoscale components. The one or more microcantilevers and/or nanocantilevers can be arranged into arrays for detection of one or more target cells. Both microcantilevers and nanocantilevers can find utility in microelectromechnical systems (MEMS) and/or nanoelectromechanical systems (NEMS).

In an aspect, the signal-generating complex can include one or more surface plasmon resonance sensors for detecting changes in the refractive index on a sensor surface in response to changes in molecules bound on the sensor surface. In an aspect, the inner surface of the skin-covering material is coated with a thin film of metal, for example, gold. In an aspect, the surface includes a matrix to which is immobilized a plurality of specific microbe-binding elements. The sensor is illuminated by monochromatic light. Resonance occurs at a specific angle of incident light. The resonance angle depends on the refractive index in the vicinity of the surface, which is dependent upon the concentration of microbes on the surface. See, e.g., Raghavan & Bjorkman (1995) *Structure* 3:331-333, which is incorporated herein by reference.

In an aspect, the skin-covering material is reusable. In an aspect, the plurality of signal-generating complexes including at least one signal-generating element operably coupled to at least one specific microbe-binding element are included in a renewable layer on the inner surface of the skin-covering material. For example, the plurality of signal-generating complexes including at least one signal-generating element operably coupled to at least one specific microbe-binding element may be applied to the inner surface of the skin-covering material as a liquid, gel, or spray, rinsed off the skin-covering material after a first use, and reapplied for subsequent uses. In an aspect, at least one of the signal-generating element, the specific microbe-binding element, or both are renewable. For example, a change in pH, ionic strength, temperature, or combinations thereof may be used to non-destructively remove microbes bound to the specific microbe-binding element. In this way, a single skin-covering material can be prepared for an individual and used multiple times with regenerated or replaced signal-generating complexes.

Systems Including Skin-Covering Material

FIG. 7 illustrates aspects of a system for assessing the microbiota of skin including a skin-covering material. System 700 includes components configured to sample and report to a user the identity and the spatial distribution of microbes contributing to the microbiota on a skin surface of an individual. System 700 includes skin-covering material 710, an image-capture device 720, and a computing device 730.

Skin-covering material 710 includes an inner surface and an outer surface, the inner surface substantially conforming in shape to a topography of a skin surface of individual 740. In an aspect, skin-covering material 710 is configured to be in physical contact with the skin surface of individual 740 and to interact, e.g., bind, at least one type of microbe from the skin surface of individual 740.

The inner surface of skin-covering material 710 further includes a plurality of signal-generating complexes, one or more of the plurality of signal-generating complexes configured to emit one or more signals in response to at least one type of microbe. In an aspect, skin-covering material 710 can include a pre-formed skin-covering material, e.g., as illustrated in FIG. 1. Non-limiting aspects of a pre-formed skin-covering have been described above herein. In an aspect, skin-covering material 710 can include a peelable skin-covering material, e.g., as illustrated in FIG. 2. Non-limiting aspects of a peelable skin-covering material have been described above herein. In an aspect, skin-covering material 710 can include a plurality of signal-generating complexes, each of the signal-generating complexes including at least one signal-generating element operably coupled to at least one specific microbe-binding element, e.g., as illustrated in FIG. 3 and in FIG. 5.

In an aspect, skin-covering material 710 includes a plurality of signal-generating complexes of at least one first type including at least one signal-generating element of a first type operably coupled to at least one specific microbe-binding element of a first type, the at least one signal-generating element of the first type configured to emit one or more signals of a first type in response to at least one first type of microbe bound to the operably coupled at least one specific microbe-binding element of the first type and a plurality of signal-generating complexes of at least one second type including at least one signal-generating element of a second type operably coupled to at least one specific microbe-binding element of a second type, the at least one signal-generating element of the second type configured to emit one or more signals for a second type in response to at least one second type of microbe bound to the operably coupled at least one specific microbe-binding element of the second type, e.g., as illustrated in FIG. 4 and FIG. 6. In an aspect, the at least one first type of microbe differs from the at least one second type of microbe. In an aspect, the one or more signals of the first type differ from the one or more signals of the second type.

System 700 includes image-capture device 720. Image-capture device 720 includes circuitry to capture at least one image of the inner surface of skin-covering material 710, the at least one image including one or more signals emitted from one or more of the plurality of signal-generating complexes and to transform the captured at least one image into a digital output including information associated with at least one property and a spatial distribution of the imaged one or more signals. In an aspect, image-capture device 720 includes an energy emitting mechanism that emits directed energy 750, excitation energy, which elicits one or more signals 760, e.g., emission energy, from one or more of the plurality of signal-generating complexes associated with skin-covering material 710. In an aspect, image-capture device 720 includes at least one camera. In an aspect, image-capture device 720 includes at least one scanning device. The at least one scanning device can include at least one of a passive scanning device, an active scanning device, or a three-dimensional scanning device. Other non-limiting examples of scanning devices include at least one of an optical scanning device, a fluorescence scanning device, an acoustic scanning device, an electromagnetic scanning device, a spectrometer, or a spectrophotometer.

System 700 further includes computing device 730. Computing device 730 includes a processor and is operably coupled to image-capture device 720 through a communication link 715. Communication link 715 can include at least one of a wireless communication link, e.g., Bluetooth or other radio transmission link, or a wired communication link, e.g., an electrical link. Computing device 730 includes circuitry configured to receive the digital output from image-capture device 720 including the information associated with the at least one property and the spatial distribution of the imaged one or more signals emitted from the one or more of the plurality of signal-generating complexes in response to the at least one microbe, compare the properties of the imaged one or more signals emitted from the one or more of the plurality of signal-generating complexes with a database of emitted signals of reference signal-generating complexes, and generate digital spatial profile 770 of the at least one type of microbe based on the spatial distribution of the imaged one or more signals emitted from the one or more of the plurality of signal-generating complexes. In an aspect, computing device 730 further includes circuitry to generate a digital alignment 780 of digital spatial profile 770 with a digital image of a skin surface of individual 740. Digital alignment 780 can be reported to a user of the system, e.g., individual 740 or another individual, to aid in determining a recommended treatment regimen to maintain or alter the current types and spatial distribution of microbes on the skin surface of the individual.

Image-Capture Device

Returning to FIG. 7, system 700 for assessing the microbiota of the skin surface of an individual includes image-capture device 720 including circuitry configured to capture at least one image of the inner surface of skin-covering material 710. In an aspect, image-capture device 720 includes an energy-emitting mechanism and circuitry to scan the inner surface of skin-covering material 710 with directed energy 750 to detect one or more signals 760 emitted from the inner surface of skin-covering 710 and to transform the one or more detected signals into a digital output for receipt by computing device 730. The digital output includes information associated with at least one property and a spatial distribution of the detected one or more signals emitted from the one or more of the plurality of signal-generating complexes.

In an aspect, the at least one property of the one or more signals emitted from the one or more of the plurality of signal-generating complexes in response to the at least one type of microbe includes at least one optical property, fluorescence property, acoustic property, electrical property, magnetic property, or electromagnetic property. In an aspect, the at least one property of the one or more signals emitted from the at least one of the plurality of the at least one type of signal-generating element includes at least one of wavelength, frequency, or amplitude. The one or more signals generated by the plurality of the at least one type of signal-generating element can be detected by image-capture device 720 using any of a number of imaging or optical methods including but not limited to light scattering, electrical impedance, infrared spectroscopy, acoustic imaging, thermal imaging, photothermal imaging, dark field, visible light absorption and refraction, and autofluorescence. In an aspect, the image-capture device measures the absorption, emission, fluorescence, luminescence, chemiluminescence, and/or phosphorescence of the one or more signal-generating complexes. See, e.g., Doornbos et al. (1993) *Cytometry* 14:589-594; Gao et al. Proceedings of the 25$^{th}$ Annual International Conference of the IEEE EMBS, Cancun, Mexico, Sep. 17-21, 2003; Oberreuter et al. (2002) *Int. J. Syst. Evol. Microbiol.* 52:91-100; Baddour et al. (2002) Ultrasonics Symposium IEEE 2:1639-1644; Zharov et al. (2006) *J. Cell. Biochem.* 97:916-932; Zharov et al. (2006) *J.*

*Biomed. Opt.* 11:054034-1-4; Koenig et al. (1994) *J. Fluoresc.* 4:17-40; each of which is incorporated herein by reference.

In an aspect, image-capture device 720 includes at least one camera, e.g., a digital camera, configured to capture one or more images. In an aspect, the at least one camera may capture one or more images in the visible spectrum. In an aspect, the at least one camera may capture one or more images in other portions of the electromagnetic spectrum, e.g., infrared or ultraviolet. In an aspect, the at least one camera may capture emitted and/or reflected light. The image-capture device can include one or more electronic image sensors, e.g., photodiodes, photoresistors, charge-coupled devices (CCD), and/or complementary metal oxide semiconductor (CMOS) devices. For example, a CCD camera system can be used to image luminescence, e.g., chemiluminescence, on a solid substrate (e.g., GeneGnome5, Syngene USA, Fredrick Md.). In an aspect, the image-capture device includes a single-shot capture device with one CCD with a Bayer filter mosaic or three separate image sensors, which are exposed to the same image via a beam splitter. In an aspect, the image-capture device includes a multi-shot capture device. For example, a single CCD sensor may obtain additive color information by capturing an image three times, each with a different filter (e.g., red, green, and blue). For example, the CCD sensor may capture images as it is moved to various locations on the focal plane and a high resolution composite image "stitched" together. In an aspect, the image-capture device includes a scanning device in which the sensor moves across the focal plane. For example, the camera can include a rotating line camera with a linear CCD array to assemble a high resolution digital image as the camera rotates. Camera can include an area array of CCD or CMOS sensors. Camera can include a linear array of CCD (monochrome) or 3-strip CCD with color filters.

In an aspect, image-capture device 720 includes at least one scanning device. Non-limiting examples of scanners include optical scanners, fluorescence scanners, acoustic scanners, electrical scanners, electromagnetic scanners, or magnetic scanners. In an aspect, the scanner includes an energy-emitting mechanism, e.g., a light source or a laser, and circuitry to scan the inner surface of a skin-covering material with directed energy, e.g., light of a specified wavelength, to detect one or more signals emitted from the inner surface of skin-covering material and to transform the one or more detected signals into a digital output. In an aspect, the one or more signals emitted from one or more of the plurality of signal-generating complexes are indicative of the identity and/or spatial distribution of at least one type of microbe associated with the skin surface of the individual.

In an aspect, image-capture device 720 includes a colorimetric scanner configured to detect color emitted from one or more of the plurality of signal-generating complexes in response to at least one type of microbe. For example, the colored signal may arise from a chromogenic reaction, examples of which have been described above herein. An example of a commercially available colorimetric scanner includes SpotWare™ Colorimetric Microarray Scanners (Arrayit® Corporation, Sunnyvale, Calif.).

In an aspect, image-capture device 720 includes a fluorescence scanning device. In an aspect, the fluorescence scanning device can include fixed excitation/emission wavelengths based on the use of standard commercially available fluorescent dyes in the green, red, and near infrared wavelengths. For example, the fluorescence scanning device can include a two color scanner for scanning at two distinct wavelengths or wavelength bands. In an aspect, the fluorescence scanning device can include adjustable excitation/emission wavelengths, e.g., with one or more excitation sources and filters to adjust the excitation/emission wavelengths. Non-limiting examples of fluorescent scanners include Fluoroimage 595 or ImageQuant (GE Healthcare Life Sciences, Piscataway, N.J.), Tecan fluorescence scanners (Invitrogen, Carlsbad, Calif.), SureScan Microarray Scanner (Agilent Technologies, Inc., Santa Clara, Calif.), InnoScan® (Innopsys Inc., Chicago, Ill.). Additional examples include fluorescence scanners with motorized stage for line scans across a surface (see, e.g., U.S. Pat. No. 6,371,370 or 8,385,619, which are incorporated herein by reference), and "stitching together" several image blocks to generate larger image (see, e.g., U.S. Pat. No. 8,041,147, which is incorporated herein by reference).

In an aspect, image-capture device 720 can be configured to detect a fluorescent response at a single wavelength of electromagnetic energy, at two wavelengths of electromagnetic energy, at multiple wavelengths of electromagnetic energy, or over extended-spectrum electromagnetic energy. In an aspect, the image-capture device can be configured to detect excitation energy. In an aspect, the image-capture device can be configured to detect a cumulative (optionally fluorescent) response over a time interval. In an aspect, the image-capture device can be configured to detect a (optionally fluorescent) response at a specific time interval and/or at a specific time. In an aspect, the image-capture device can be configured to detect a time-dependent (optionally fluorescent) response. In illustrative examples, the cumulative response is determined over milliseconds, seconds, and/or minutes following excitation. In an aspect, the response is detected over millisecond, second, and/or minute time intervals following excitation. In an aspect, the response is detected approximately femtoseconds, picoseconds, nanoseconds, milliseconds, seconds, and/or minutes after excitation.

In an aspect, image-capture device 720 includes one or more imaging sensors including, but not limited to, one or more piezo transducers, one or more MEMS device, one or more cavity resonators, one or more magneto resistive sensors, one or more magnetic field sensors, and/or one or more thermal sensors. In an aspect, image-capture device 720 includes one or more electromagnetic energy sensors, one or more acoustic sensors, one or more photodetectors, one or more radiofrequency antennae, one or more magnetic energy sensors, one or more thermal sensors, and/or one or more electrical energy sensors. The one or more electromagnetic energy sensors can include one or more optical sensors including, but not limit to, sensors configured to detect near infrared, ultraviolet, fluorescence, and/or visual light emitted by the at least one type of signal-generating element.

In an aspect, image-capture device 720 includes components for micro-scanning in which a single CCD sensor with a Bayer filter is moved over the focus plane of the lens to "stitch" together a higher resolution image than the CCD would allow otherwise. In an aspect, the micro-scanning device includes a micro laser scanning device. See, e.g., Seidl et al. (2006) *International Society for Photogrammetry and Remote Sensing*. Volume XXXVI Part 5. Sep. 25-27, 2006, Dresden Germany.

In an aspect, image-capture device 720 includes a three-dimensional scanning device. Non-limiting examples of three-dimensional scanning devices include NextEngine 3D Scanner (NextEngine, Inc., Santa Monica, Calif.), Handyscan 3D (Creaform USA Inc., Newark, Del.), or Konica Minolta 3D scanners (Konica Minolta, Ramsey, N.J.).

In an aspect, image-capture device 720 includes a confocal laser scanner. In an aspect, the confocal laser scanner can include a handheld confocal laser scanning microscope (e.g., VIVASCOPE 3000, MAVIG GmbH, Munich, Germany). In an aspect, the confocal laser scanner includes a MEMS confocal laser scanner. See, e.g., Murakami et al. (2003) *The 12th International Conference on Solid State Sensors, Actuators and Microsystems*, Boston, Jun. 8-12, 2003, pp. 587-590, which is incorporated herein by reference.

In an aspect, image-capture device 720 includes a light source and a detector for measuring reflected and/or absorbed light. In an aspect, the image-capture device measures changes in refractive index on the surface of the skin-covering material. The inner surface can be illuminated with a light source. Resonance occurs at a specific angle of incident light. See, e.g., Barlen, et al. (2007) *Sensors*, 7:1427-1446; and Kashyap & Nemova (2009) *J. Sensors*: Article ID 645162, which are incorporated herein by reference.

In an aspect, image-capture device 720 includes a spectrometer or spectrophotometer. In an aspect, the spectrophotometer includes a fiber optic spectrophotometer (from, e.g., Ocean Optics, Dunedin Fla.). In an aspect, the image-capture device includes a means of vibrational spectroscopy. Examples of vibrational spectroscopy include, but are not limited to, Fourier transform infrared (FTIR) spectroscopy and micro-Raman spectroscopy. Raman spectroscopy can further include UV-resonance Raman spectroscopy, surface enhanced Raman scattering, or tip-enhanced Raman scattering. See, e.g., Harz et al. (2009) *Cytometry A* 75:104-113, which is incorporated herein by reference.

In an aspect, image-capture device 720 includes a light source, a digital projector, a CCD camera and a computing device for image-processing for spatial frequency domain imaging, a wide field optical technique. In an aspect, image-capture device 720 includes a lens-free imaging system. See, e.g., Kim et al. (2012) *J. Lab. Automation* 17:43-49, which is incorporated herein by reference. In an aspect, one or more of the plurality of signal-generating complexes include one or more label-free optical biosensors that incorporate other optical methodologies, e.g., interferometers, waveguides, fiber gratings, ring resonators, and photonic crystals. See, e.g., Fan, et al. (2008) *Anal. Chim. Acta* 620:8-26, 2008, which is incorporated herein by reference.

In an aspect, image-capture device 720 includes a type of flatbed commercial scanner. For example, a flatbed commercial scanner can be used to image visible color emitted from one or more of the plurality of signal-generating complexes in response to at least one type of microbe. In an aspect, a commercial flatbed scanner can be combined with a laser-directed energy source and one or more lens to create a gigapixel inline digital holographic microscope capable of scanning a 297 mm by 210 mm area, as described in Shimobaba et al. (2013) *Optical Society of America*. arXiv: 1305.6084v1 [physics.optics] 27 May 2013, which is incorporated herein by reference. In an aspect, the scanner includes a mechanical means for feeding the skin-covering material into the scanning device so as to scan the inner surface of the skin-covering material in parts.

In an aspect, image-capture device 720 can capture radioactivity emitted from a signal-generating complex that is radioactive. Examples of methods for detecting radioactivity include, but are not limited to, gas-filled tube detectors, e.g., Geiger counters; scintillation crystal detectors; and solid-state semiconductor detectors. In an aspect, the one or more radioactivity sensors are one or more of a scintillation crystal detector made from a material that fluoresces or emits light when hit by radiation particles. The fluorescence or light can be measured using one or more of a light capture device, e.g., a photomultiplier or photodiode. In an aspect, the one or more radioactivity sensors are one or more of a microdosimeter. A microdosimeter for wireless measurement of radioactivity in vivo has been described and is configured to detect ionizing radiation using a parallel plate capacitor to form a passive LC resonator. See, e.g., Son & Ziaie. *IEEE Trans. Biomed. Eng.* 55:1772-1775, 2008, which is incorporated herein by reference.

In an aspect, image-capture device 720 can capture magnetic signals emitted from a signal-generating complex that is magnetic. In an aspect, the image-capture device can include one or more MEMS magnetic sensors such as described in Lee, et al. Magnetics Conference, 2006. INTERMAG 2006. IEEE International, which is incorporated herein by reference.

In an aspect, image-capture device 720 can capture one or more signals emitted or reflected directly from the at least one type of microbe bound to the at least one specific microbe-binding element of the signal-generating complex. In an aspect, the one or more signals emitted or reflected directly from the at least one type of microbe can be used to complement the information received from the signal-generating complexes, e.g., conformation of the identity of the type of microbe interacting with the signal-generating complex. In an aspect, the one or more signals emitted or reflected from the at least one type of microbe are representative of one or more properties of the at least one type of microbe. The one or more properties can include one or more inherent properties or characteristics of the at least one type of microbe that are measureable by the image-capture device. In an aspect, the one or more properties of the at least one type of microbe can include at least one of an optical property, autofluorescence property, an infrared spectral property, a reflective property, a light scattering property, or an opacity property of the at least one type of microbe. In an aspect, the one or more properties of the at least one type of microbe can include one or more of a size, a morphological property, or a physical feature. For example, the image-capture device can be configured to detect by optical or other means the shape, outline, and/or periphery of the at least one type of microbe on the inner surface of the skin-covering material.

In an aspect, image-capture device 720 includes circuitry configured to capture at least one image of at least one first portion of the inner surface of skin-covering material 710 and at least one second portion of the inner surface of skin-covering material 710 adjacent to the at least one first portion, and generate a composite image including the at least one image of the at least first portion of the inner surface of skin-covering material 710 and the at least one image of the at least one second portion of the inner surface of skin-covering material 710. In an aspect, image-capture device 720 includes a feeding mechanism and an imaging surface sized to accommodate at least a portion of skin-covering material 710, wherein the feeding mechanism is configured to feed in the at least a portion of skin-covering material 710 onto the imaging surface. For example, the feeding mechanism can include one or more rollers configured to feed at least a portion of a skin-covering material into an imaging surface associated with the image-capture device. For example, the feeding mechanism may include aspects of a paper feeding mechanism, e.g., including pickup and feed rollers. In an aspect, image-capture device 720 may further include a feeding mechanism for removing the skin-covering material 710 from the imaging surface. For example, image-capture device 720 may have an input feeding mechanism on one side of the device and an output feeding mechanism on another side of the device. For example, image-capture device 720 may include a feeding mechanism, e.g., rollers, that rotate one direction to bring the skin-covering material into the device and that rotate in the opposite direction to push the skin-covering material out of the device.

In an aspect, image-capture device 720 includes a hand-held image-capture device. For example, image-capture device 720 can include a hand-held camera. In an aspect, image-capture device 720 and computing device 730 including the processor are incorporated into a single unit. For example, image-capture device 720 and computing device 730 can be incorporated into a personal electronic device, e.g., a smart phone device. In an aspect, image-capture device 720 is in wireless communication with computing device 730. In an aspect, image-capture device 720 and computing device 730 including the processor are incorporated into an interactive kiosk.

Returning to FIG. 7, system 700 further includes computing device 730 including a processor and operably coupled to image-capture device 720. Computing device 730 can take various forms or be part of an object, and can include, but not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, or any other like device that takes information as an input and gives it back to the end-users. Computing device 730 can include a digital single processor, ASIC, microprocessor, or other type of processor operating on a system such as a personal computer, server, a router, of other device capable of processing data including network interconnection device. In an aspect, computing device 730 and image-capture device 720 are incorporated into a single unit. In an aspect, computing device 730 is part of a kiosk.

Computing device 730 further includes circuitry configured to receive the digital output from image-capture device 720 including the information associated with the at least one property and the spatial distribution of the imaged one or more signals emitted from the one or more of the plurality of signal-generating complexes in response to the at least one type of microbe; compare the properties of the imaged one or more signals emitted from the one or more of the plurality of signal-generating complexes in response to the at least one type of microbe with a database of emitted signals of reference signal-generating complexes; and generate digital spatial profile 770 of the at least one type of microbe based on the spatial distribution of the imaged one or more signals emitted from the one or more of the plurality of signal-generating complexes in response to the at least one type of microbe.

In an aspect, computing device 730 includes circuitry configured to verify an identity of the at least one type of microbe. In an aspect, computing device 730 includes circuitry configured to compare the properties of the imaged one or more signals emitted from the one or more of the plurality of signal-generating complexes with the database of emitted signals of reference signal-generating complexes. In an aspect, the database includes signal properties for reference signal-generating complexes that emit signals in response to at least one specific microbe. For example, computing device 730 can include a database containing a reference library of signal-generating complexes and associated autofluorescence properties at given excitation wavelengths. For example, computing device 730 can include a database containing a reference library of signal-generating complexes and associated optical, fluorescence, magnetic, acoustic, infrared spectral, electromagnetic, or electrical properties. For example, computing device 730 can include a database containing a reference library of signal-generating complexes and associated properties such as wavelength, frequency, and/or amplitude. In an aspect, computing device 730 includes one or more algorithms to process the digital output provided by the image-capture device. For example, the one or more algorithms can include an algorithm for assessing the number of microbes in an image field. See, e.g., Selinummi et al., (2005) *BioTechniques* 29:859-863, which is incorporated herein by reference.

In an aspect, the database of emitted signals of reference signal-generating complexes includes emitted signals of matched sets of specific signal-generating elements operably coupled to specific microbe-binding elements that form specific signal-generating complexes and are configured to emit a specific signal in response to a specific type of microbe. For example, computing device 730 can include a database or lookup table including reference signal properties for matched sets of signal-generating elements and specific microbe-binding elements. For example, the database or lookup table can include excitation and emission spectra for one or more fluorescent signal-generating elements. For example, the database can include color wavelength information for chromogenic signal-generating elements. For example, the database can include radio frequencies for RFID tags. For example, the database can include infrared or FTIR spectral information for specific signal-generating elements. In an aspect, the database includes signal properties for known signal-generating elements operably linked to known specific microbe-binding elements such that if a specific signal is detected, the system will know that a specific microbe is present. For example, the database may include signal properties for Cy3 (approximately 570 nm emission) operably linked to an antibody against *Propionibacterium acnes* and signal properties for Cy5 (approximately 670 nm emission) operably linked to an antibody against *Staphylococcus aureus*. Detection of yellow-green signal properties would be indicative of Cy3 and therefore the presence of *Propionibacterium acnes* while detection of red signal properties would be indicative of Cy5 and therefore the presence of *Staphylococcus aureus*.

In an aspect, computing device 730 includes circuitry configured to compare the generated digital spatial profile with a reference digital spatial profile. In an aspect, the reference digital spatial profile includes a historical digital spatial profile previously acquired for the individual. For example, the reference digital spatial profile can include a historical digital spatial profile previously acquired for the individual at a previous point in time, e.g., 1 to 24 hours previous, 1 to 30 days previous, 1 to 12 months previous, and/or 1 to 30 years previous. For example, the reference digital spatial profile can include a historical digital spatial profile previously acquired for the individual before and/or after initiating a treatment regimen. For example, the reference digital spatial profile can include a historical digital spatial profile previously acquired for the individual before and/or after the onset of a skin condition, e.g., acne, psoriasis, or eczema. In an aspect, the reference digital spatial profile includes one or more digital spatial profiles from at least one other individual. For example, the reference digital spatial profile may represent an averaged "normal" digital spatial profile. For example, the reference digital spatial profile may represent an optimal profile based on an averaged "normal." For example, the reference digital spatial profile may represent the digital spatial profile of a celebrity or other such individual whose skin the individual admires and wishes to emulate by attaining the same microbiotic profile.

In an aspect, computing device 730 includes circuitry configured to generate a recommended treatment regimen based on the comparison of the generated digital spatial profile with the reference digital spatial profile. For example, comparing a recent digital spatial profile with a historical digital spatial profile may indicate an increase in an undesirable type of bacteria and as such the computing device can generate a recommended treatment regimen including antibiotic use, changes in diet, use of probiotics, and/or cleansing recommendations. In an aspect, the recommended treatment regimen is designed to maintain and/or modify the type and/or distribution of microbes on the skin surface of the individual. The recommended treatment regimen can include use of an anti-microbial agent, e.g., antibiotic or fungicide; use of a cleaning regimen, e.g., type of soap, abrasive, astringent, and the like; use of a probiotic, e.g., adding back bacteria or other microbes that contribute to a healthy skin condition; change in a diet, e.g., increased fluids, omitting certain foods, and the like; and/or recommended cosmetic products, e.g., non-comedogenic products, microbe-compatible foundations or other make-up products, moisturizers or other skin creams, and the like. Computing device 730 further includes circuitry to report to a user the recommended treatment regimen.

In an aspect, computing device 730 further includes circuitry configured to generate a digital alignment of the generated digital spatial profile with a digital image of the skin surface of the individual covered by the inner surface of the skin-covering material. One or more digital images of the skin surface of the individual can be captured, e.g., with a digital camera, before and/or after placement of the skin-covering material onto the skin surface. One or more registration marks on the skin-covering material may be used to register the skin-covering material relative to landmarks on the skin surface of the individual, the landmarks incorporated into the digital image of the skin surface. One or more registration marks on the skin-covering material can be used to align with one or more landmarks on the skin surface. The one or more landmarks on the skin surface can include one or more of pigmentation, pigmented areas, tattoos, skin texture patterns, blemishes, scars, anatomical features, or subsurface blood vessels associated with the skin surface. In an aspect, the one or more registration marks are incorporated into the manufacture of the skin-covering material based on the presence of landmarks in the one or more digital images of the skin surface used to form the skin-covering material. In an aspect, the one or more registration marks can be added, e.g., with a pen or other marking device, while the skin-covering material is on the skin-surface of the individual.

In an aspect, computing device 730 includes circuitry configured to detect one or more features depicted in the digital images, e.g., the physical landmarks, and match these features with features in the digital spatial profile, e.g., the registration marks. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. Computing device 730 includes circuitry to match the features detected in the one or more images of skin surface of the individual with features in the digital spatial profile using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser Image Vision Computing (2003) 21:977-1000.

In an aspect, computing device 730 further includes circuitry configured to generate a personalized microbe profile from the generated digital alignment, the personalized microbe profile including at least one of the identity of the at least one type of microbe and a spatial distribution of the identified at least one type of microbe on the skin surface of the individual. In an aspect, computing device 730 includes circuitry to report to a user the generated personalized microbe profile. In an aspect, the user includes the individual, e.g., the individual for whom the personalized microbe profile is generated. In an aspect, the user includes a service-provider, e.g., a medical professional or cosmetologist who performs the steps to generate the personalized microbe profile for an individual. In an aspect, the user includes an interested third party, e.g., the manufacturer of the skin-covering material and/or system, a third-party payer such as an insurance company, or a researcher.

In an aspect, computing device 730 includes circuitry configured to provide a visual representation of the personalized microbe profile on a display. In an aspect, the display is operably coupled to computing device 730. For example, a visual representation of an individual's personalized microbe profile may be shown on a display of a computing device in an office of a medical professional or cosmetologist. For example, a visual representation of an individual's personalized microbe profile may be shown on display of a kiosk or at a cosmetic counter. In an aspect, the display is operably coupled to a second computing device. For example, the personalized microbe profile may be available on a display associated with a hand-held device, e.g., a personal computing device such as a smartphone device.

In an aspect, computing device 730 includes circuitry configured to provide a printout to a user, the printout including the personalized microbe profile. The printout can include textual description and/or visual representation of the personalized microbe profile. For example, the printout may provide the personalized microbe profile as a textual description, e.g., identification of the at least one type of microbe on the skin surface of the individual and generally where the microbes are distributed, e.g., the nose area, the "T-zone," the forehead, and the like. For example, the printout may provide the personalized microbe profile as a hardcopy version of the visual representation shown on a display. In an aspect, the printout may further include a recommended treatment regimen intended to maintain and/or modify the types and distribution of microbes on the skin surface of the individual.

In an aspect, computing device 730 includes circuitry configured to export information regarding the personalized microbe profile to at least one second computing device. For example, the personalized microbe profile may be generated on a first computing device, e.g., in a service-provider's office, and subsequently downloaded to one or more computing devices accessible by the individual, e.g., a home computer or a smartphone device. For example, the personalized microbe profile may be generated by a computing device associated with a kiosk and subsequently downloaded to one or more computing devices accessible by the individual. In an aspect, the at least one second computing device is associated with a retailer capable of providing a recommended treatment regimen, e.g., a pharmacy, a cosmetic counter, or other retailer. In an aspect, the at least one second computing device is associated with a manufacturer, e.g., the manufacturer of the skin-covering material and/or a component of a treatment regimen. In an aspect, the at least one second computing device is associated with a third party payer, e.g., an insurance company. In an aspect, the at least one second computing device is associated with a research group.

In an aspect, computing device 730 includes circuitry configured to generate a recommended treatment regimen based on an identity and a spatial distribution of the at least one type of microbe on the skin surface of the individual; and report the generated recommended treatment regimen to a user. In an aspect, the recommended treatment regimen is designed to maintain and/or modify the type and/or distribution of microbes on the skin surface of the individual. For example, the circuitry can be configured to generate a recommended treatment regimen including an antimicrobial treatment based on the types of microbes present, e.g., antibiotics for bacteria, fungicide for fungus, or antiviral for a virus. For example, the circuitry can be configured to generate a recommended treatment regimen including a type of skin cleaning process, e.g., a type of soap or antiseptic rinse, based on the identity and the distribution of the at least one type of microbe. For example, the circuitry can be configured to generate a recommended treatment regimen including one or more probiotics or prebiotics to alter the microbe profile on the skin surface, e.g., to balance beneficial microbes against harmful microbes. For example, the circuitry can be configured to generate a recommended treatment regimen including a certain type of cosmetic product that is compatible with the microbes present, e.g., helps to maintain beneficial microbes but discourages harmful microbes and can include probiotics and/or prebiotics. For example, the circuitry can be configured to generate a recommended treatment regimen including one or more medicaments, e.g., hormone creams, oral hormones, or retinoid creams. Non-limiting examples of components of a recommended treatment regimen include antimicrobial agents, cleansing products, cosmetic products, probiotics, prebiotics, medicaments, procedures (e.g., shaving or not in sensitive areas, applying warm compresses to open pores, use of a pore-opening or cleaning device, abrasion, and the like), and changes in diet. In an aspect, the circuitry can be configured to alert the individual as to whether the identity and the spatial distribution of the at least one type of microbe warrants discussion with a medical professional. In an aspect, the computing device includes circuitry configured to report to the user the recommended treatment regimen including via a display, a printout, or exportation of data to another device, e.g., a personal handheld device.

In an aspect, system 700 further includes at least one enhancing component to enhance binding of the at least one type of microbe to the one or more of the plurality of signal-generating complexes. In an aspect, the enhancing component includes a thermal component, a vacuum component, a humidity component, a chemical component, or a pressure component. For example, a thermal component, e.g., heat at a temperature compatible with skin, may be used to open skin pores to allow access for sampling by the skin-covering material. For example, a vacuum component associated with the skin-covering material may be used to suction the at least one type of microbe from the skin surface and onto the inner surface of the skin-covering material. For example, a humidity component, e.g., pre-wetting the face or the skin-covering material, may be used to create an aqueous environment for interaction with the signal-generating complexes. For example, a pressure component, e.g., applying equal pressure to the skin-covering material while it is on the skin surface of the individual may ensure equal capture and representation of microbes from the skin surface.

In an aspect, the at least one enhancing component includes a chemical enhancing component, non-limiting examples of which include at least one of a skin-softener, a detergent, or a lysing compound. For example, the chemical enhancing component can be applied to the skin surface prior to applying the skin-covering material. For example, the chemical enhancing component may be included in the inner surface of the skin-covering material and makes contact with the skin upon applying the skin-covering material to the skin surface. In general, the chemical enhancing component either enhances capture of microbes from the skin surface, e.g., enhancing accessibility, or enhances detection of one or more biomolecules associated with the microbes. In an aspect, the enhancing component includes at least one skin-softener, non-limiting examples of which include emollients, moisturizers, lubricants, and/or oils.

In an aspect, the enhancing component includes a lysing compound to lyse the one or more microbes either directly on the skin surface or on the inner surface of the skin-covering material. The lysing compound allows biomolecules, e.g., proteins or nucleic acids, in the interior of the microbe to be more accessible for detection. Non-limiting examples of lysing compounds includes urea, enzymes for lysing bacterial cell walls (e.g., lysozyme, labiase, lysostaphin, mutanolysis, achromopeptidase), and enzymes for lysing fungal, e.g., yeast, cell walls (e.g., kitalase, lyticase, chitinase, glucanase). One or more detergents or surfactants may also be used for lysing cells, non-limiting examples of which include nonionic detergents, e.g., Triton X-100, Nonidet P-40, Tween 20; zwitterionic detergents, e.g., CHAPS; and ionic detergents, e.g., sodium dodecyl sulfate.

Figure 8:
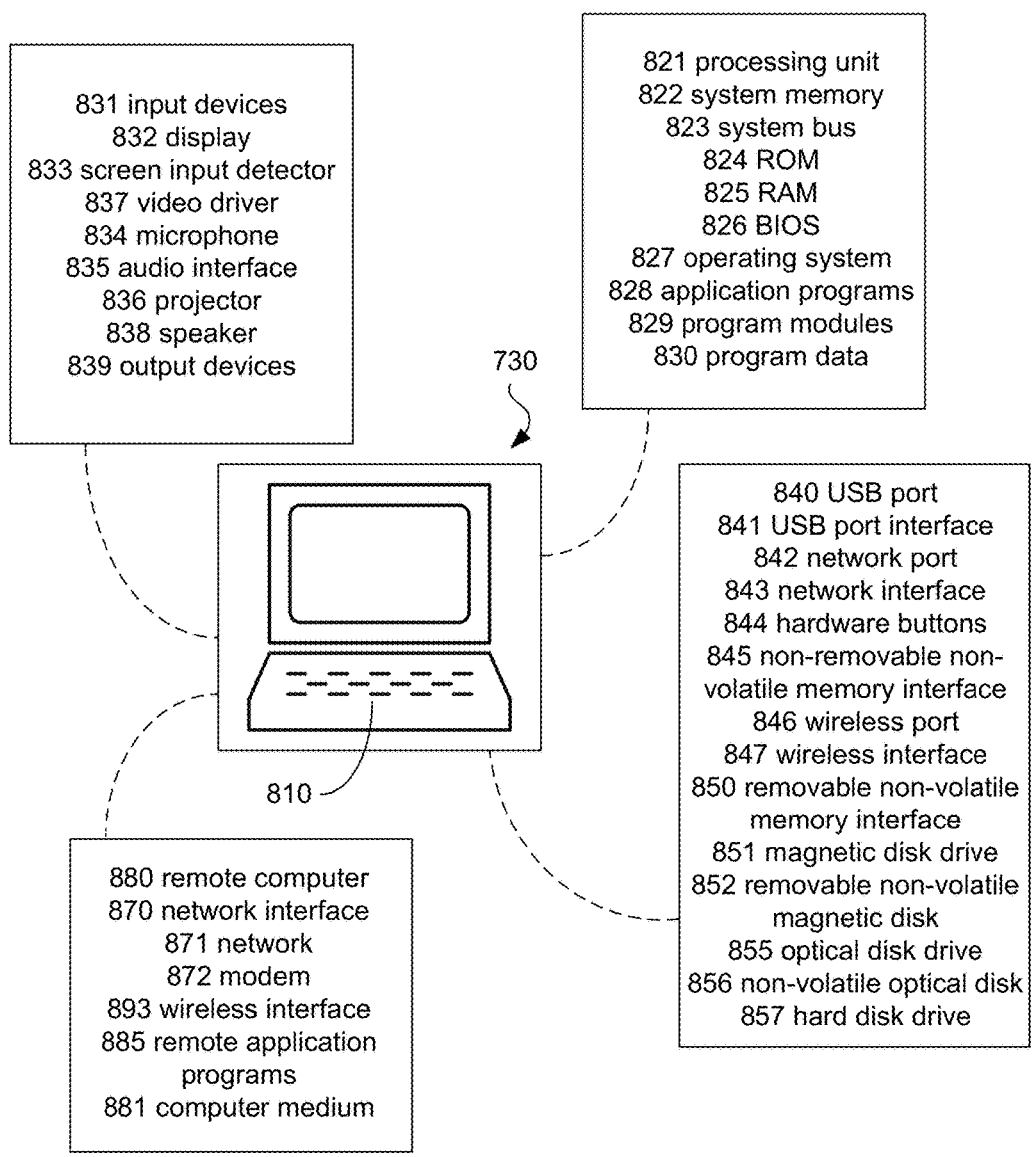
FIG. 8 illustrates aspects of a computing device.

FIG. 8 illustrates further embodiments of computing device 730 for use in a system for assessing the microbiota of skin. Computing device 730 includes a processing unit 821, a system memory 822, and a system bus 823 that couples various system components including the system memory 822 to the processing unit 821. Processing unit 821 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the computing device includes one or more ASICs having a plurality of pre-defined logic components. In an aspect, the computing device includes one or more FPGA having a plurality of programmable logic commands.

The system bus 823 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

Computing device 730 includes a user interface, e.g., one or more input devices 831 and/or output devices 839 for use by a user to interface with the computing device. The one or more input devices 831 can be used to enter information into the computing device and may be integrated into the computing device or may be one or more peripheral devices operably connected through a wired or wireless connection to the computing device. Non-limiting examples of input devices 831 include a graphical user interface, a display, a keyboard, a keypad, a trackball, a joystick, a touch-screen, a mouse, a microphone, an image scanner, a digital camera, a webcam, a light pen, a bar code reader, a fingerprint scanner, a retinal scanner, a game pad, a stylus pen a switch, a dial, or the like. In an aspect, the input device 831 is part of a kiosk structure.

The user interface may include a character, a key-based, or another user data input via a keyboard or touch sensitive display. The user interface may include using a stylus (not shown). Moreover, the user interface is not limited to an actual touch-sensitive panel arranged for directly receiving input, but may alternatively or in addition respond to another input device such as a microphone. A user may enter commands and information into the computing device 730 through user input devices, such as a number of switches and buttons, illustrated as hardware buttons 844, connected to the system via a suitable interface 845. Input devices 831 may further include a touch-sensitive display with suitable input detection circuitry, illustrated as a display 832 and screen input detector 833. The output circuitry of the touch-sensitive display 832 is connected to the system bus 823 via a video driver 837. Other input devices may include a microphone 834 connected through a suitable audio interface 835, and a physical hardware keyboard 810. Output devices may include at least one of the display 832, or a projector display 836. Input device 831 may further include a microphone, keyboard, or pointing device, commonly referred to as a mouse, trackball, or touch pad. Other input devices may include at least one of a touch sensitive display, joystick, game pad, satellite dish, and scanner.

The user interface includes one or more output devices 839 over which processed information is viewed as output results and may be integrated into the computing device or may be one or more peripheral devices operably connected through a wired or wireless connection to the computing device. Non-limiting examples of output devices 839 include but are not limited to television screens, computer monitors, liquid crystal displays, audio speakers, audio headphones, and printers. In an aspect, the computing device 730 may include at least one speaker 838 connected through a suitable audio interface 835. The one or more output devices 839 can be used to report to a user an identification and/or a spatial distribution of at least one type of microbe on a skin surface of an individual. In an aspect, the input/output devices include image-capture device 310 connected through a wired or wireless connection to the computing device.

In an aspect, the one or more input/output devices are connected to the processing unit of the computing device through one or more user input interfaces that are coupled to the system bus, but may be connected by other interfaces and bus structures, such as a parallel port, game port, or a universal serial bus (USB). For example, input devices 831 or output devices 839, may be connected to the processing unit 821 through a USB port 840 and USB port interface 841, to the system bus 823. Alternatively, the other external input devices 831 and output devices 839 may be connected by other interfaces, such as a parallel port, game port or other port. The computing device 730 may further include or be capable of connecting to a flash card memory (not shown) through an appropriate connection port (not shown). The computing device 730 may further include or be capable of connecting with a network through a network port 842 and network interface 843, and through wireless port 846 and corresponding wireless interface 847 may be provided to facilitate communication with other peripheral devices, for example, the scanning device. It will be appreciated that the various components and connections shown are examples and other components and means of establishing communication links may be used.

In an aspect, image-based applications such as viewers and/or toolkits (e.g., Insight Segmentation and Registration Toolkit (ITK)), are incorporated for further intake of information. In an aspect, CAD implementations, image segmentation, or other image analysis algorithms may allow processing of images received from an image capture device.

The system memory includes read-only memory (ROM) 824 and random access memory (RAM) 825. A basic input/output system (BIOS) 826, containing the basic routines that help to transfer information between sub-components within computing device 730, such as during start-up, is stored in the ROM 824. A number of program modules may be stored in the ROM 824 or RAM 825, including an operating system 827, one or more application programs 828, other program modules 829 and program data 830.

Computing device 730 includes computer-readable media products and may include any media that can be accessed by the computing device 730 including both volatile and non-volatile media, removable and non-removable media. By way of example, and not of limitation, computer-readable media may include non-transitory signal-bearing media. By way of example, and not of limitation, computer-readable media may include computer storage media. By way of further example, and not of limitation, computer-readable media may include a communication media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

Computing device 730 may also include other removable/non-removable, volatile/nonvolatile computer storage media products implemented in any method or technology for storage of information such as computer-readable instructions, data structures, program modules, or other data. For example, such media includes a non-removable non-volatile memory interface (hard disk interface) 845 reads from and writes for example to non-removable, non-volatile magnetic media, or a removable non-volatile memory interface 850 that, for example, is coupled to a magnetic disk drive 851 that reads from and writes to a removable, non-volatile magnetic disk 852, or is coupled to an optical disk drive 855 that reads from and writes to a removable, non-volatile optical disk 856, such as a CD ROM. Other removable/ nonremovable, volatile/non-volatile computer storage media that can be used in the example operating environment include, but are not limited to, magnetic tape cassettes, magnetic tape, magnetic disk storage, optical disk storage, memory cards, flash memory cards, DVDs, electrically erasable programmable read-only memory (EEPROM), digital video tape, solid state RAM, and solid state ROM or any other medium which can be used to store the desired information and which can be accessed by the computing device 730. The hard disk drive 257 is typically connected to the system bus 823 through a non-removable memory interface, such as the interface 845, and magnetic disk drive 851 and optical disk drive 855 are typically connected to the system bus 823 by a removable non-volatile memory interface, such as interface 850. In an aspect, computing device 730 includes a computer-readable media drive or memory slot configured to accept non-transitory signal-bearing medium (e.g., computer-readable memory media, computer-readable recording media, or the like). In an aspect, a computer storage media may include a group of computer storage media devices. In an aspect, a computer storage media may include an information store. In an aspect, an information store may include a quantum memory, a photonic quantum memory, or atomic quantum memory. Combinations of any of the above may also be included within the scope of computer-readable media.

In an aspect, a program or set of instructions for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, cloud, or the like.

The drives and their associated computer storage media discussed above provide storage of computer-readable instructions, data structures, program modules, and other data for the computing device 730.

The computing device may operate in a networked environment using logical connections to one or more remote computers, such as a remote computer 880. The remote computer 880 may be a personal computer, a server, a router, a network PC, a peer device, or other common network node, and typically includes many or all of the elements described above relative to the computing device 730. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing device is connected to the network 871 through a network interface, such as the network interface 870, the modem 872, or the wireless interface 893. The network may include a LAN network environment, or a WAN network environment, such as the Internet. In a networked environment, program modules depicted relative to the computing device 730, or portions thereof, may be stored in a remote memory storage device. By way of example, and not limitation, remote application programs 885 as residing on computer medium 881. It will be appreciated that the network connections shown are examples and other means of establishing communication link between the computers may be used.

In some embodiments, the computing device includes one or more modules optionally operable for communication with one or more input/output components that are configured to relay user output/input. In an aspect, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electromechanical systems (MEMS) elements, or other actuators.

In certain instances, one or more elements of the computing device 730 may be deemed not necessary and omitted. In other instances, one or more other components may be deemed necessary and added to computing device 730.

Figure 9:
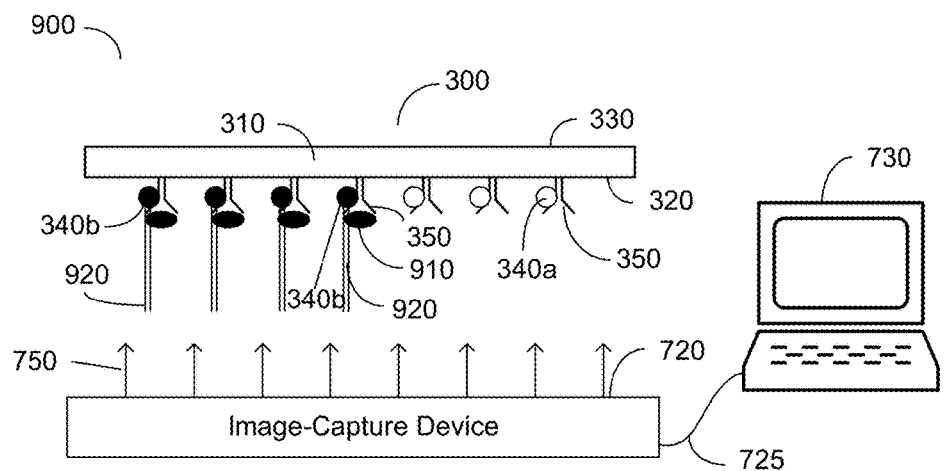
FIG. 9 is a schematic of a system including a skin-covering material for assessing microbiota of skin.

FIG. 9 illustrates aspects of a system for assessing microbiota of skin including a pre-formed skin-covering material that includes a plurality of signal-generating complexes. System 900 includes device 300 of pre-formed skin-covering material 310, image-capture device 720, and computing device 730. Pre-formed skin-covering material 310 includes inner surface 320 and outer surface 330, inner surface 320 substantially conforming in shape to a topography of a skin surface of an individual. Inner surface 320 further includes attached thereto a plurality of signal-generating complexes, each of the plurality of signal generating complexes including specific microbe-binding element 350 operably coupled to either signal-generating element in a first state 340$a$ or signal-generating element in a second state 340$b$. Signal-generating element in a first state 340$a$ is capable of converting to signal-generating element in a second state 340$b$ in response to at least one microbe. In an aspect, conversion from the first state to the second state results in a change in signaling capability, e.g., no signal in response to directed energy to a detectable signal in response to directed energy. In an aspect, conversion from the first state to the second state results in a detectable color change, e.g., from colorless to blue. Signal-generating element in a second state 340$b$ is operably coupled to specific microbe-binding element 350 to which microbe 910 is bound. Signal-generating element in a second state 340$b$ emits one or more signals 920 in response to directed energy 750 from image-capture device 720 while signal-generating element in a first state 340$a$ does not emit one or more signals 920 in response to directed energy 750. Image-capture device 720 includes circuitry to transform one or more signals 920 into a digital output including at least one property and spatial distribution of one or more signals 920. Computing device 730 is operably coupled to image-capture device 720 through communication link 725 and includes circuitry to receive the digital output from image-capture device 720. Computing device 730 further includes circuitry configured to compare the properties of one or more signals 920 with a database of emitted signals of reference signal-generating complexes and generate a digital spatial profile of microbe 910 on the inner surface of pre-formed skin-covering material 310 based on the spatial distribution of one or more signals 760.

Figure 10:
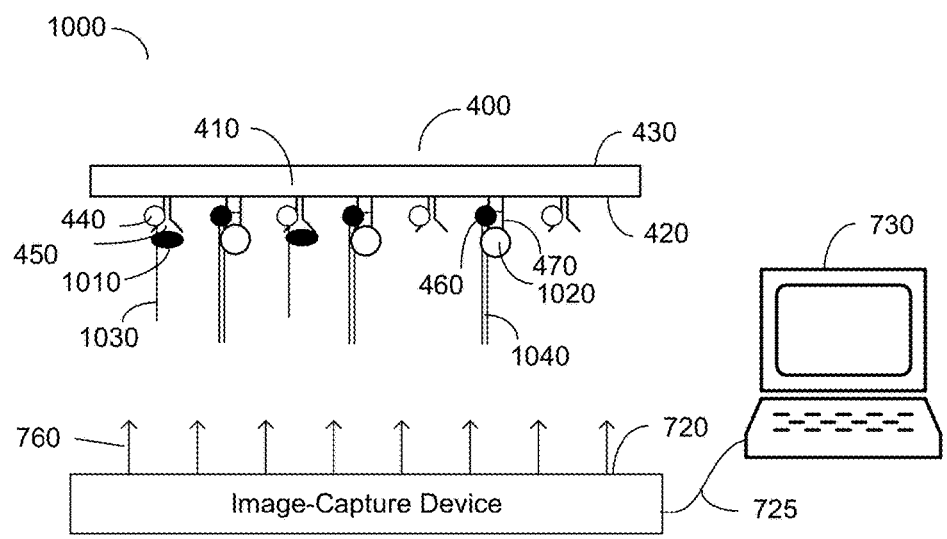
FIG. 10 is a schematic of a system including a skin-covering material for assessing microbiota of skin.

FIG. 10 illustrates aspects of a system for assessing microbiota of skin including a pre-formed skin-covering material that includes a plurality of signal-generating complexes of a first type and a plurality of signal-generating complexes of a second type. System 1000 includes device 400 of pre-formed skin-covering material 410, image-capture device 720, and computing device 730. Pre-formed skin-covering material 410 includes inner surface 420 and outer surface 430, inner surface 420 substantially conforming in shape to a topography of a skin surface of an individual. Inner surface 420 further includes attached thereto a plurality of signal-generating complexes of a first type, each of the plurality of signal generating complexes of the first type including signal-generating element 440 operably coupled to specific microbe-binding element 450 and a plurality of signal-generating complexes of a second type including signal-generating element 460 operably coupled to specific microbe-binding element 470. Signal-generating element 440 emits one or more signals 1030 in response to directed energy 760 from image-capture device 720 when microbe 1010 is associated with operably coupled specific microbe-binding element 450. Signal-generating element 460 emits one or more signals 1040 in response to directed energy 760 from image-capture device 720 when microbe 1020 is associated with operably coupled specific microbe-binding element 470. Image-capture device 720 includes circuitry to transform one or more signals 1030 into a digital output including at least one property and spatial distribution of one or more signals 1030 and to transform one or more signals 1040 into a digital output including at least one property and spatial distribution of one or more signals 1040. Computing device 730 is operably coupled to image-capture device 720 through communication link 725 and includes circuitry to receive the digital output from image-capture device 720. Computing device 730 further includes circuitry configured to compare the properties of one or more signals 1030 and one or more signals 1040 with a database of emitted signals of reference signal-generating complexes and generate a digital spatial profile of microbe 1010 and 1020 on the inner surface of pre-formed skin-covering material 310 based on the spatial distribution of one or more signals 1030 and one or more signals 1040, respectively. In an aspect, two or more types of microbes can be distinguished using signal-generating complexes of two or more types that emit two or more signal types in response to the two or more types of microbes.

Figure 11:
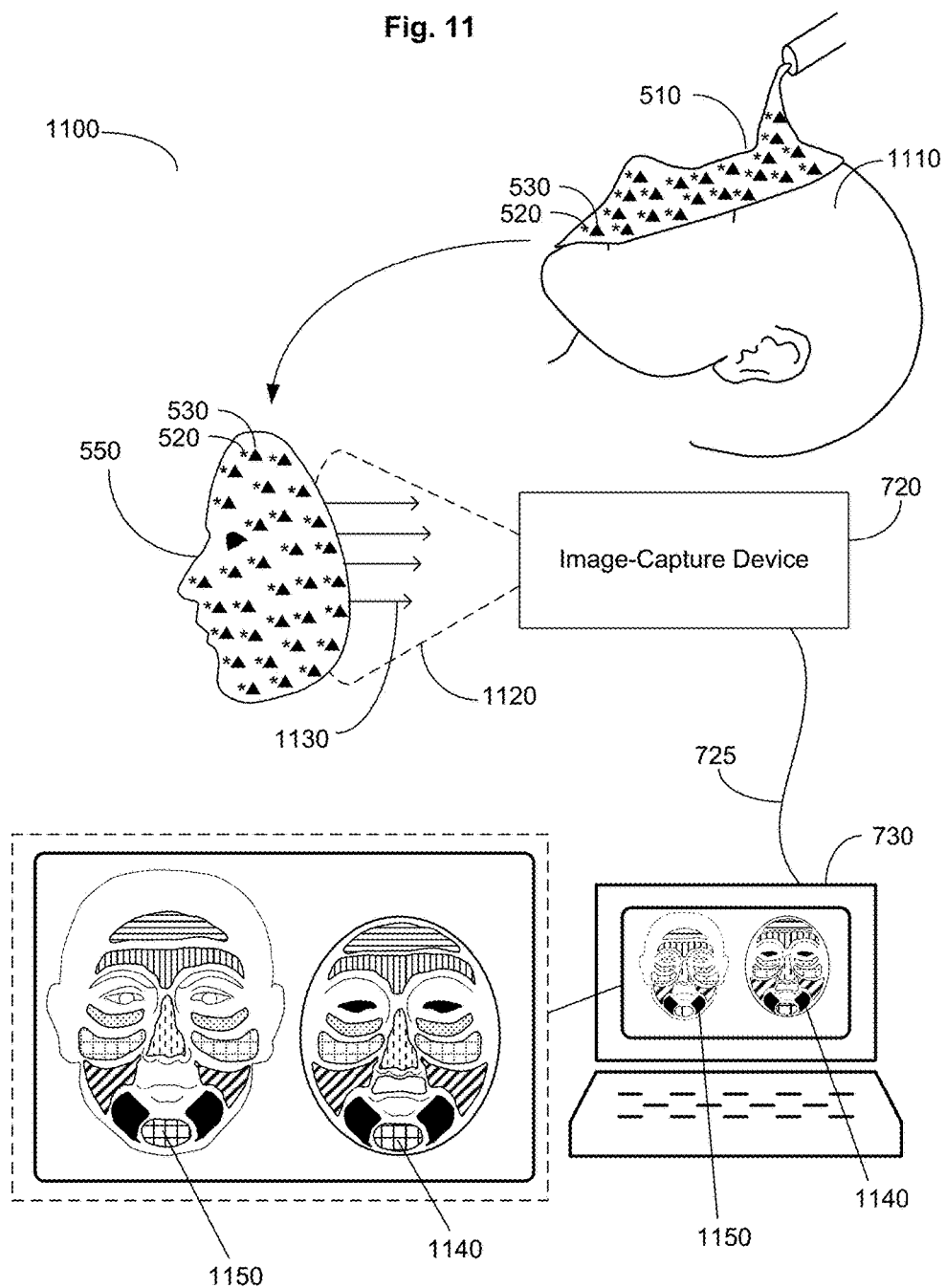
FIG. 11 is a schematic of a system including a peelable skin-covering material for assessing microbiota of skin.

FIG. 11 illustrates aspects of a system including a peelable skin-covering material including a plurality of signal-generating complexes for assessing the microbiota of skin. System 1100 includes peelable skin-covering material 550, image-capture device 720, and computing device 730. Peelable skin-covering material 550 including a plurality of signal-generating complexes, each of the plurality of signal-generating complexes including at least one signal-generating element 520 operably coupled to at least one specific microbe-binding element 530 is formed from settable material 510 and substantially conforms in shape to a topography of a skin surface of individual 1110. Settable material 510 includes at least one material configured to undergo a phase change from a liquid or gelled phase to a flexible solid phase in response to an applied stimulus and includes the plurality of signal-generating complexes including at least one signal-generating element 520 operably coupled to at least one specific microbe-binding element 530.

Image-capture device 720 of system 1100 includes circuitry to capture at least one image of the inner surface of peelable skin-covering material 550 to image one or more signals 1130 emitted from one or more of the plurality of signal-generating complexes. In an aspect, one or more signals 1130 are emitted in response to directed energy 1120. Image-capture device 720 further includes circuitry to transform the captured at least one image into a digital output including information associated with at least one property and a spatial distribution of imaged one or more signals 1130.

Computing device 730 of system 1100 includes a processor and is operably coupled to image-capture device 720 through communications link 725. Computing device 730 includes circuitry configured to receive digital output from image-capture device 720 including the information associated with the at least one property and the spatial distribution of the one or more signals 1130 emitted from the one or more of the plurality of signal-generating complexes on the inner surface of peelable skin-covering material 550, compare the properties of the one or more signals 1130 emitted from the one or more of the plurality of signal-generating complexes with a database of emitted signals of reference signal-generating complexes, and generate digital spatial profile 1140 of the at least one type of microbe based on the spatial distribution of one or more signals 1130 emitted from the one or more of the plurality of signal-generating complexes. In an aspect, computing device 730 further includes circuitry to generate a digital alignment 1150 of digital spatial profile 1140 of the at least one type of microbe with a digital image of a skin surface of individual 1110 covered by settable material 510 prior to peeling. Digital alignment 1150 can be reported to a user of the system, e.g., individual 1110 or another individual, to aid in determining a recommended treatment regimen to maintain or alter the current types and spatial distribution of microbes on the skin surface of the individual.

Figure 12A:
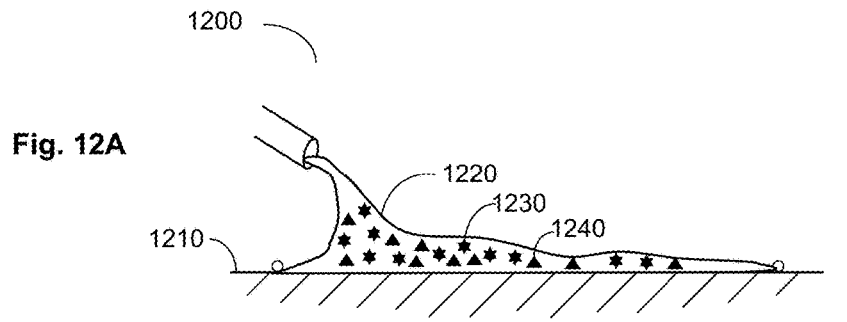
FIG. 12A illustrates application of a peelable skin-covering material to a skin surface.
Figure 12B:
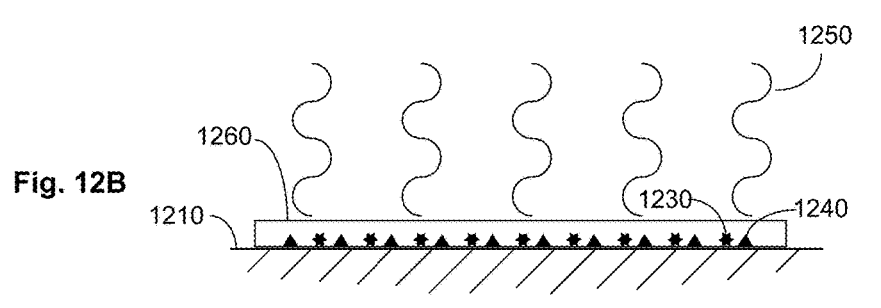
FIG. 12B shows a cross-section through a peelable skin-covering material on a skin surface
Figure 12C:
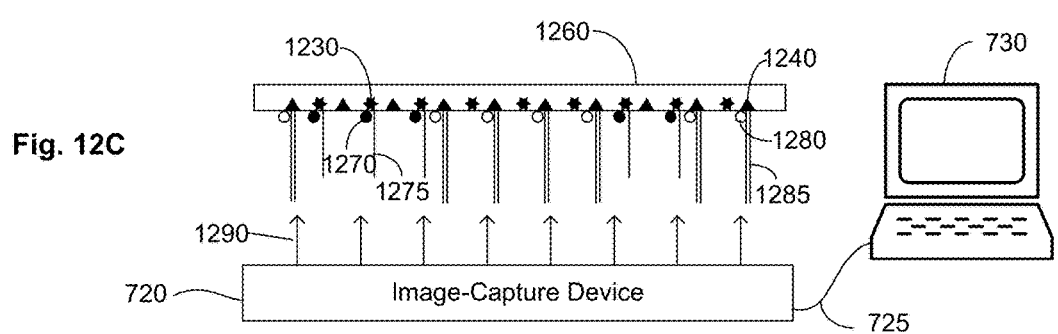
FIG. 12C illustrates analysis of a peelable skin-covering material with an image-capture device.

FIGS. 12A, 12B, and 12C illustrate aspects of a system including a peelable skin-covering material and a plurality of signal-generating complexes of a first type and a plurality of signal-generating complexes of a second type. System 1200 includes settable material 1220, peelable skin-covering material 1260, image-capture device 720, and computing device 730. FIG. 12A shows a cross-section through settable material 1220 applied to skin surface 1210. Settable material 1220 includes at least one material configured to undergo a phase change form a liquid or gelled phase to a flexible solid phase in response to an applied stimulus. Settable material 1220 includes at least one of latex, gel, polymer, plastic, or resin. Settable material 1220 includes a plurality of signal-generating complexes of a first type 1230 and a plurality of signal-generating complexes of a second type 1240. In an aspect, one or more of the plurality of signal-generating complexes of a first type 1230 includes at least one signal-generating element of a first type operably coupled to at least one specific microbe-binding element of a first type, the at least one signal-generating element of the first type configured to emit one or more signals of a first type in response to at least one first type of microbe bound to the operably coupled at least one specific microbe-binding element of the first type. In an aspect, one or more of the plurality of signal-generating complexes of a second type 1240 includes at least one signal-generating element of a second type operably coupled to at least one specific microbe-binding element of a second type, the at least one signal-generating element of the second type configured to emit one or more signals of a second type in response to at least one second type of microbe bound to the operably coupled at least one specific microbe-binding element of the second type.

FIG. 12B illustrates a cross-section through peelable skin-covering material 1260 formed from application of stimulus 1250 to settable material 1220. Stimulus 1250 can include at least one of air, a thermal stimulus, or an electromagnetic stimulus. Peelable skin-covering material 1260 includes the plurality of signal-generating complexes of a first type 1230 and the plurality of signal-generating complexes of a second type 1240. FIG. 12C illustrates a cross-section of peelable skin-covering material 1260 in contact with image-capture device 720. At least one of the plurality of signal-generating complexes of a first type 1230 emits one or more signals 1275 in response to microbe 1270 and at least one of the plurality of signal-generating complexes of a second type 1240 emits one or more signals 1285 in response to microbe 1280. In an aspect, one or more signals 1275 and/or one or more signals 1285 are emitted and/or reflected in response to directed energy 1290 generated from an energy-generating mechanism of image-capture device 720. Image-capture device includes circuitry to transform one or more signals 1275 and one or more signals 1285 into a digital output including properties and spatial distributions of one or more signals 1275 and one or more signals 1285. Computing device 730 is operably coupled to image-capture device 720 through communication link 725 and includes circuitry to generate a digital spatial profile of microbe 1270 and of microbe 1280 based on the spatial distribution of one or more signals 1275 and one or more signals 1285, respectively, as described above herein.

FIG. 13 shows a flowchart of a method for assessing microbiota of the skin. The method includes receiving a digital output from an image-capture device, the digital output including information associated with at least one property and at spatial distribution of one or more signals emitted from one or more of a plurality of signal-generating complexes associated with an inner surface of a skin-covering material, the one or more signals emitted from the one or more of the plurality of signal-generating complexes in response to at least one type of microbe in block 1300; identifying the at least one type of microbe by comparing the information associated with the at least one property of the one or more signals emitted from the one or more of the plurality of signal-generating complexes with a database of signal properties of reference signal-generating complexes in block 1310; generating a digital spatial profile of the at least one type of microbe based on the spatial distribution of the one or more signals emitted from the one or more of the plurality of signal-generating complexes in response to the at least one type of microbe in block 1320; and reporting to a user an identification and the digital spatial profile of the identified at least one type of microbe in block 1330.

In an aspect, the method of FIG. 13 is implemented on a computing device. In an aspect, the method of FIG. 13 is implemented on computing device such as that described in FIG. 8. The computing device can take various forms or be part of an object, and can include, but not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, or any other like device that takes information as an input and gives it back to the end-users. The computing device can include a digital single processor, ASIC, microprocessor, or other type of processor operating on a system such as a personal computer, server, a router, of other device capable of processing data including network interconnection device. In an aspect, the computing device is part of a kiosk.

FIG. 14 shows further aspects of a method such as shown in FIG. 13. In an aspect, receiving a digital output from an image-capture device can include receiving the digital output from at least one digital camera as illustrated in block 1400. Non-limiting examples of digital cameras have been described above herein. In an aspect, receiving a digital output from an image-capture device can include receiving the digital output from at least one scanning device as shown in block 1410. In an aspect, receiving the digital output from at least one scanning device includes receiving the digital output from at least one active scanning device. For example, the scanning device can include an energy-generating mechanism that generates directed energy, e.g., a laser, which is used to elicit a response from one or more of the plurality of signal-generating complexes on the inner surface of the skin covering material. In an aspect, receiving the digital output from at least one scanning device includes receiving the digital output from at least one passive scanning device. For example, the scanning device can passively receive one or more signals, e.g., an optical signal, radioactive, or magnetic signals, from one or more of the plurality of signal-generating complexes. In an aspect receiving the digital output from at least one scanning device include receiving the digital output from a three-dimensional scanning device. In an aspect, receiving the digital output from at least one scanning device includes receiving the digital output from at least one of an optical scanning device, a fluorescence scanning device, an acoustic scanning device, or an electromagnetic scanning device.

The method includes identifying the at least one type of microbe by comparing the information associated with the at least one property of the one or more signals emitted from the one or more of the plurality of signal-generating complexes with a database of signal properties associated with one or more reference signal-generating complexes. In an aspect, comparing the information associated with the at least one property includes comparing at least one of an optical property as shown in block 1420. For example, the method can include comparing a change in color with a reference color, e.g., colorless to violet, in response to the at least one type of microbe. In an aspect, comparing the information associated with the at least one property includes comparing at least one of a fluorescence property as shown in block 1425. For example, the method can include comparing a fluorescent signal, e.g., green fluorescence associated with fluorescein or Cy3, or a change in fluorescence, e.g., an intensity, in response at least one type of microbe with a reference fluorescence or change in fluorescence. In an aspect, comparing the information associated with the at least one property includes comparing at least one of an infrared spectral property as shown in block 1430. In an aspect, comparing the information associated with the at least one property includes comparing at least one of an acoustic property as shown in block 1435. In an aspect, comparing the information associated with the at least one property includes comparing at least one of a magnetic property as shown in block 1440. In an aspect, comparing the information associated with the at least one property includes comparing at least one of an electromagnetic property as shown in block 1445. In an aspect, comparing the information associated with the at least one property includes comparing at least one of an electrical property as shown in block 1450. In an aspect, comparing the information associated with the at least one property includes comparing at least one of a wavelength as shown in block 1455. In an aspect, comparing the information associated with the at least one property includes comparing at least one of a frequency as shown in block 1460. In an aspect, comparing the information associated with the at least one property includes comparing at least one of an amplitude as shown in block 1465.

In an aspect, the method includes generating a recommended treatment regimen based on the identification and the digital spatial profile of the identified at least one type of microbe; and reporting the recommended treatment regimen to the user, as shown in block 1470 of FIG. 14. For example, the method can include generating a recommended treatment regimen that includes an antimicrobial treatment based on the types of microbes present, e.g., antibiotics for bacteria, fungicide for fungus, or antiviral for a virus. For example, the method can include generating a recommended treatment regimen that includes a skin cleaning process, e.g., a type of soap or antiseptic rinse, based on the identity and the distribution of the at least one type of microbe. For example, the method can include generating a recommended treatment regimen that includes a certain type of cosmetic product that is compatible with the microbes present, e.g., helps to maintain good microbes but not encourage bad microbes and can include probiotics. Non-limiting examples of treatment recommendations include antimicrobial agents, cleansing products, cosmetic products, procedures (e.g., shaving or not in sensitive areas, applying warm compresses to open pores, use of a pore-opening or cleaning device, abrasion, and the like). In an aspect, the method can include alerting the individual as to whether the identity and the spatial distribution of the at least one type of microbe warrants discussion with a medical professional. In an aspect, reporting the recommended treatment regimen to the user includes reporting the recommended treatment regimen via a display, a printout, or exportation of data to another device, e.g., a personal handheld device, or to another individual, e.g., a service provider or interested third party.

FIG. 15 shows further aspects of a method such as shown in FIG. 13. In an aspect, the method includes generating at digital alignment of the digital spatial profile of the identified at least one type of microbe with a digital image of a skin surface of an individual covered by the inner surface of the skin-covering material; generating a personalized microbe profile for the individual from the generated digital alignment, the personalized microbe profile including the identification and a spatial profile of the identified at least one type of microbe on the skin surface of the individual; and reporting to the user the personalized microbe profile, as illustrated in block 1500. In an aspect, reporting to a user includes reporting to the individual, i.e., the individual for whom the personalized microbe profile was generated. In an aspect, reporting to the user includes reporting to a service provider, e.g., a medical practitioner, a cosmetologist, or other service provider, who prepares the personalized microbe profile for the individual. In an aspect, reporting to the user includes reporting to a third party, e.g., an insurance company or the manufacturer of the skin-covering material and/or components of the system including the skin-covering material.

In an aspect, the method includes using one or more image registration algorithms to generate the digital alignment between the digital spatial profile and the digital image of the skin surface of an individual. In an aspect, the method includes aligning one or more registration marks, e.g., colored or fluorescent spots with one or more corresponding landmarks from the skin surface captured by the digital image. For example, the method can include aligning one or more registration marks on the digital spatial profile with one or more corresponding moles on the skin surface of the individual. For example, the method can include aligning one or more registration marks on the digital spatial profile with one or more corresponding marks placed on the skin surface of the individual with a pen.

In an aspect, the method includes detecting one or more features depicted in the digital images, e.g., the physical landmarks, and match these features with features in the digital spatial profile, e.g., the registration landmarks. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. The method further includes matching the features detected in the one or more digital images of the skin surface with features in the digital spatial profile using one or more feature-matching methods, non-limiting examples of which include Euclidean distance matching, invariant moments, nearest neighbor based matching, correlation-like methods, Fourier methods, mutual information methods, optimization methods.

In an aspect, the method includes providing a visual representation of the personalized microbe profile on a display, as illustrated in block 1510. The display can include a display coupled to a computing device, wherein the computing device can take various forms or be part of an object, and can include, but not limited to, a computer, a laptop computer, a personal electronic device, a dedicated computing device, a limited resource computing device, a wireless communication device, a mobile wireless communication device, an electronic pen, a handheld electronic writing device, a tablet, a digital camera, a scanner, an ultrasound device, an x-ray machine, a non-invasive imaging device, a cell phone, a PDA, an electronic tablet device, a medical apparatus, or any other like device that takes information as an input and gives it back to the end-users. In an aspect, the display is part of a kiosk that includes the image-capture device and the computing device.

In an aspect, the method includes providing a printout of the personalized microbe profile, as illustrated in block 1520. For example, the printout of the personalized microbe profile can include a text only description of the identity and spatial profile of the identified at least one type of microbe on the skin surface of the individual. For example, the printout of the personalized microbe profile can include a color-coded diagram illustrating the identity and the spatial profile of the identified at least one type of microbe on the skin surface of the individual. The color-coded information can be overlaid on an image of the skin surface of the individual. For example, the color-coded diagram can be overlaid over an image of the individual's face, illustrating the distribution of one or more types of microbes on the individual's face.

In an aspect, the method includes exporting the personalized microbe profile to a computing device, as illustrated in block 1530. For example, the personalized microbe profile may be generated on a first computing device, e.g., a service provider's office, operably coupled to the image-capture device, e.g., in a service provider's office, and subsequently exported to a second computing device, e.g., an individual's home computer, a hand-held device, personal electronic device, or the like. For example, the personalized microbe profile may be generated on a first computer in the individual's residence and subsequently exported to a second computer associated with a service provider, e.g., a medical practitioner's office, a pharmacy, or cosmetic counter. In an aspect, the service provider may provide a recommended treatment regimen in response to receipt of an individual's personalized microbe profile.

In an aspect, the method can include generating a recommended treatment regimen based on the personalized microbe profile, and reporting the recommended treatment regimen to the user as shown in block 1540. For example, the method may include recommending a specific antibiotic and/or antifungal regimen based on the personalized microbe profile. For example, the method may include recommending a skin-cleansing regimen based on the personalized microbe profile. For example, the method may include recommending a probiotic regimen based on the personalized microbe profile. Non-limiting components of a recommended treatment regimen have been described above herein.

In an aspect, the method includes comparing the personalized microbe profile with a reference microbe profile, generating a recommended treatment regimen for the individual based on the comparison, and reporting the recommended treatment regimen to the user, as shown in block 1550. In an aspect, the method can include comparing with a reference microbe profile generated for the individual at a previous point in time, as shown in block 1560. The previous point in time can include days, months, and/or years prior to a current time point. For example, the method can include comparing the microbe profile with a reference microbe profile generated when the individual was younger, allowing for analysis of the microbe profile as a function of age. For example, the method can include comparing the microbe profile with a reference microbe profile generated for an individual prior to the onset of a medical condition, e.g., acne, psoriasis, or eczema. For example, the method can include comparing the microbe profile with a reference microbe profile generated for an individual prior to treatment for a skin condition, allowing for analysis of the microbe profile before and after a treatment regimen.

In an aspect, the method can include comparing with a reference microbe profile generated for one or more other individuals, as shown in block 1570. For example, the method can include comparing the microbe profile with a reference microbe profile that represents an optimal microbe profile generated by averaging microbe profile information gathered from a number of other individuals. For example, the method can include comparing the microbe profile with a reference microbe profile that represents an optimal microbe profile generated from one or more other individuals with a complexion preferred by the individual. For example, the method can include comparing the microbe profile with reference microbe profile that represents a microbe profile from a celebrity with a complexion or skin properties preferred by the individual.

FIG. 16 illustrates aspects of a method for assessing microbiota of skin. The method includes generating a recommended treatment regimen based on comparing microbiota of a skin surface of an individual at two or more points in time. The method includes receiving a first digital output from an image-capture device at block 1600, the first digital output including information associated with at least one property and a spatial distribution of a first set of one or more signals emitted at a first time point from at least one of a plurality of signal-generating complexes associated with an inner surface of a first skin-covering material; receiving a second digital output from an image capture device at block 1610, the second digital output including information associated with at least one property and a spatial distribution of a second set of one or more signals emitted at a second time point from at least one of a plurality of signal-generating complexes associated with an inner surface of a second skin-covering material; comparing the first digital output with the second digital output at block 1620; generating a recommended treatment regimen based on the comparison of the first digital output with the second digital output at block 1630; and reporting the recommended treatment regimen to a user at block 1640.

In an aspect, the method includes using a first skin-covering material that is distinct from the second skin-covering material. For example, a first skin-covering material can be manufactured for use at the first time point and a second skin-covering material manufactured for use at the second time point. For example, the first skin-covering material can include a settable material to generate a first peelable skin-covering material at the first time point while the second skin-covering material uses same or different settable material to generate the second peelable skin-covering material at the second time point.

In an aspect, the method includes using a reusable skin-covering material wherein the plurality of signal-generating complexes on the inner surface of the skin-covering material are refreshed, renewed, or rejuvenated. For example, a pre-formed skin covering material can include a removable layer of signal-generating complexes that once used are removed, e.g., by washing, and a new layer of signal-generating complexes applied to the inner surface. For example, a pre-formed skin covering material can include a renewable layer of signal-generating complexes, wherein a change in pH, heat, or other stimulus is used to remove any bound microbes or parts thereof and to convert the signal-generating complexes back to a state amenable to interacting with at least one type of microbe and generating a signal accordingly in subsequent uses of the pre-formed skin-covering material. In this manner, a single, pre-formed skin-covering material can be generated for an individual and used repeatedly with new or refreshed signal-generating complexes.

In an aspect, the first time point is at a first age of an individual and the second time point is at a second age of an individual. For example, the first time point and the second time point may be separated by days, months, or years depending upon how frequently the skin microbiota of an individual is assessed or monitored. In an aspect, the first time point is at a time before therapeutic treatment and the second time point is at a time after therapeutic treatment. In an aspect, the first time point is at a time point before the onset of a pathological condition, e.g., a normal baseline, and the second time point is at a time point after the onset of the pathological condition. In an aspect, comparing the microbiota at a first time point versus a second time point is used to generate a recommended treatment regimen to maintain and/or modulate the type and spatial distribution of microbes on the skin surface of an individual.

FIG. 17 illustrates aspects of a method for identifying and generating a spatial profile of microbiota of skin. The method includes applying a skin-covering material to a skin surface of an individual at block 1700, the skin-covering material including an inner surface and an outer surface, the inner surface substantially conforming in shape to a topography of the skin surface of the individual and including attached thereto a plurality of signal-generating complexes, one or more of the plurality of signal-generating complexes configured to emit one or more signals in response to at least one type of microbe; removing the skin-covering material from the skin surface of the individual in block 1710; capturing at least one image of the inner surface of the skin-covering material with an image-capture device, the at least one image including one or more signals emitted from the one or more of the plurality of signal-generating complexes in response to the at least one type of microbe and transforming the captured at least one image into a digital output including information associated with at least one property and a spatial distribution of the imaged one or more signals in block 1720; receiving the digital output from the image-capture device in block 1730, the digital output including information associated with at least one property and a spatial distribution of the imaged one or more signals emitted from the one or more of the plurality of signal-generating complexes in response to the at least one type of microbe; identifying the at least one type of microbe by comparing the information associated with the at least one property of the imaged one or more signals emitted from the one or more of the plurality of signal-generating complexes with a database of signal properties of reference signal-generating complexes in block 1740; generating a digital spatial profile of the at least one type of microbe based on the spatial distribution of the imaged one or more signals emitted from the one or more of the plurality of signal-generating complexes in block 1750, and reporting to a user an identification and spatial profile of the identified at least one microbe in block 1760.

In an aspect, the method of FIG. 17 includes applying a pre-formed skin-covering material to the skin surface of the individual. In an aspect, the method of FIG. 17 includes applying a settable material to the skin surface of the individual, the settable material configured to undergo a phase change from a liquid or gelled phase to a flexible solid phase to form a peelable skin-covering material in response to an applied stimulus. Non-limiting examples of pre-formed and peelable skin-covering material have been described above herein.

In an aspect, applying the skin-covering material to the skin surface of the individual includes applying the skin-covering material to the skin surface of the individual for a prescribed period of time. In an aspect, the prescribed period of time can be one or more seconds. For example, the prescribed period of time may be the time required to press the skin-covering material onto the skin surface and then immediately removing the skin-covering material. For example, the skin-covering material can be placed in uniform contact with the skin surface and immediately removed, e.g., about 1-10 seconds. In an aspect, the prescribe period of time can be one or more minutes. For example, the prescribed period of time may be the time required to apply skin-covering material to the skin surface of the individual, followed by additional steps required to aid in capturing the one or more microbes from the skin surface. For example, the skin-covering material can be placed in uniform contact with the skin surface and allowed to sit on the skin surface for about 10 seconds to about 60 minutes.

In an aspect, applying the skin-covering material to the skin surface of the individual includes applying the skin-covering material to the skin surface of the individual under pressure. For example, pressure may be applied manually using hands to press the skin-covering material onto the skin surface of the individual. For example, pressure may be applied by using a tool that allows for uniform pressing of the skin-covering material onto the skin surface of the individual.

In an aspect, applying the skin-covering material to the skin surface of the individual includes applying the skin-covering material to the skin surface of the individual in the presence of a vacuum. For example, the skin-covering material may be adhered to the skin, e.g., with an adhesive, and gentle vacuum used to suction microbes from the skin surface and onto the inner surface of the skin-covering material.

In an aspect, applying the skin-covering material to the skin surface of the individual includes applying the skin-covering material to the skin surface of the individual in the presence of a stimulus. In an aspect, the stimulus includes a thermal or chemical stimulus. For example, the skin surface and/or the skin-covering material may be warmed to facilitate access to microbes on the skin surface, e.g., by opening skin pores. For example, the skin surface and/or the skin-covering material may include a detergent or other agent to aid in removing whole microbes or parts thereof, e.g., proteins, DNA, or RNA, from the skin surface.

FIG. 18 illustrates further aspects of a method such as shown in FIG. 17. In an aspect, the method includes applying the plurality of signal-generating complexes to the inner surface of the skin-covering material prior to applying the skin-covering material to the skin surface of the individual, as shown in block 1800. For example the plurality of signal-generating complexes can be formulated into a spray that is applied to the inner surface of a pre-formed skin-covering material prior to applying the skin-covering material to the skin surface of an individual. For example the plurality of signal-generating complexes can be formulated as a liquid or gel that is applied to the inner surface of a pre-formed skin-covering material prior to applying the skin-covering material to the skin surface of an individual. In an aspect, the plurality of signal-generating complexes can be applied directly to the skin surface of the individual prior to applying either a settable material or a pre-formed skin-covering material. For example, the plurality of signal-generating complexes can be modified with streptavidin to allow binding to a biotin coated inner surface of a skin-covering material. In an aspect, the at least one signal-generating element and the at least one specific microbe-binding element of a signal-generating complex can be applied separately to the skin surface and/or the inner surface of the skin-covering material. For example, a signal-generating element can be modified with biotin and added to the skin surface or directly to an inner surface including a specific microbe-binding element modified with avidin.

In an aspect, the method includes separating the skin-covering material into one or more pieces along one or more tearable lines of perforation, and capturing at least one image with the image-capture device of the inner surface of at least one of the one or more pieces of the skin-covering material, as shown in block 1810. In an aspect, the skin-covering material can be manufactured with perforations. For example, the skin-covering material may be manufactured using a three-dimensional printing process in which the digital template for the skin-covering material includes perforations. In an aspect, the perforations are added to the skin-covering material after manufacture. For example, a skin-covering material manufactured from a thin sheet of material, e.g., latex or paper may be modified with a device configured to punch holes through the skin-covering material. In general, the tearable lines of perforation allow the skin-covering material to be separated into pieces that can be accommodated by the imaging window or scanning surface of the image-capture device. In an aspect, the one or more tearable lines are configured to allow a non-planar skin-covering material to be flattened into a planar skin-covering material to facilitate image analysis, without actually tearing the skin-covering material into separate pieces.

Figure 19A:
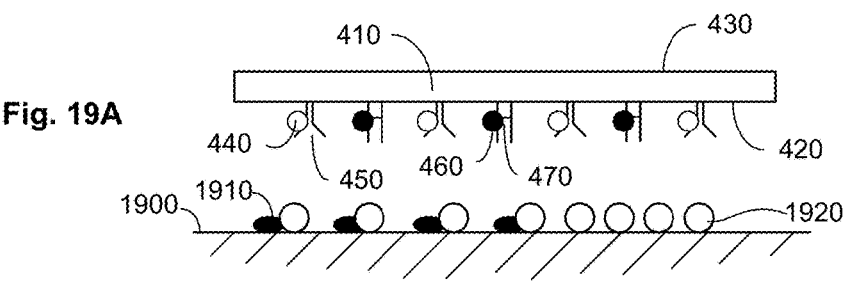
FIG. 19A illustrates further aspects of a method such as shown in FIG. 17.

FIGS. 19A-D illustrate aspects of a method for assessing microbiota of skin. The method is implemented with a system including skin-covering material 410, image-capture device 720, and computing device 730. FIG. 19A illustrates a cross-section through skin-covering material 410 in proximity to skin surface 1900. Skin-covering material 410 includes a pre-formed skin-covering material including inner surface 420 and an outer surface 430, inner surface 420 substantially conforming in shape to a topography of skin surface 1900. Inner surface 420 includes attached thereto a plurality of signal-generating complexes of a first type including signal-generating element of a first type 440 operably coupled to specific microbe-binding element of a first type 450 and a plurality of signal-generating complexes of a second type including signal-generating element of a second type 460 operably coupled to specific microbe-binding element of a second type 470. Skin surface 1900 includes at least one first type of microbe 1910 and at least one second type of microbe 1920.

Figure 19B:
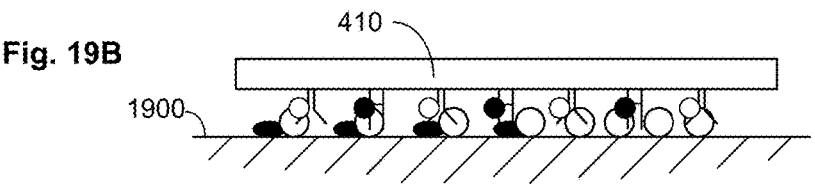
FIG. 19B shows further aspects of a method such as depicted in FIG. 17.

FIG. 19B illustrates applying skin-covering material 410 to skin surface 1900. Specific microbe-binding element of a first type 450 recognizes at least one first type of microbe 1910 while specific microbe-binding element of a second type 470 recognizes at least one second type of microbe 1920.

Figure 19C:
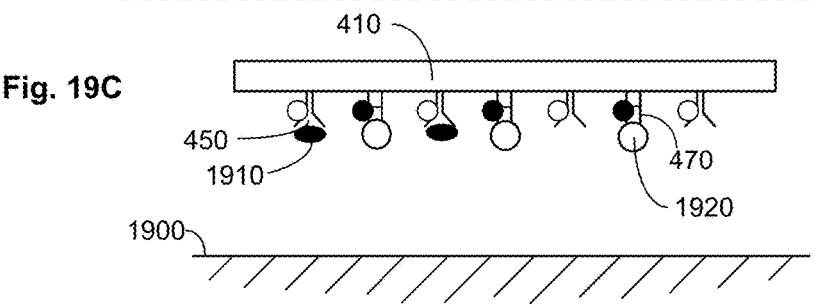
FIG. 19C depicts further aspects of a method such as illustrated in FIG. 17.

FIG. 19C illustrates removing skin-covering material 410 from skin surface 1900. At least one first type of microbe 1910 is bound to specific microbe-binding element of a first type 450 and at least one second type of microbe 1920 is bound to specific microbe-binding element of a second type 470.

Figure 19D:
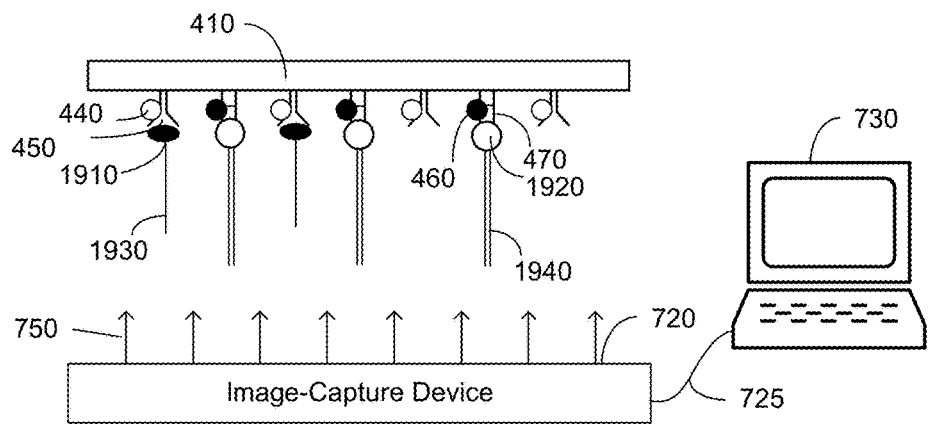
FIG. 19D illustrates further aspects of a method such as shown in FIG. 17.

FIG. 19D illustrates capturing at least one image of inner surface 420 of skin-covering material 410 with image-capture device 720 to image one or more signals emitted from the one or more of the plurality of signal-generating complexes. Signal-generating element of a first type 440 emits one or more signals of a first type 1930 in response to the at least one first type of microbe 1910 bound to operably coupled specific microbe-binding element of a first type 450 and signal-generating element of a second type 460 emits one or more signals of a second type 1940 in response to at the least one second type of microbe 1920 bound to operably coupled specific microbe-binding element of a second type 470. In an aspect, the method further includes exposing inner surface 420 of skin-covering material 410 with directed energy 750 to elicit a signaling response. The method further includes transforming the captured at least one image into a digital output including information associated with at least one property and a spatial distribution of the imaged one or more signals.

The method further includes computing device 730 receiving the digital output from image-capture device 720 through communication link 725; identifying the at least one first type of microbe 1910 and the at least one second type of microbe 1920 by comparing the information associated with the at least one property of the one or more signals of a first type 1930 and the at least one property of the one or more signals of a second type 1940 emitted from the one or more of the plurality of signal-generating complexes with a database of single properties of reference signal-generating complexes; generating a digital spatial profile of the at least one first type of microbe 1910 and the at least one second type of microbe 1920 based on the spatial distribution of the respective one or more signals of a first type 1930 and one or more signals of a second type 1940; and reporting to a user an identification and spatial profile of the identified at least one first type of microbe 1910 and at least one second type of microbe 1920.

FIG. 20 illustrates further aspects of a method such as that shown in FIG. 17. In an aspect, the method includes generating a recommended treatment regimen based on the identification and the digital spatial profile of the at least one type of microbe; and reporting the recommended treatment regimen to the user, as shown in block 2000. In an aspect, the method further includes generating a digital alignment of the digital spatial profile of the at least one type of microbe with a digital image of the skin surface of the individual covered by the inner surface of the skin-covering material, creating a personalized microbe profile from the digital alignment, the personalized microbe profile including the identification and the spatial profile of the identified at least one type of microbe on the skin surface of the individual; generating a recommended treatment regimen based on a comparison of the personalized microbe profile with at least one reference microbe profile; and reporting to the user at least one of the personalized microbe profile or the recommended treatment regimen, as illustrated in block 2010. For example, a digital image of the individual can be captured before, during or after placement of the skin-covering material onto the skin surface. In an aspect, the digital image of the skin-surface of the individual can be used to design a personalized skin-covering material as described above herein. One or more registration marks on the skin-covering material can be used to align with one or more landmarks, e.g., moles, blood vessels, or other landmarks on the skin surface that are visible in the digital image. In an aspect, the one or more registration marks are incorporated into the manufacture of the skin-covering material. In an aspect, the one or more registration marks can be added, e.g., with a pen or other marking device, while the skin-covering material is on the skin-surface of the individual.

In an aspect, an additional signal-generating element may be applied to the inner surface of the skin-covering material to enhance the signal of the signal-generating complex incorporated into the skin-covering material or to generate a confirmatory or secondary signaling event. For example, an additional signal-generating element may include a vital dye that intercalates into nucleic acids of captured microbes, non-limiting examples of which include DAPI (4',6-diamidino-2-phenylindole), acridine orange, or Hoechst stain. Other non-limiting examples of vital dyes include calcein AM, carboxyfluorescein diacetate, DiOC (3,3'-dihexyloxacarbocyanine iodide), rhodamine 123, and Nile red. In an aspect, an additional signal-generating element may include a dye-labeled antibody, aptamer, or binding agent that binds to at least one type of microbe captured by the signal-generating complex. For example, the dye-labeled antibody, aptamer, or other binding agent can bind to one or more biomolecule exposed on the outer surface of a microbe, e.g., a protein, carbohydrate or lipid biomolecule exposed on the outer surface of the microbe. The label associated with the antibody, aptamer, or other binding agent can include a fluorescent label, a colored label, or a chemiluminescent label. For example, the labeled antibody, aptamer, or other binding agent configured to bind the at least one type of microbe may further include fluorescein for direct fluorescence detection or horseradish peroxidase (HRP) for indirect detection using colorimetric or chemiluminesence following addition of peroxidase substrate. In some aspects, the labeled antibody, aptamer, or other binding agent configured to bind the at least one type of microbe may further include biotin conjugates available for binding with avidin or streptavidin. In an aspect, the additional signal-generating element includes at least one fluorescence-generating agent. In an aspect, the additional signal-generating element includes at least one chemiluminescence-generating agent. In an aspect, the additional signal-generating element includes a dye-labeled anti-16S RNA. In an aspect, the additional signal-generating element includes universal primers for amplification of microbial 16S gene sequencing the 1.4 kb amplicon and comparing with known sequences in a database, e.g., Ribosomal Database Project (Cole et al. (2009) Nucl. Acids Res. 37(D1):D141-D145; SILVA (Quast et al. (2013) Nucl. Acids Res. 41(D1):D590-D596; CORE ("core human oral microbiome;" Griffen et al. (2011), PLoS ONE 6(4):e19051, which are incorporated herein by reference). Other non-limiting examples of the additional signal-generating elements include radioactive agents, magnetic agents, radiofrequency identification tags, or contrast agents. In an aspect, the additional signal-generating element can further include labeled oligonucleotides, lectins, proteins, lipids, carbohydrates, ligands, or any other molecule capable carrying a label and interacting with one or more components of the at least one type of microbe captured on the inner surface of the skin-covering material. In an aspect, the additional signal-generating element can include one or more of a specific microbe-binding element, non-limiting examples of which are described below herein. In an aspect, the additional signal-generating element can include any one of the signal-generating elements described above herein.

Figure 21A:
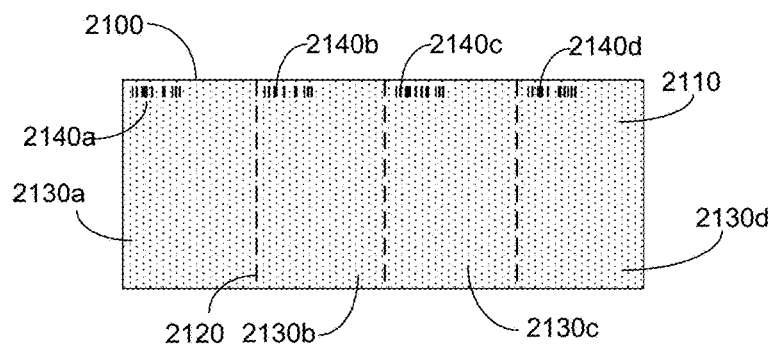
FIG. 21A is a skin-covering material with lines of tearable perforations.
Figure 21B:
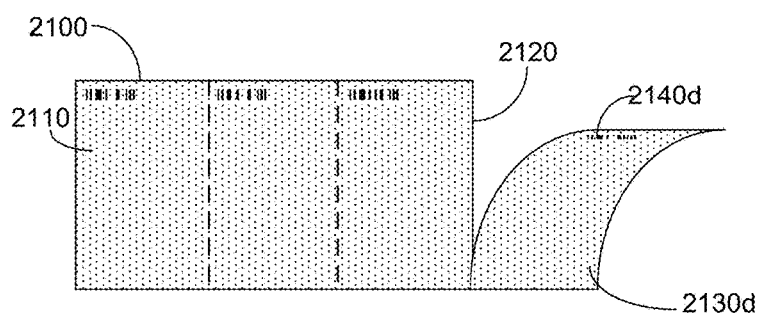
FIG. 21B is a skin-covering material with lines of tearable perforations.
Figure 21C:
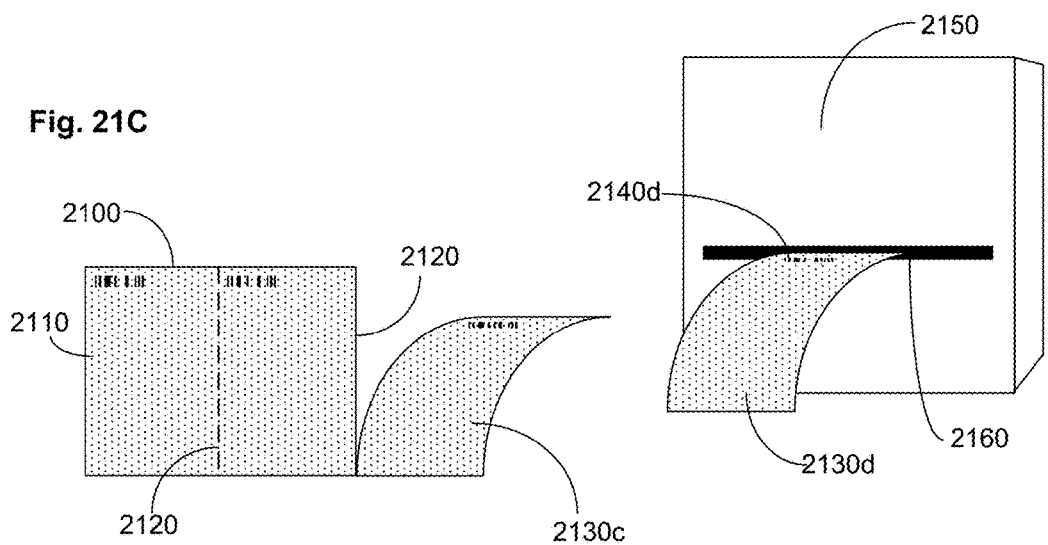
FIG. 21C is a schematic of a system including a skin-covering material with lines of tearable perforations.

FIG. 21 illustrates aspects of a system including a skin-covering material with perforations and an image-capture device with a feeding mechanism. FIG. 21A illustrates aspects of a skin-covering material 2100. Skin-covering material 2100 includes a plurality of signal-generating complexes 2110, one or more of the plurality of signal-generating complexes 2110 to emit one or more signals in response to at least one type of microbe. Skin-covering material 2100 further includes one or more tearable perforations 2120. In an aspect, one or more tearable perforations 2120 are added to the skin-covering material during manufacture, e.g., as part of a digital template from which the skin-covering material is manufactured through a 3D-printing process. In an aspect, one or more tearable perforations 2120 are added to the skin-covering material after manufacture, e.g., by punching a series of perforations into the skin-covering material. One or more tearable perforations 2120 are configured to separate skin-covering material 2100 into segments 2130a, 2130b, 2130c, and 2130d. Each segment of skin-covering material 2100 is coded with a corresponding registration mark 2140a, 2140b, 2140c, and 2140d. In this example, the registration marks are represented by a bar code, with each segment having a unique bar code. FIG. 21B illustrates further aspects of skin-covering material 2100. Skin-covering material 2100 is separable into segment 2130d along tearable perforations 2120. Segment 2130d includes registration mark 2140d, the latter of which is used to register segment 2130d relative to the other segments of skin-covering material 2100. In an aspect skin-covering material 2100 including at least one type of microbe captured by at least one of the plurality of signal-generating complexes from a skin surface of an individual is separated into one or more segments for analysis by an image-capture device. FIG. 21C illustrates aspects of a system including skin-covering material 2100 and image-capture device 2150.

Segment 2130d is fed into feeding mechanism 2160 of image-capture device 2150. Registration mark 2140d is "read" by a component of image-capture device 2150, e.g., a bar code scanner. Additional segments, e.g., 2130c are separable from skin-covering material 2100 and can also be subsequently fed into image-capture device 2150 for image analysis. The registration mark "read" from each segment is used to align the image information captured for each of the segments and aid in compiling a complete image of the entire skin-covering material 2100.

In an aspect, a skin-covering material includes a mouthpiece configured for use in a mouth region of an individual. In an aspect, one or more surfaces of the mouthpiece substantially conform in shape to a topography of at least a portion of the mouth region of the individual. In an aspect, the at least a portion of the mouth region of the individual includes at least a portion of an oral mucosa, tooth, gingiva, tongue, or palate. For example, the mouthpiece can be configured for insertion into a mouth and to cover at least a portion of an individual's gingiva and teeth. In an aspect, the mouthpiece includes an inner surface defined as those portions of the mouthpiece, e.g., one or more surfaces of the mouthpiece, in contact with the surfaces of the mouth, e.g., the surfaces of the oral mucosa, teeth, gingiva, tongue, and/or palate.

The mouthpiece includes a plurality of signal-generating complexes. The plurality of signal-generating complexes are associated with one or more surfaces of the mouthpiece, e.g., one or more inner surfaces in direct contact with one or more surfaces of the mouth region of the individual. The plurality of signal-generating complexes are configured to emit one or more signals in response to at least one type of microbe, e.g., bacteria, a virus, a fungus, or a parasite. Non-limiting examples of bacteria of the oral microbiota include *Streptococcus, Actinomyces, Veillonella, Fusobacterium, Porphromonas, Prevotella, Treponema, Nisseria, Haemophilis, Eubacteria, Lactobacterium, Capnocytophaga, Eikenella, Leptotrichia, Peptostreptococcus, Staphylococcus, Corynebacterium, Rothia, Selenomonas, Treponema, Propionibacterium*, and TM7 genera 1 and 5. See, e.g., Dewhirst et al. (2010) J. Bacteriology 192:5002-5017, which is incorporated herein by reference. Non-limiting examples of fungi of the oral microbiota include *Candida albicans, Aspergillus, Blastomyces dermatitidis, Cryptococcus neoformans*, and *Histoplasma capsulatum*. Non-limiting examples of viruses of the oral microbiota include herpes simplex virus (HSV-1), human papillomavirus, coxsackievirus, and Paramyxoviridae viruses. Additional non-limiting examples of microbes have been described above herein.

In an aspect, the plurality of signal-generating complexes are incorporated into the mouthpiece. In an aspect, the plurality of signal-generating complexes are substantially uniformly distributed throughout the mouthpiece. For example, the plurality of signal-generating complexes may be uniformly dispersed in a liquid or gelled form during manufacture of the mouthpiece. In an aspect, the plurality of signal-generating complexes are substantially distributed along the inner surface of the mouthpiece, e.g., the one or more surfaces of the mouthpiece substantially conforming in shape to the topography of the mouth region of the individual. In an aspect, the plurality of signal-generating complexes are functionally attached to the inner surface of the mouthpiece. In an aspect, the plurality of signal-generating complexes are covalently attached to the inner surface of the mouthpiece. In an aspect, the plurality of signal-generating complexes are non-covalently attached to the inner surface of the mouthpiece.

In an aspect, each of the plurality of signal-generating complexes associated with the one or more surfaces of the mouthpiece includes at least one signal-generating element operably and at least one specific microbe-binding element. In an aspect, the at least one signal-generating element is operably coupled to the at least one specific microbe-binding element, wherein the at least one signal-generating element is configured to emit one or more signals in response to at least one type of microbe bound to the operably coupled at least one specific microbe-binding element. Non-limiting examples of signal-generating elements and specific microbe-binding elements have been described above herein.

In an aspect, the skin-covering material can include a pre-formed mouthpiece. In an aspect, the pre-formed mouthpiece substantially conforms in shape to the topography of at least a portion of the mouth region of the individual. In an aspect, the pre-formed mouthpiece is personalized to substantially conform in shape to the topography of at least a portion of the mouth region of the individual. For example, a digital three-dimensional representation of the mouth region of the individual may be used to digitally render a pre-formed mouth piece, which is then used as a template for manufacturing the pre-formed mouthpiece using a three-dimensional printer. In an aspect, the pre-formed mouthpiece is generated using one or more images captured using an image-capture device, e.g., a three-dimensional laser scanning system, to image the topography of the mouth region of the individual. Non-limiting examples of imaging systems for this purpose include Cadent iTero® (from Align Technology, Inc., San Jose, Calif.) and E4D Dentist System (from ED4 Technologies Richardson, Tex.). Computer-aided design software can be used to generate a digitally rendered model of the pre-formed mouthpiece from which the pre-formed mouthpiece can be formed using an additive or a subtractive manufacturing process. Non-limiting examples of modeling programs and manufacturing processes applicable to generating the pre-formed mouthpiece have been described above herein.

The pre-formed mouthpiece can be formed from any of a number of materials capable of being shaped, molded, or printed. Non-limiting examples of shapeable, moldable or printable materials include acrylic, nylon, plastic, ceramic, resin, rubber, epoxy, thermoplastic, polymer, photopolymer, polyurethane, gel, hydrogel, latex, or silicone. Other non-limiting examples of materials have been described above herein.

In an aspect, the skin-covering material can include a peelable mouthpiece. In an aspect, the peelable mouthpiece can include any of a number of shapeable or moldable materials applied to at least a portion of the mouth region of the individual and subsequently removed, i.e., peeled, leaving an imprint, wherein the imprint substantially conforms in shape to a topography of the at least one portion of the mouth region of the individual. In an aspect, the shapeable or moldable material may harden over an elapsed period of time or in response to exposure to air. In an aspect, the shapeable or moldable material may be hardened in response to electromagnetic energy, e.g., light of a specific wavelength, or in response to elevated temperature. In an aspect, the peelable mouthpiece is formed from a settable material configured to undergo a phase change from a liquid or gelled phase to a flexible solid phase in response to an applied stimulus. The applied stimulus can include at least one of exposure to air, a thermal stimulus, or an electromagnetic stimulus. For example, a peelable mouthpiece can be formed by adding a settable material, e.g., sodium alginate, into an impression tray and inserting the tray with the settable material into the mouth of the individual and firmly pressing the tray into the teeth. Once the settable material has set, the impression tray including the peelable mouthpiece is removed from the mouth. Non-limiting settable materials for use in generating a peelable mouthpiece include sodium alginate, polyether, silicones, e.g., condensation-cured silicones and addition-cured silicones, polyvinyl siloxane, agar, or zinc oxide eugenol.

In an aspect, the mouthpiece, whether pre-formed or peelable from a settable material, further includes a medicament for treating a mouth condition. In an aspect, the medicament can be included as a layer on the one or more surfaces of the mouthpiece that come in contact with the surfaces of the mouth region. In an aspect, the medicament can be incorporated into the settable material. In an aspect, the medicament can be eluted by simple diffusion from a gel, e.g., a hydrogel, associated with the mouthpiece. Non-limiting examples of medicaments for treating a mouth condition include antibacterial agents, antifungal agents, antiviral agents, mouth deodorizer, fluoride treatment, probiotics, or prebiotics.

In an aspect, the mouthpiece includes at least one registration mark to register the mouthpiece to at least one landmark on one or more surfaces of the mouth region of the individual. The one or more landmarks on the one or more surfaces of the mouth region can include pigmented areas, dental topography, oral mucosa texture patterns, blemishes, anatomical features, or subsurface blood vessels. In an aspect, the one or more registration marks are incorporated into the manufacture of the mouthpiece based on one or more digital images of the mouth region including the one or more landmarks over which the mouthpiece will be placed.

In an aspect, the mouthpiece is deformable. In an aspect, the mouthpiece is deformable to facilitate imaging with an image-capture device. For example, the mouthpiece may be constructed of a material that is capable of being flattened for the purpose of performing imaging with a scanner, e.g., a flat-bed scanner. In an aspect, the mouthpiece can include one or more tearable perforations that allow the mouthpiece to be reshaped to facilitate imaging. For example, the mouthpiece can include one or more tearable or cuttable lines which when torn or cut allow the mouthpiece to be in a flattened state.

Figure 22:
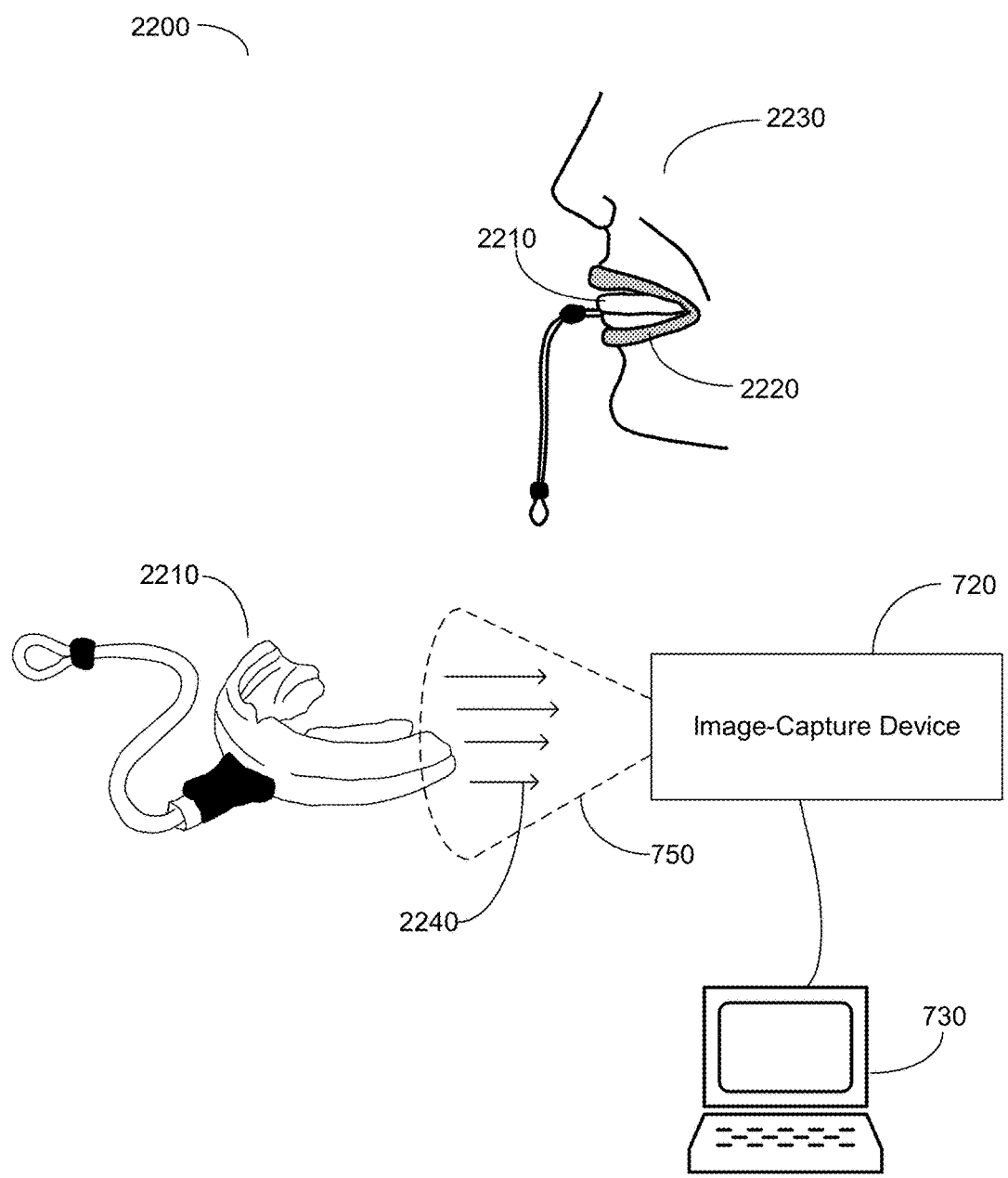
FIG. 22 is a schematic of a system including a mouthpiece for assessing microbiota of a mouth region.

In an aspect, the mouthpiece is part of a system for assessing microbiota of the mouth region. FIG. 22 illustrates aspects of a system including a mouthpiece. System 2200 includes mouthpiece 2210, image-capture device 720, and computing device 730. Mouthpiece 2210 is configured for insertion into mouth region 2220 of individual 2230. Mouthpiece 2210 includes an inner surface and an outer surface, wherein the inner surface includes one or more surfaces of the mouthpiece substantially conforming in shape to a topography of mouth region 2220 of individual 2230. The inner surface of mouthpiece 2210 includes a plurality of signal-generating complexes. System 2200 further includes image-capture device 720 including circuitry to capture at least one image of the inner surface of mouthpiece 2210 to image one or more signals 2240 emitted from one or more of the plurality of signal-generating complexes and to transform the captured at least one image into a digital output including information associated with at least one property and a spatial distribution of the imaged one or more signals 2240. In an aspect, one or more signals 2240 are emitted from the inner surface of mouthpiece 2210 in response to directed energy 750 from image-capture device 720. For example, one or more surfaces of mouthpiece 2210 can be imaged using a three-dimensional laser scanning system.

System 2200 further includes computing device 730 including a processor, computing device 730 operably coupled to image-capture device 720 through communications link 725. Computing device 730 includes circuitry configured to receive the digital output from image-capture device 720 including information associated with the at least one property and the spatial distribution of the imaged one or more signals 2240 emitted from the one or more of the plurality of signal-generating complexes in response to the at least one type of microbe; compare the properties of the imaged one or more signals 2240 emitted from the one or more of the plurality of signal-generating complexes in response to the at least one type of microbe with a database of emitted signals of reference signal-generating complexes; and generate a digital spatial profile of the at least one type of microbe based on the spatial distribution of the imaged one or more signals 2240 emitted from the one or more of the plurality of signal-generating complexes on mouthpiece 2210 in response to the at least one type of microbe. In an aspect, computing device 730 further includes circuitry configured to generate a recommended treatment regimen based on a comparison of the generated digital spatial profile with a reference digital spatial profile. In an aspect, computing device 730 further includes circuitry configured to generate a digital alignment of the generated digital spatial profile with a digital image of one or more surfaces of mouth region 2220 of the individual 2230 covered by the one or more surfaces of mouthpiece 2210. In an aspect, computing device 730 further includes circuitry to generate a personalized microbe profile from the generated digital alignment, the personalized microbe profile including at least one of the identity of the at least one type of microbe and a spatial distribution of the identified at least one type of microbe on the one or more surfaces of mouth region 2220.

In an aspect, system 2200 further includes at least one of an enhancing component to enhance binding of the at least one type of microbe to one or more of the plurality of signal-generating complexes associated with the one or more surfaces of mouthpiece 2210, the at least one enhancing component includes at least one of a thermal component, a vacuum component, a humidity component, a pressure component, a skin-softener, a detergent, or a lysing compound.

In an aspect, the method of assessing microbiota of skin includes a method of assessing microbiota of the oral cavity. In an aspect, the method of assessing the microbiota of the oral cavity includes receiving a digital output from an image-capture device, the digital output including information associated with at least one property and a spatial distribution of one or more signals emitted from one or more of a plurality of signal-generating complexes associated with one or more surfaces of a mouthpiece, the one or more signals emitted from the one or more of the plurality of signal-generating complexes in response to at least one type of microbe; identifying the at least one type of microbe by comparing the information associated with at least one property of the one or more signals emitted from the one or more of the plurality of signal-generating complexes with a database of signal properties of reference signal-generating complexes; generating a digital spatial profile of the at least one type of microbe based on the spatial distribution of the one or more signals emitted from the one or more of the plurality of signal-generating complexes in response to the at least one type of microbe; and reporting to a user an identification and the digital spatial profile of the identified at least one type of microbe. In an aspect, the method further includes generating a recommended treatment regimen based on the identification and spatial profile of the at least one type of microbe captured on the surface of the mouthpiece; and reporting the recommended treatment regimen to the user. Non-limiting aspects of a treatment regimen for a mouth region include instructions for brushing techniques; type and use of toothpaste, fluoride, mouth rinses, flossing, antibacterial agents, anti-fungal agents, antiviral agents, probiotics, or prebiotics; and recommendation regarding seeing a care provider such as a dentist, periodontist, or oral surgeon.

In an aspect, the method of assessing microbiota of skin includes a method of assessing microbiota of the oral cavity. In an aspect, the method of assessing the microbiota of the oral cavity includes applying a mouthpiece to a mouth region of an individual, the mouthpiece including one or more surfaces substantially conforming in shape to a topography of at least a portion of the mouth region of the individual, the one or more surfaces including attached thereto a plurality of signal-generating complexes, one or more of the plurality of signal-generating complexes configured to emit one or more signals in response to at least one type of microbe; removing the mouthpiece from the mouth region of the individual; capturing at least one image of the one or more surfaces of the mouthpiece with an image-capture device, the at least one image including one or more signals emitted from one or more of the plurality of signal-generating complexes in response to the at least one type of microbe and transforming the captured at least one image into a digital output including information associated with at least one property and a spatial distribution of the imaged one or more signals; receiving the digital output from the image-capture device including the information associated with at least one property and a spatial distribution of the imaged one or more signals emitted from the one or more of the plurality of signal-generating complexes in response to the at least one type of microbe; identifying the at least one type of microbe by comparing the information associated with the at least one property of the imaged one or more signals emitted from the one or more of the plurality of signal-generating complexes with a database of signal properties of reference signal-generating complexes; generating a digital spatial profile of the at least one type of microbe based on the spatial distribution of the imaged one or more signals emitted from the one or more of the plurality of signal-generating complexes; and reporting to a user an identification and a spatial profile of the identified at least one type of microbe bound to the one or more surfaces of the mouthpiece. In an aspect, the method further includes generating a recommended treatment regimen based on the identification and the digital spatial profile of the at least one type of microbe bound to the one or more surfaces of the mouthpiece; and reporting the recommended treatment regimen to the user. In an aspect, the method further includes generating a digital alignment of the digital spatial profile of the at least one type of microbe with a digital image of one or more surfaces of the mouth region of the individual covered by the mouthpiece; creating a personalize microbe profile from the digital alignment, the personalized microbe profile including the identification and a spatial profile of the identified at least one type of microbe on the one or more surfaces of the mouth region of the individual; generating a recommended treatment regimen based on the comparison of the personalized microbe profile with at least one reference microbe profile; and reporting to the user at least one of the personalized microbe profile or the recommended treatment regimen.

In an aspect, the method can further include deforming the mouthpiece to facilitate imaging with the image-capture device. In an aspect, deforming can include separating the mouthpiece into two or more pieces along one or more lines of tearable or cuttable perforations. In an aspect, deforming can include flattening a malleable non-planar mouthpiece into a substantially planar mouthpiece. In an aspect, deforming can include partially separating the mouthpiece in one or more places to flatten the mouthpiece to facilitate imaging.

In an aspect, the identity and spatial distribution of the at least one type of microbe on the one or more surfaces of the mouth region of the individual are indicative of a condition of the oral cavity, e.g., periodontal disease. For example, the amount of *Prevotella* at one site may indicate developing periodontal disease at that site, whereas an abudance of *Prevotella* at another site may indicate advanced disease at the second site. See, e.g., Liu et al. (2012) PLoS ONE 7(6):e37919, which is incorporated herein by reference. In an aspect, the identity and spatial distribution of the at least one type of microbe on the one or more surfaces of the mouth region of the individual can be used to correlate risk with systemic conditions, e.g., cardiovascular disease, pre-term birth, stroke, diabetes, pneumonia, or a disease of the central nervous system. See, e.g., Cockburn, et al. (2012) Investigative Genetics 3:19; Dewhirst et al. (2010) J. Bacteriology 192:5002-5017, which are incorporated herein by reference.

In an aspect, the method of assessing microbiota of skin at at least two different time points includes assessing microbiota of a mouth region of an individual at at least two different time points. In an aspect, the method includes receiving a first digital output from an image-capture device, the first digital output including information associated with at least one property and a spatial distribution of a first set of one or more signals emitted at a first time point from at least one of a plurality of signal-generating complexes associated with one or more surfaces of a first mouthpiece; receiving a second digital output from the image-capture device, the second digital output including information associated with at least one property and a spatial distribution of a second set of one or more signals emitted at a second time point from at least one of a plurality of signal-generating complexes associated with one or more surfaces of a second mouthpiece; comparing the first digital output with the second digital output; generating a recommended treatment regimen based one comparison of the first digital output with the second digital output; and reporting the recommended treatment regimen to a user.

FIG. 23 illustrates aspects of an article of manufacture. Article of manufacture 2300 includes non-transitory machine readable media bearing one or more instructions for assessing microbiota of skin in block 2310. The non-transitory machine readable media stores instructions and/or data for use in assessing microbiota of skin. In an embodiment, non-transitory machine readable media 2310 can be computer readable media. In an embodiment, non-transitory machine readable media 2310 can be recordable-type media. Computer readable media may also be recordable-type media, and the qualities of being "computer readable" and "recordable-type" should not be construed as being mutually exclusive, though in some cases a computer readable media may not be a recordable-type media, and vice versa. Machine readable media include volatile and nonvolatile, removable and non-removable media implemented in any method or technology for storage of information such as machine readable instructions, data structures, program modules, or other data. Non-transitory machine readable media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other media which can be used to store the desired information. In a further embodiment, computer storage media may include a group of computer storage media devices. In an embodiment, machine readable media may include an information store. In an embodiment, an information store may include a quantum memory, a photonic quantum memory, or atomic quantum memory. Combinations of any of the above may also be included within the scope of non-transitory machine readable media.

Non-transitory machine readable media bearing one or more instructions for assessing microbiota of skin, as shown in block 2310, includes one or more instructions for receiving a digital output from an image-capture device, the digital output including information associated with at least one property and a spatial distribution of one or more signals emitted from one or more of a plurality of signal-generating complexes associated with an inner surface of a skin-covering material, the one or more signals emitted from the one or more of the plurality of signal-generating complexes in response to at least one type of microbe in block 2320; one or more instructions for comparing the information associated with at least one property of the one or more signals emitted from the one or more of the plurality of signal-generating complexes with a database of signal properties of reference signal-generating complexes in block 2330; one or more instructions for generating a microbe profile including the at least one property and the spatial distribution of the one or more signals emitted from the one or more of the plurality of signal-generating complexes in block 2340; one or more instructions for generating a recommended treatment regimen for an individual based on a comparison of the microbe profile with a reference microbe profile in block 2350; and one or more instructions for reporting to a user at least one of the microbe profile or the recommended treatment regimen in block 2360.

In an aspect, non-transitory machine readable media 2310 can further include one or more instructions for receiving the digital output from at least one digital camera. In an aspect, non-transitory machine readable media 2310 can include one or more instructions for receiving the digital output from at least one scanning device, wherein the scanning device includes at least one of a passive scanning device, an active scanning device, a three-dimensional scanning device, an optical scanning device, a fluorescence scanning device, an acoustic scanning device, or an electromagnetic scanning device.

In an aspect, non-transitory machine readable media 2310 can further include one or more instructions for identifying the at least one type of microbe by comparing the information associated with the at least one property of the one or more signals emitted from the one or more of the plurality of signal-generating complexes with the database of signal properties of the reference signal-generating complexes. In an aspect, non-transitory machine readable media 2310 can include one or more instructions for comparing the at least one of an optical property, fluorescence property, an infrared emission property, an acoustic property, a magnetic property, an electromagnetic property, or an electrical property of the one or more signals emitted from the signal-generating complex with a database of signal properties associated with one or more reference signal-generating complexes. In an aspect, non-transitory machine readable media 2310 can further include one or more instructions for comparing at least one of a wavelength, a frequency, or an amplitude of the one or more signals emitted from the signal-generating complex with a database of signal properties associated with one or more reference signal-generating complexes. In an aspect, the database of signal properties associated with one or more reference signal-generating complexes is included in the article of manufacture 2300.

In an aspect, non-transitory machine readable media 2310 includes one or more instructions for generating a digital spatial profile of the at least one type of microbe based on the spatial distribution of the one or more signals emitted from the one or more of the plurality of signal-generating complexes. In an aspect, non-transitory machine readable media 2310 includes one or more instructions for generating a digital alignment of the digital spatial profile of the at least one type of microbe with a digital image of a skin surface of an individual covered by the inner surface of the skin-covering material. In an aspect, non-transitory machine readable media 2310 can include one or more instructions for detecting one or more features depicted in the digital images, e.g., the physical landmarks, and match these features with features in the digital spatial profile, e.g., the registration marks. The one or more instructions can include one or more instructions for performing feature-based matching using, e.g., segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. The one or more instructions may further include one or more instructions for matching the features detected in the one or more images of skin surface of the individual with features in the digital spatial profile using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods.

In an aspect, non-transitory machine readable media 2310 includes one or more instructions for generating a personalized microbe profile for the individual from the digital alignment, the personalized microbe profile including an identification and a spatial profile of the at least one type of microbe on the skin surface of the individual; one or more instructions for generating the recommended treatment regimen based on a comparison of the personalized microbe profile with the reference profile; and one or more instructions for reporting to the user at least one of the personalized microbe profile or the recommended treatment regimen. In an aspect, non-transitory machine readable media 2310 includes one or more instructions for reporting at least one of the personalized microbe profile or the recommended treatment regimen to a user that is the individual for whom the microbiota assessment was performed. In an aspect, non-transitory machine readable media 2310 includes one or more instructions for reporting at least one of the personalized microbe profile or the recommended treatment regimen to a user that is a service provider, e.g., a medical practitioner or other provider who is performing the microbiota assessment. In an aspect, non-transitory machine readable media 2310 includes one or more instructions providing a visual representation of the personalized microbe profile and/or the recommended treatment regimen to a user on a display. In an aspect, non-transitory machine readable media 2310 includes one or more instructions for providing a printout to the user of the personalized microbe profile and/or the recommended treatment regimen. In an aspect, non-transitory machine readable media 2310 includes one or more instructions for exporting the personalized microbe profile and/or the recommended treatment regimen to a computing device, e.g., a second computing device.

In an aspect, non-transitory machine readable media 2310 includes one or more instructions for generating a recommended treatment regimen based on comparing microbiota of a skin surface of an individual at two or more points in time, the one or more instructions including one or more instructions for receiving a first digital output from an image-capture device, the first digital output including information associated with at least one property and a spatial distribution of a first set of one or more signal emitted at a first time point from at least one of a plurality of signal-generating complexes associated with an inner surface of a first skin-covering material; one or more instructions for receiving a second digital output from an image capture device at block, the second digital output including information associated with at least one property and a spatial distribution of a second set of one or more signal emitted at a second time point from at least one of a plurality of signal-generating complexes associated with an inner surface of a second skin-covering material; one or more instructions for comparing the first digital output with the second digital; one or more instructions for generating a recommended treatment regimen based on the comparison of the first digital output with the second digital output; and one or more instructions for reporting the recommended treatment regimen to a user.

In an aspect, non-transitory machine readable media 2310 includes one or more instructions for comparing the personalized microbe profile with a reference microbe profile generated for the individual at a previous point in time, e.g., at a young age, before the onset of a skin disorder, or before and/or after a treatment regimen to treat a skin disorder. In an aspect, non-transitory machine readable media 2310 includes one or more instructions for comparing the personalized microbe profile with a reference microbe profile generating for one or more other individuals, e.g., an average "normal" profile or the profile of an individual with a desirable microbe profile as exemplified by "healthy" looking skin.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

Prophetic Example 1: A Preformed Skin-Covering Material Including a Plurality of Signal-Generating Complexes and Use Thereof Construction and use of a skin-covering material including a plurality of signal-generating complexes are described. The skin-covering material is constructed of a semi-rigid material to substantially conform in shape to the topography of an individual's face. A digitally rendered model of the skin-covering material is generated from one or more digital images of the skin surface of the individual's face. Briefly, two charge-coupled device cameras and a projector connected to a computer are used to scan the skin surface of the individual's face as described in Feng et al. *Brit. J. Oral Maxillofacial Surg.* (2010) 48:105-109, which is incorporated herein by reference. The individual's face is exposed to structured light to collect an optical representation of the body region by a point cloud of up to 300,000 points in three-dimensional coordinates. The three-dimensional coordinates are acquired by the computer and used to construct a digitally rendered model of the skin-covering material using a CAD/CAM software package, e.g., Geomagic Studio (Morrisville, N.C.).

The skin-covering material is formed from the digitally rendered model using a commercially available 3D printer. An example of a 3D printer appropriate for a physician's office, for example, includes the uPrint SE system (from, e.g., Stratasys, Eden Prairie, Minn.). In this example, software associated with the 3D printer system converts an STL format file containing data regarding the digitally rendered model of the skin-covering material into deposition paths that guide the extrusion head of the printer, printing the skin-covering material layer by layer. The skin-covering material, with an overall thickness of 3 mm, is produced from a thermoplastic material, e.g., acrylonitrile butadiene styrene (ABS). Several pre-formed skin-covering materials specifically designed for the individual can be printed and used at subsequent treatment appointments. Similarly, the information used to form the skin-covering material can be saved for printing additional skin-coverings in the future.

The inner surface is further modified with poly(dimethylsiloxane) and cross-linkers to facilitate attachment of oligonucelotides to a substrate as described in Blank et al. (2003) Proc. Natl. Acad. Sci., USA. 100:11356-11360, which is incorporated herein by reference. Briefly, the inner surface of the pre-formed skin-covering material is coated with a thin layer of PDMS (poly(dimethylsiloxane); Sylgard 184, Dow Corning, Midland, Mich.). The PDMS is derivatized with 3-aminopropyldimenthylethoxysilane to generate free amino groups to which a heterobifunctional cross-linking agent, e.g., NHS-PEG-COOH (from, e.g., Pierce, Rockford, Ill.), is attached.

One or more fluorescently labeled aptamers specific for binding at least one type of microbe, e.g., a bacteria, are generated as described by Chen et al. (2007) Biochem. Biophys. Res. Commun. 357:743-748 and Jhaveri, et al. (2000) Nature Biotech. 18:1293-1897, which are incorporated herein by reference. The aptamers are designed such that binding of a microbe leads to an increase in fluorescence intensity. Briefly, a library of fluorescently labeled oligonucleotides (45-60 residues in length) is generated using fluorescein-12-ATP during synthesis. The fluorescein-labeled library of oligonucleotides is screened against whole bacteria, e.g., whole *Staphylococcus aureus*, in which the whole *Staphylococcus aureus* are incubated with the fluorescein-labeled oligonucleotides, washed, and bound oligonucleotides are isolated. Those oligonucleotides that bind with high affinity during the screening process are further screened for fluorescence signaling properties in response to binding the target bacteria, e.g., a detectable increase in fluorescein signaling in response to binding *Staphylococcus aureus*. The resulting aptamers are further end-modified with an amine group during final synthesis.

The amino-modified, fluorescently labeled aptamer is mixed with a cross-linker, e.g., ethylene diaminecarbodiimide (EDC), and applied to the carboxy-modified inner surface of the skin-covering material. The skin-covering material is rinsed with a physiological buffer, e.g., phosphate buffered saline.

The inner surface of the skin-covering material is placed in contact with the individual's face for 5-10 minutes with manual applied pressure, e.g., using hands to press the skin-covering material onto the skin surface. The skin-covering material with adhered microbes is removed from the skin surface and subjected to imaging with an image-capture device.

The inner surface of the skin-covering material is imaged using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Green fluorescent spots or regions corresponding to fluorescein-associated fluorescence are imaged using the CCD camera.

The spatial distribution of the fluorescent spots or regions captured by the image-capture device is digitally overlaid with the corresponding digital image of the individual's face. A color scale may be used to highlight the abundance of the bacteria detected on the skin surface. A personalized microbe profile is generated and includes the identification and spatial distribution of *Staphylococcus aureus* on the individual's face. The personalized microbe profile is provided to the individual as a printout and accompanied by a recommended treatment regimen including skin cleansing and use of a nonprescription triple-antibiotic mixture to treat the *Staphylococcus aureus* infection.

Prophetic Example 2: A Preformed Skin-Covering Material Including a Plurality of Signal-Generating Complexes and Use Thereof Construction and use of a pre-formed skin-covering material including a plurality of signal-generating complexes are described. A pre-formed skin-covering material is formed using methods such as described in Example 1. In this example, the pre-formed skin-covering material is formed from PMMA (poly(methyl methacrylate)) with a 3D printer (e.g., Objet Connex 3D printer, from Stratasys Ltd. Minneapolis, Minn.) using a digitally rendered model of an individual's skin surface. The inner surface of the skin-covering material is subjected to reactive ion etching (ME) using an inductively coupled oxygen plasma to generate a textured surface conducive to antibody binding. See, e.g., Rucker et al. (2005) *Langmuir* 21:7621-7625, which is incorporated herein by reference.

Quantum dot/antibody conjugates are generated against *Propionibacterium acnes* using methods described by Dwarakanath et al. (2004) *Biochem. Biophys. Res. Commun.* 325:739-743, which is incorporated herein by reference. Antibodies to *Propionibacterium acnes* can be generated from heat inactivated bacteria as described in Nakatsuji et al. (2008) *J. Invest. Dermatol.* 127:2451-2457, which is incorporated herein by reference. Fort Orange EviTag quantum dots (about 6 micrograms, from Evident Technologies, Troy, N.Y.) are modified with the cross-linker EDC (1-ethyl-3-(3-dimethylamino propyl)carbodiimide) in phosphate-buffered saline at room temperature for an hour. About 1-2 milligrams of the *Propionibacterium acnes* antibody are added to the quantum dots, and the mixture further incubated for 2 hours. The solution is transferred to a spin filter column apparatus (Omega Macrosep 300k, from Pall, Ann Arbor, Mich.) and spun at 3000 g for 30-60 minutes. The resulting retentate contains the quantum dot/antibody conjugate.

The textured inner surface of the preformed skin-covering material is incubated with the *Propionibacterium acnes* quantum dot/antibody conjugate. The antibodies are prepared in an aqueous solution, e.g., phosphate buffered saline, and applied in sufficient volume to cover the entirety of the inner surface and allowed to dry for 1 hour. The inner surface is rinsed with phosphate buffered saline supplemented with 0.1% Tween20 to remove non-bound antibody.

The pre-formed skin-covering material including antibodies against *Propionibacterium acnes* quantum dot/antibody conjugate is applied to a skin surface of an individual to selectively capture these bacteria from the skin surface. The skin-covering material is removed from the skin surface and subjected to fluorescence scanning to detect a shift in fluorescence associated with *Propionibacterium acnes* binding to the quantum dot/antibody conjugate. Fort Orange EviTag quantum dots conjugated to an antibody normally emit at about 600 nm, but emission fluorescence is shifted to about 450 nm in response to binding the antibody target, e.g., the *Propionibacterium acnes*. The inner surface of the skin-covering material is imaged using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Green fluorescent spots or regions corresponding to shifted fluorescence associated with Fort Orange EviTag quantum dot/antibody conjugate are imaged using the CCD camera.

The spatial distribution of the fluorescent signal emitted from the Fort Orange EviTag quantum dot/antibody conjugate when bound to *Propionibacterium acnes* is provided to a user as part of a personalized microbe profile the includes a color spatial profile, for example, green for *Propionibacterium acnes* overlaid on an image of the individual's skin surface. Fluorescent spots or regions captured by the image-capture device are digitally overlaid with the corresponding digital image of the individual's skin surface using image registration software. A color scale may be used to highlight the abundance of the bacteria detected at different locations on the skin surface. The personalized microbe profile is exported to the individual's smart phone and includes a recommended treatment regimen including skin cleansing with gentle liquid cleanser, use of a non-prescription medication containing benzoyl peroxide, and recommended non-comedogenic cosmetic brands and/or moisturizers.

Prophetic Example 3: A Peelable Skin-Covering Material Including a Plurality of Signal-Generating Complexes for Assessing Microbiota of Skin Construction and use of a peelable skin-covering material including a plurality of signal-generating complexes are described. The peelable skin-covering material includes a plurality of signal-generating complexes, the signal-generating complexes including at least one bacteria-binding aptamer operably coupled to at least one signal-generating element, e.g., quantum dots. The bacteria-binding aptamers are configured to specifically bind *Propionibacterium acnes*. The aptamers further include quantum dots conjugated to the aptamer and configured to fluoresce in response to binding of *Propionibacterium acnes* to the bacteria-binding component of the aptamer.

An aptamer that specifically binds *Propionibacterium acnes* is generated using methods described by Chen et al. for generating an aptamer against bacteria (see Chen et al. (2007) *Biochem. Biophys. Res. Commun.* 357:743-748, which is incorporated herein by reference). Briefly, aptamers against whole *Propionibacterium acnes* can be isolated from a large library of $10^{14}$ to $10^{15}$ random oligonucleotides using an iterative in vitro selection procedure (SELEX) in which the whole bacteria are incubated with the oligonucleotides, the washed, and bound oligonucleotides are amplified using the polymerase chain reaction (PCR) method, and then re-incubated with bacteria. One or more aptamers with specific affinity for *Propionibacterium acnes* are isolated after 8-10 rounds of selection.

A plurality of signal-generating aptamers are formed by modifying the aptamers with a signal-generating element, e.g., quantum dots, as described by Dwarakanath et al. (2004) *Biochem. Biophys. Res. Commun.* 325:739-743, which is incorporated herein by reference. Briefly, the aptamer oligonucleotide sequence is modified by incorporation of 5 prime-disulfide primers during the final PCR amplification. The disulfide ends are reduced to sulfhydryls in 1% dithiothreitol and the 5'-sulfhydryl-aptamers desalted over a Sephadex G-25 column. A linker, e.g., N-beta-maleimidopropionic acid (BMPA, Pierce Biotechnology, Rockford, Ill.) is attached to the sulfhydryl group of the aptamer per the manufacturer's instructions. The aptamer is conjugated with amine-modified quantum dots (e.g., amine-EviTags, Adirondack Green, from Evident Technologies, Troy, N.Y.) in the presence of ethylene diaminecarbodiimide (EDC) to generate the signal-generating aptamer.

A settable material, e.g., polyvinyl alcohol, is prepared, mixed with the plurality of signal-generating aptamers, and applied to a skin surface of an individual. A peelable skin-covering material is generated using polyvinyl alcohol as a settable material using methods such as described in U.S. Pat. No. 5,747,022; U.S. Patent Application 2005/0019291, which are incorporated herein by reference. Briefly, for a 100 ml solution of settable material, polyvinyl alcohol (10 gm; PVA-523, Sekisui America Corporation, Secaucus, N.J.) is heated in distilled water at 85° C. for 30 minutes. After cooling, sodium polyacrylate (1.5 gm; Rapithix A-60, Ashland Specialty Ingredients, Wayne, N.J.) is added to the solution along with glycerin (3 gm). Ethanol (10 ml) is added and the solution volume brought up to 100 ml with distilled water. The aptamer/quantum dot signal-generating complex is thoroughly mixed into the cooled polyvinyl alcohol solution just prior to application of the solution to the skin surface of the individual. The polyvinyl alcohol solution is applied as in a thin layer to the surface of the individual's skin and allowed to air dry for 15 to 30 minutes.

Once solidified, one or more registration marks can be added to the polyvinyl alcohol peelable skin-covering. Registration marks can be placed on the polyvinyl alcohol peelable skin-covering using ink (e.g., fluorescent ink) pushed through the outer surface to the inner surface of the skin-covering over landmarks on the individual's face, e.g., freckles, moles, or other markings visible through the translucent gelatin. A digital image of the polyvinyl alcohol peelable skin-covering on the skin-surface of the individual is also taken to document where the landmarks are on the skin surface relative to the registration marks. The polyvinyl alcohol peelable skin-covering material is then carefully peeled from the individual's skin, removing with it microbes associated with the skin surface.

The polyvinyl alcohol peelable skin-covering including the aptamer/quantum dot signal-generating complex is subjected to imaging with an image-capture device. Binding of bacteria to an aptamer modified with Adirondack Green quantum dots results in a blue shift, with emission spectra shifting from about 600 nm to about 450 nm when excited at about 400 nm. See, e.g., described by Dwarakanath et al. (2004) *Biochem. Biophys. Res. Commun.* 325:739-743, which is incorporated herein by reference. The inner surface of the skin-covering material is imaged using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Green fluorescent spots or regions corresponding to shifted fluorescence associated with Adirondack Green quantum dot/aptamer conjugate are imaged using the CCD camera.

The spatial distribution of the fluorescent signal emitted from the Adirondack Green quantum dot/aptamer conjugate when bound to *Propionibacterium acnes* is provided to a user as part of a personalized microbe profile and includes a color spatial profile, for example, green for *Propionibacterium acnes* overlaid on an image of the individual's skin surface. Fluorescent spots or regions captured by the image-capture device are digitally overlaid with the corresponding digital image of the individual's skin surface using image registration software. A color scale may be used to highlight the abundance of the bacteria detected at different locations on the skin surface. The personalized microbe profile is exported to the individual's smart phone and includes a recommended treatment regimen including skin cleansing with gentle liquid cleanser, use of a non-prescription medication containing benzoyl peroxide, and recommended non-comedogenic cosmetic brands and/or moisturizers.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for assessing microbiota of skin comprising:
an image-capture device including circuitry to capture at least one image of an inner surface of a skin-covering material, wherein the skin-covering material includes an inner surface and an outer surface, the inner surface of the skin-covering material substantially conforming in shape to a topography of a skin surface of an individual and including attached thereto a plurality of signal-generating complexes, one or more of the plurality of signal-generating complexes configured to emit one or more signals in response to at least one type of microbe, and wherein the image includes one or more signals emitted from one or more of the plurality of signal-generating complexes in response to the at least one type of microbe and to transform the captured at least one image into a digital output including information associated with at least one property and a spatial distribution of the imaged one or more signals; and
a computing device including a processor, the computing device operably coupled to the image-capture device and including circuitry configured to
receive the digital output from the image-capture device including the information associated with the at least one property and the spatial distribution of the imaged one or more signals emitted from the one or more of the plurality of signal-generating complexes in response to the at least one type of microbe;

compare the properties of the imaged one or more signals emitted from the one or more of the plurality of signal-generating complexes in response to the at least one type of microbe with a database of emitted signals of reference signal-generating complexes; and generate a digital spatial profile of the at least one type of microbe based on the spatial distribution of the imaged one or more signals emitted from the one or more of the plurality of signal-generating complexes in response to the at least one type of microbe.

2. The system of claim 1, wherein the skin-covering material includes at least one registration mark to register the skin-covering material to at least one landmark on the skin surface of the individual.

3. The system of claim 1, wherein at least a portion of the inner surface of the skin-covering material includes a medicament.

4. The system of claim 1, wherein the plurality of signal-generating complexes are substantially uniformly distributed over at least a portion of the inner surface of the skin-covering material.

5. The system of claim 1, wherein the skin-covering material includes a plurality of signal-generating complexes of at least one first type and a plurality of signal-generating complexes of at least one second type.

6. The system of claim 5, wherein the plurality of signal-generating complexes of the at least one first type are configured to emit one or more signals of a first type in response to at least one first type of microbe and the plurality of signal-generating complexes of the at least one second type are configured to emit one or more signals of a second type in response to at least one second type of microbe.

7. The system of claim 1, wherein each of the plurality of signal-generating complexes includes at least one signal-generating element and at least one specific microbe-binding element.

8. The system of claim 1, wherein the image-capture device includes at least one scanning device.

9. The system of claim 1, wherein the image-capture device includes at least one of a spectrometer or spectrophotometer.

10. The system of claim 1, wherein the image-capture device includes circuitry configured to capture at least one image of at least one first portion of the inner surface of the skin-covering material and at least one second portion of the inner surface of the skin-covering material adjacent to the at least one first portion; and generate a composite image including the at least one image of the at least one first portion of the inner surface of the skin-covering material and the at least one image of the at least one second portion of the inner surface of the skin-covering material.

11. The system of claim 1, wherein the image-capture device includes a feeding mechanism and an imaging surface sized to accommodate at least a portion of the skin-covering material, the feeding mechanism configured to feed in the at least a portion of the skin-covering material onto the imaging surface.

12. The system of claim 1, wherein the computing device includes circuitry configured to compare the generated digital spatial profile with a reference digital spatial profile.

13. The system of claim 12, wherein the reference digital spatial profile includes a historical digital spatial profile previously acquired for the individual.

14. The system of claim 12, wherein the computing device includes circuitry configured to generate a recommended treatment regimen based on the comparison of the generated digital spatial profile with the reference digital spatial profile.

15. The system of claim 1, wherein the computing device includes circuitry configured to generate a digital alignment of the generated digital spatial profile with a digital image of the skin surface of the individual covered by the inner surface of the skin-covering material.

16. The system of claim 1, wherein the computing device includes circuitry configured to generate a recommended treatment regimen based on an identity of the at least one type of microbe and a spatial distribution of the at least one type of microbe on the skin surface of the individual; and report the generated recommended treatment regimen to a user.

17. The system of claim 1, further comprising:

at least one enhancing component to enhance interaction of the at least one type of microbe to the one or more of the plurality of signal-generating complexes.

18. A method comprising:

capturing at least one image of an inner surface of a skin-covering material with an image-capture device, wherein the skin-covering material has been removed from a skin surface of an individual, the inner surface of the skin-covering material substantially conforming in shape to a topography of the skin surface of the individual and including attached thereto a plurality of signal-generating complexes, one or more of the plurality of signal-generating complexes configured to emit one or more signals in response to at least one type of microbe, and wherein the at least one image includes one or more signals emitted from one or more of the plurality of signal-generating complexes in response to the at least one type of microbe and transforming the captured at least one image into a digital output including information associated with at least one property and a spatial distribution of the imaged one or more signals;

receiving the digital output from the image-capture device, the digital output including information associated with at the least one property and the spatial distribution of the imaged one or more signals emitted from the one or more of the plurality of signal-generating complexes in response to the at least one type of microbe;

identifying the at least one type of microbe by comparing the information associated with the at least one property of the imaged one or more signals emitted from the one or more of the plurality of signal-generating complexes with a database of signal properties of reference signal-generating complexes;

generating a digital spatial profile of the at least one type of microbe based on the spatial distribution of the imaged one or more signals emitted from the one or more of the plurality of signal-generating complexes; and reporting to a user an identification and the digital spatial profile of the identified at least one type of microbe.

19. The method of claim 18, further comprising:

generating a digital alignment of the digital spatial profile of the at least one type of microbe with a digital image of the skin surface of the individual covered by the inner surface of the skin-covering material;

creating a personalized microbe profile from the digital alignment, the personalized microbe profile including the identification and a spatial profile of the identified at least one type of microbe on the skin surface of the individual;

generating a recommended treatment regimen based on a comparison of the personalized microbe profile with at least one reference microbe profile; and reporting to the user at least one of the personalized microbe profile or the recommended treatment regimen.

20. The method of claim 18, further comprising:

generating a recommended treatment regimen based on the identification and the digital spatial profile of the at least one type of microbe; and reporting the recommended treatment regimen to the user.

* * * * *